US 6,673,012 B2

(12) United States Patent
Fujii et al.

(10) Patent No.: US 6,673,012 B2
(45) Date of Patent: Jan. 6, 2004

(54) CONTROL DEVICE FOR AN ENDOSCOPE

(75) Inventors: Yoshinori Fujii, Saitama (JP); Akira Sugiyama, Kanagawa (JP)

(73) Assignee: Pentax Corporation, Tokyo (JP)

(*) Notice: Subject to any disclaimer, the term of this patent is extended or adjusted under 35 U.S.C. 154(b) by 242 days.

(21) Appl. No.: 09/836,505

(22) Filed: Apr. 18, 2001

(65) Prior Publication Data

US 2001/0037051 A1 Nov. 1, 2001

(30) Foreign Application Priority Data

| Apr. 19, 2000 | (JP) | 2000-117658 |
| Apr. 24, 2000 | (JP) | 2000-121994 |
| May 1, 2000 | (JP) | 2000-132203 |
| Jun. 7, 2000 | (JP) | 2000-170907 |
| Jul. 28, 2000 | (JP) | 2000-229088 |
| Jul. 28, 2000 | (JP) | 2000-229089 |

(51) Int. Cl.$^7$ ................................................ A61B 1/00
(52) U.S. Cl. ........................ 600/146; 600/139; 600/101
(58) Field of Search .......................... 600/101, 118, 600/137, 138, 139, 146–150

(56) References Cited

U.S. PATENT DOCUMENTS

| 4,078,555 A | 3/1978 | Takahashi |
| 4,461,282 A | 7/1984 | Ouchi et al. |
| 4,617,914 A | 10/1986 | Ueda |
| 5,007,406 A | 4/1991 | Takahashi et al. |
| 5,014,685 A | 5/1991 | Takahashi |
| 5,507,717 A | 4/1996 | Kura et al. |

FOREIGN PATENT DOCUMENTS

| JP | 58-25137 | 2/1983 |
| JP | 63115533 | 5/1988 |
| JP | 5-115428 | 5/1993 |
| JP | 6-327613 | 11/1994 |
| JP | 6-327614 | 11/1994 |
| JP | 9-84754 | 3/1997 |

Primary Examiner—Thor Campbell
(74) Attorney, Agent, or Firm—Greenblum & Bernstein, P.L.C.

(57) ABSTRACT

An endoscope having an elongated insertion portion provided at a distal end thereof with a steerable bendable portion, includes at least one steering member which is rotated to bend the steerable bendable portion; at least one locking member which is rotated to lock the steering member, the steering member and the locking member being rotated about a common axis; and at least one axially-movable lock member which moves relative to the steering member along the common axis without rotating about the common axis to lock and unlock the steering member when the locking member is turned in a first rotational direction and a second rotational direction, respectively.

64 Claims, 28 Drawing Sheets

CONTROL DEVICE FOR AN ENDOSCOPE

BACKGROUND OF THE INVENTION

1. Field of the Invention

The present invention relates to a control device having a rotary steering device. The present invention also relates to a control device of an endoscope which has a rotary steering device for steering the distal end of an endoscope, and a locking device for locking the rotary steering device to lock the distal end of the endoscope.

2. Description of the Related Art

A typical endoscope is generally provided with an insertion portion which is inserted into a hollow organ or part such as an body cavity or an inner part of a jet engine, and a rotary steering device for steering the distal end of the endoscope to adjust the distal end to a desired curved shape, i.e., to adjust the orientation of the tip of the distal end. Manually turning an angle knob (a control knob) provided on the control body of the endoscope about a stationary rotational shaft causes the distal end of the insertion portion of the endoscope to bend in right and left or upward and downward via a control wire having a distal portion anchored to the distal end of the insertion portion of the endoscope. In general, the endoscope is provided with a locking device for locking the angle knob to lock the distal end of the endoscope to maintain the desired curved shape thereof. This locking device is operated by manually operating a lock knob which is rotatably provided about the aforementioned rotational shaft. Such a locking device is known in the art in the form of a friction locking device which includes a friction pad provided on the lock knob side and another friction pad provided on the angle knob side, wherein the friction pad provided on the lock knob side moves toward and away from the friction pad provided on the angle knob side, in a direction of the axis of the aforementioned rotational shaft, by rotation of the lock knob, and wherein the friction pad provided on the angle knob side rotates together with the angle knob by rotation of the angle knob. In this locking device, if the lock knob is turned in a predetermined rotational direction, the friction pad provided on the lock knob side moves toward the friction pad provided on the angle knob side while rotating about the rotational shaft together with the lock knob via a screw mechanism and eventually comes into contact with the friction pad provided on the angle knob side. Further rotational movement of the lock knob in the same rotational direction causes the friction pad provided on the lock knob side to come into pressing contact firmly with the friction pad provided on the angle knob side to thereby lock the angle knob by friction resistance generated between the friction pad provided on the lock knob side and the friction pad provided on the angle knob side. With the frictional locking device having such structure, the angle knob is prevented from rotating unintentionally, which prevents the distal end of the endoscope from moving unintentionally.

One problem which resides in the endoscope having such a frictional locking device, is that the rotation of the friction provided on the lock knob side pad may be transmitted slightly to the angle knob via the friction pad provided on the angle knob side, causing the shape of the distal end of the endoscope to change slightly since the friction pad provided on the lock knob side comes into pressing contact with the friction pad provided on the angle knob side while rotating about the aforementioned rotational shaft when the lock knob is turned to lock the angle knob. As a result, the distal end of the endoscope may be locked to an undesired curved shape with the frictional locking device.

Endoscopes provided with a plurality of angle knobs for steering the distal end of the endoscope are known in the art. For instance, an endoscope having two angle knobs is known. In this endoscope, the distal end of the endoscope swings in two directions perpendicular to each other by operating the two angle knobs, respectively, via a pair of control wires having respective distal portions anchored to the distal end of the endoscope. Therefore, the distal end of the endoscope can be freely deflected right, left, upward and downward by operating the two angle knobs.

However, in such a conventional type of endoscope, in the case where the above described frictional locking device is provided for each of the two angle knobs, there is a possibility that the operational force of the frictional locking device given to one of the two angle knobs exerts an adverse effect on the operability of the other angle knob. For instance, in the case where the two angle knobs are coaxially arranged adjacent to each other and where the frictional locking device is structured so that one of the two angle knobs is locked by a pressing force toward the other angle knob, this pressing force may have an adverse effect on the other angle knob that does not have to be locked to thereby deteriorate the operability of the other angle knob that needs to be manually rotatable freely and smoothly.

A rotary control member such as a knob or a lever is widely used as a control member for adjusting or locking the distal end of an endoscope, i.e., as an element of the aforementioned steering device or the aforementioned locking device. Generally, such a rotary control member is held rotatably via a retaining mechanism for preventing the rotary control member from coming off a control center shaft (a rotational shaft) in an axial direction thereof. Further, such a rotary control member used for locking the distal end of an endoscope is often provided with a rotational-position control mechanism for making the rotary control member stop with a click at each of the lock and unlock positions thereof. Providing the endoscope with such a rotational-position control mechanism together with the aforementioned retaining mechanism tends to complicate the mechanical structure of the endoscope around the rotary control member thereof.

The aforementioned retaining mechanism is known in the art in the form of a mechanism having a retaining ring which is fitted in an annular groove formed around one end of the control center shaft. In this retaining mechanism, although there is play between the retaining ring and the control center shaft in radial directions perpendicular to the axial direction of the control center shaft, the control center shaft preferably does not rattle due to the play with the retaining ring being engaged with the control center shaft in place. This is true not only for the steering device for steering the distal end of an endoscope but also for any other similar steering devices having a rotary control member corresponding to the aforementioned rotary control member in mechanical apparatuses other than endoscopic apparatuses.

The aforementioned friction pad provided on the lock knob of the locking device is known in the art in the form of a doughnut-shaped disk pad 114' made of cork or rubber such as shown in FIG. 33. The disk pad 114' having such a doughnut shape is not easily deformed by external forces applied thereto. Namely, the doughnut shape resists crushing and thus provides stability to the shape of the disk pad 114'. Due to such characteristics of the disk pad 114', in the locking device using the disk pad 114', the amount of movement of the disk pad 114' is generally small in the axial direction of the aforementioned rotational shaft between a point at which the disk pad 114' is barely in contact with the aforementioned friction pad provided on the angle knob side and another point at which the disk pad 114' comes in pressing contact firmly with the friction pad to generate a sufficient friction resistance between the disk pad and the friction pad to lock the associated angle knob. Furthermore, this locking operation using the lock knob tends to require great force for turning the lock knob manually.

Therefore, when the lock knob is turned manually, the locking force varies significantly even if the amount of rotation of the lock knob is small, so that a fine adjustment of the locking force is required. Namely, a fine adjustment of the size of a gap between the friction element fixed relative to the lock knob and the friction pad fixed relative to the angle knob is required. Accordingly, it is necessary to adjust the locking force.

However, conventionally, in order to adjust the locking force, the steering device of the endoscope needs to be disassembled, which is troublesome and time-consuming. Moreover, the steerable distal end of the endoscope cannot be half-locked easily so that the distal end which is bent and locked is unlocked in accordance with the degree of an external force applied to the distal end of the endoscope.

SUMMARY OF THE INVENTION

It is an object of the present invention to provide a control device having a steering device for steering the distal end of an endoscope and a locking device for locking the steering device to lock the distal end of the endoscope, wherein the curved shape of the distal end of the endoscope does not change by the operation of a lock knob of the locking device.

It is another object of the present invention to provide a control device having a steering device for steering the distal end of an endoscope and a locking device for locking the steering device to lock the distal end of the endoscope, wherein the distal end of the endoscope bends in two directions perpendicular to each other by operating two angle knobs of the steering device, respectively, and wherein the operational force given to one of the two angle knobs does not exert any adverse effect on the operability of the other angle knob.

It is another object of the present invention to provide a steering device which is provided with a rotary control member (e.g., a knob, lever or similar element) fitted on a shaft and held rotatably about the shaft, wherein the steering device is provided with a simple retaining mechanism for preventing the rotary control member from coming off the shaft, and at the same time, a simple rotational-position control mechanism for making the rotary control member stop with a click at each of the lock and unlock positions thereof.

It is a further object of the present invention to provide a manually rotating device (steering device) which is provided with a rotary control member (e.g., a knob, lever or similar element) fitted on a shaft and held rotatably about the shaft, wherein a retaining ring of the aforementioned retaining mechanism can be held stably relative to the control center shaft with a simple structure.

It is a further object of the present invention to provide a control device having a steering device for steering the distal end of an endoscope and a locking device for locking the steering device to lock the distal end of the endoscope, wherein the locking force by the locking device can be finely adjusted easily without the need of disassembling the steering device.

It is another object of the present invention to provide a control device having a steering device for steering the distal end of an endoscope and a locking device for locking the steering device to lock the distal end of the endoscope, wherein the locking force by the locking device does not have to be adjusted, and at the same time, the distal end of the endoscope can be half-locked easily with the locking device in an easy and quick manner.

Other objects of the invention will become apparent to one skilled in the art in the following disclosure and the appended claims.

To achieve the object mentioned above, according to an aspect of the present invention, an endoscope having an elongated insertion portion provided at a distal end thereof with a steerable bendable portion is provide, the endoscope including at least one steering member which is rotated to bend the steerable bendable portion; at least one locking member which is rotated to lock the steering member, the steering member and the locking member being rotated about a common axis; and at least one axially-movable lock member which moves relative to the steering member along the common axis without rotating about the common axis to lock and unlock the steering member when the locking member is turned in a first rotational direction and a second rotational direction, respectively.

Preferably, the endoscope further includes a rotational shaft which supports the locking member in a rotatable manner about an axis of the rotational shaft; and a non-cylindrical portion having a non-circular cross section which is formed on the rotational shaft. The axially-movable lock member is positioned around the non-cylindrical portion in a manner so that the axially-movable lock member can move along the axis of the rotational shaft relative to the non-cylindrical portion without rotating about the axis of the rotational shaft.

In an embodiment, the endoscope further includes a drive force transmitting mechanism via which the axially-movable lock member moves along the axis of the rotational shaft in accordance with rotation of the locking member.

In an embodiment, the endoscope further includes a removable retaining member which is fitted on the non-cylindrical portion in a direction perpendicular to the axis of the rotational shaft. The removable retaining member is prohibited from moving along and rotating about the axis of the rotational shaft relative to the non-cylindrical portion in a state where the removable retaining member is fitted on the non-cylindrical portion. The removable retaining member is engaged with the axially-movable lock member to prohibit the axially-movable lock member from rotating about the axis of the rotational shaft relative to the non-cylindrical portion.

In an embodiment, the endoscope further includes a guide portion, formed on the axially-movable lock member, for preventing the removable retaining member from coming out of the non-cylindrical portion in a state where the guide portion is fitted on the removable retaining member, wherein the guide portion is fitted on the removable retaining member so that the guide portion is movable in a direction of the axis of the rotational shaft without rotating about the axis of the rotational shaft relative to the removable retaining member.

Preferably, the steering member includes a steering knob which is mounted around the rotational shaft, and the non-cylindrical portion is formed on the rotational shaft in an inner space of the steering knob.

In an embodiment, the steering member includes a first steering member which is rotated to bend the steerable bendable portion in a first bending direction; and a second steering member which is rotated to bend the steerable bendable portion in a second bending direction, the first steering member and the second steering member being rotated about the common axis. The locking member includes a first locking member which is rotated to lock the first steering member; and a second locking member which is rotated to lock the second steering member, the first locking member and the second locking member being rotated about the common axis. The axially-movable lock member includes a first axially-movable lock member which moves relative to the first steering member along the common axis without rotating about the common axis to lock and unlock the first steering member when the first locking member is turned in the first rotational direction and the second rotational direction, respectively; and a second axially-movable lock member which moves relative to the second steering member along the common axis without rotating about the common axis to lock and unlock the second steering member when the second locking member is turned in the first rotational direction and the second rotational direction, respectively.

In an embodiment, the endoscope further includes an inner body shaft which is fixed to a body of the endoscope; and an outer cylindrical body which is coaxially provided around the inner body shaft. The first axially-movable lock member is mounted to the to inner body shaft to be movable along an axis of the inner body shaft without rotating about the inner body shaft. The second axially-movable lock member is mounted to the outer cylindrical body to be movable along an axis of the outer cylindrical body without rotating about the outer cylindrical body.

In an embodiment, the first steering member includes a first cylindrical shaft, and the second steering member includes a second cylindrical member which is coaxially fitted on the first cylindrical shaft. The first cylindrical shaft and the second cylindrical member are fitted in a cylindrical space which is provided between the inner body shaft and the outer cylindrical body in a radial direction thereof, the first cylindrical shaft and the second cylindrical member being rotatable relative to each other about the axis of the inner body shaft.

In an embodiment, the first locking member is mounted to the inner body shaft to be rotatable about the axis of the inner body shaft, and the second locking member is mounted to the outer cylindrical body to be rotatable about the axis of the outer cylindrical body.

In an embodiment, the drive force transmitting mechanism includes male and female threads which mesh with each other, the male and female threads being formed on the locking member and the axially-movable lock member, respectively.

In an embodiment, the endoscope further includes at least one axially-immovable lock member which is fixed to the steering member. The axially-movable lock member moves toward the axially-immovable lock member to lock the steering member when the locking member is turned in the first rotational direction.

In an embodiment, the endoscope further includes a first friction pad fixed to the axially-movable lock member; and a second friction pad fixed to the axially-immovable lock member. The axially-movable lock member moves toward the axially-immovable lock member to bring the first friction pad into pressing contact with the second friction pad to thereby lock the steering member when the locking member is turned in the first rotational direction.

In an embodiment, the endoscope further includes an adjusting device for adjusting a position of the axially-immovable lock member relative to the steering member in a direction of the common axis.

According to another aspect of the present invention, an endoscope having an elongated insertion portion provided at a distal end thereof with a steerable bendable portion is provided, the endoscope including at least one control knob which is manually turned about an axis to bend the steerable bendable portion so as to direct the tip of the steerable bendable portion toward a target part; at least one lock knob which is manually turned about the axis to lock the control knob; and at least one axially-movable lock member which moves relative to the control knob along the axis without rotating about the axis to lock and unlock the control knob when the lock knob is turned in a first rotational direction and a second rotational direction, respectively.

According to another aspect of the present invention, an endoscope having an elongated insertion portion provided at a distal end thereof with a steerable bendable portion is provided, the endoscope including a first steering portion which is rotated to bend the bendable portion in a first bending direction; second steering portion which is rotated to bend the bendable portion in a second bending direction, the first steering portion and the second steering portion being rotated about a common axis; a first axially-movable lock member which moves along the common axis to bias the first steering portion in a first direction away from the second steering portion to lock the first steering portion; and a second axially-movable lock member which moves along the common axis to bias the second steering portion in a second direction away from the first steering portion to lock the second steering portion.

Preferably, the first axially-movable lock member and the second axially-movable lock member move away from each other to bias the first steering portion and the second steering portion, respectively, to lock the first steering portion and the second steering portion, respectively.

In an embodiment, the endoscope further includes a first locking portion which is rotated about the common axis to move the first axially-movable lock member along the common axis toward and away from the first steering portion when the first locking portion is turned in forward and reverse rotational directions thereof; and a second locking portion which is rotated about the common axis to move the second axially-movable lock member along the common axis toward and away from the second steering portion when the second locking portion is turned in forward and reverse rotational directions thereof.

In an embodiment, the first locking portion is engaged with the first axially-movable lock member via first screw threads so that the first axially-movable lock member moves along the common axis, due to an engagement of the first screw threads, when the first locking portion is turned. The second locking portion is engaged with the second axially-movable lock member via second screw threads so that the second axially-movable lock member moves along the common axis, due to an engagement of the second screw threads, when the second locking portion is turned.

Preferably, each of the first axially-movable lock member and the second axially-movable lock member moves along the common axis without rotating about the common axis.

According to another aspect of the present invention, an endoscope having an elongated insertion portion provided at a distal end thereof with a steerable bendable portion is provided, the endoscope including a first steering portion which can be rotated independently to bend the steerable bendable portion in a first bending direction; and a second steering portion which can be rotated independently to bend the steerable bendable portion in a second bending direction, the first steering portion and second steering portion being rotated about a common shaft; at least one axially-movable lock member which moves along an axis of the common shaft toward and away from one of the first steering portion and the second steering portion to one of lock and unlock the one of the first steering portion and the second steering portion. The axially-movable lock member moves along the axis to bias the one of the first steering portion and the second steering portion in a direction away from the other of the first steering portion and the second steering portion when locking the one of the first steering portion and the second steering portion.

In an embodiment, the axially-movable lock member includes a first axially-movable lock member which moves along the axis to bias the first steering portion in a first direction away from the second steering portion to lock the first steering portion; and a second axially-movable lock member which moves along the axis to bias the second steering portion in a second direction away from the first steering portion to lock the second steering portion.

According to another aspect of the present invention, an endoscope having an elongated insertion portion provided at a distal end thereof with a steerable bendable portion is provided, the endoscope including a steering member which is rotated about a shaft to bend the bendable portion; a locking member which is rotated about the shaft to lock the steering member; and a retaining member which is fixed to an end of the shaft to prevent the locking member from coming out of the shaft from the end thereof; and a spring which rotates together with the locking member when the locking member is turned. The locking member includes an engaging portion, wherein the retaining member includes at least one stop portion and at least one stop recess. The spring is engaged with the stop recess with a click when the engaging portion abuts against the stop portion.

In an embodiment, the stop portion and the stop recess are positioned substantially on opposite sides of the shaft in a radial direction thereof.

In an embodiment, the stop portion and the stop recess include two stop portions and two stop recesses, respectively.

In an embodiment, the two stop portions and the two stop recesses are formed on the retaining member at different circumferential positions thereof. One of the two stop portions and one of the two stop recesses are positioned substantially on opposite sides of the shaft in a first radial direction thereof. The other of the two stop portions and the other of the two stop recesses are positioned substantially on opposite sides of the shaft in a second radial direction thereof.

In an embodiment, the spring elastically presses the retaining member in a direction toward an axis of the shaft.

In an embodiment, a non-circular hole is formed on the retaining member, and the end of the shaft is formed to have a cross sectional shape corresponding to the shape of the non-circular hole so that the retaining member can be fitted on the end of the shaft.

In an embodiment, the retaining member is fixed to the end of the shaft via a set screw which is screwed into the end of the shaft to prevent the retaining member from coming out of the end of the shaft.

According to another aspect of the present invention, an endoscope having an elongated insertion portion provided at a distal end thereof with a steerable bendable portion is provided, the endoscope including a steering member which is rotated about a shaft to bend the bendable portion; a locking member which is rotated about the shaft to lock the steering member; a retaining member fixed to an end of the shaft to prevent the locking member from coming out of the shaft from the end thereof; a projection which projects from the locking member; a spring which is fixed to the locking member so that part of the spring elastically presses the retaining member in a direction toward the projection. Part of the spring and the projection are positioned substantially on opposite sides of the shaft in a radial direction thereof. The retaining member includes at least one stop face and at least one stop recess. Part of the spring is engaged with the stop recess with a click when the projection abuts against the stop face.

In an embodiment, the stop face and the stop recess include two stop faces and two stop recesses, respectively.

In an embodiment, the two stop faces and the two stop recesses are formed on the retaining member at different circumferential positions thereof. One of the two stop faces and one of the two stop recesses are positioned substantially on opposite sides of the shaft in a first radial direction thereof. The other of the two stop faces and the other of the two stop recesses are positioned substantially on opposite sides of the shaft in a second radial direction thereof.

According to another aspect of the present invention, a manually rotating device is provided, including a shaft; a manual operation member which is mounted to the shaft to be turned manually about the shaft; a retaining member fixed to an end of the shaft to prevent the manual operation member from coming out of the shaft from the end thereof; and a spring which is associated with the retaining member, wherein the spring rotates together with the manual operation member when the manual operation member is turned. The manual operation member includes an engaging portion, the retaining member includes at least one stop portion and at least one stop recess. The spring is engaged with the stop recess with a click when the engaging portion abuts against the stop portion.

In an embodiment, the stop portion and the stop recess are positioned substantially on opposite sides of the shaft in a radial direction thereof.

According to an aspect of the present invention, an endoscope having an elongated insertion portion provided at a distal end thereof with a steerable bendable portion is provided, the endoscope including a hollow steering knob which is manually turned about a shaft to bend the steerable bendable portion, an opening being formed on the steering knob; a first friction brake member which rotates together with the steering knob when the steering knob is turned; a lock operation member which can be manually turned relative to the steering knob; a second friction brake member which is driven to move toward and away from the first friction brake member to lock and unlock the steering knob in accordance with rotation of the lock operation member relative to the steering knob; and a locking force adjusting device for adjusting an initial space between the first friction brake member and the second friction brake member, the locking force adjusting device being accessible from the outside of the endoscope via the opening of the steering knob.

Preferably, the locking force adjusting device moves the first friction brake member relative to the steering knob to adjust the initial space in a direction of an axis of the shaft when the locking force adjusting device is operated via the opening.

In an embodiment, the locking force adjusting device includes first and second thread portions which mesh with each other, the first thread portion being positioned in the steering knob, the second thread portion being formed on the first friction brake member; an at least one engaging portion formed on the first friction brake member to be exposed to the opening. The first friction brake member moves in the direction of the axis of the shaft relative to the steering knob in accordance with the first and second thread portions when the first friction brake member is rotated relative to the steering knob with the at least one engaging portion.

In an embodiment, the steering knob is formed as a substantially hollow cylindrical shape, and is provided with an end face extending substantially perpendicular to the axis of the shaft. The opening is formed at the end face of the steering knob. The second friction brake member and the first friction brake member are positioned in the steering knob in the opening thereof so that an outer surface of each of the second friction brake member and the first friction brake member is substantially flush with the end face of the steering knob.

In an embodiment, the first friction brake member is mounted to the steering knob to be movable in the direction of the axis of the shaft and to be rotatable about the axis of the shaft together with the steering knob. The locking force adjusting device includes a first thread positioned in the steering knob; an adjusting ring having a second thread which meshes with the first thread; and at least one engaging portion formed on the adjusting ring to be exposed to the opening. The first friction brake member moves in the direction of the axis of the shaft relative to the steering knob if the adjusting ring is rotated relative to the steering knob with the engaging portion.

In an embodiment, the steering knob is formed as a substantially hollow cylindrical shape, and is provided with an end face extending substantially perpendicular to the axis of the shaft. The opening is formed on the end face of the steering knob. The second friction brake member and the first friction brake member are positioned in the steering knob in the opening thereof so that an outer surface of each of the second friction brake member, the first friction brake member and the adjusting ring is substantially flush with the end face of the steering knob.

Preferably, the adjusting ring prevents the first friction brake member from moving out of the opening.

In an embodiment, the engaging portion includes at least one hole which is formed on the surface of the first friction brake member which is exposed to the opening.

In an embodiment, the engaging portion includes two holes which are formed on the surface of the first friction brake member, and two pins of a pin face wrench can be engaged in the two holes, respectively.

In an embodiment, the engaging portion includes at least one hole which is formed on that surface of the adjusting ring which is exposed to the opening.

In an embodiment, the engaging portion includes two holes which are formed on the surface of the adjusting ring, and two pins of a pin face wrench can be engaged in the at least two holes, respectively.

In an embodiment, the first friction brake member and the second friction brake member can be mounted to and dismounted from the steering knob via the opening.

In an embodiment, the lock operation member is positioned to face the opening of the steering knob, wherein the locking force adjusting device is accessible from the outside of the endoscope via a portion of the opening to which the lock operation member does not face.

According to another aspect of the present invention, an endoscope having an elongated insertion portion provided at a distal end thereof with a steerable bendable portion is provided, the endoscope including first and second hollow steering knobs which are manually turned independently of each other about a shaft to bend the bendable portion, wherein the first and second hollow steering knobs are positioned adjacent to each other in a direction of an axis of the shaft; a first opening formed on the first hollow steering knobs; a second opening formed on the second the two hollow steering knobs; a first friction brake member, provided for each of the first and second hollow steering knobs, which rotates together with associated one of the first and second hollow steering knobs when associated one of the first and second hollow steering knobs is turned; a lock operation member, provided for each of the first and second hollow steering knobs, which can be manually turned relative to associated one of the first and second hollow steering knobs; a second friction brake member, provided for each of the first and second hollow steering knobs, which is driven to move toward and away from associated the first friction brake member to lock and unlock associated one of the first and second hollow steering knobs in accordance with rotation of associated the lock operation member relative to the associated hollow steering knob; and a locking force adjusting device for adjusting an initial space between the first friction brake member and the second friction brake member for each of the first and second hollow steering knobs, the locking force adjusting device being accessible from the outside of the endoscope via associated one of the first and second openings. The first and the second openings are formed on the first and second hollow steering knobs to be open in opposite directions so as not to face each other.

According to another aspect of the present invention, an endoscope having an elongated insertion portion provided at a distal end thereof with a steerable bendable portion is provided, the endoscope including a steering device having a first operation member which is manually turned to bend the bendable portion so as to direct the tip of the bendable portion toward a target part; and a locking device having a second operation member which is manually turned to lock the steering device. A first friction member provided on the locking device comes into pressing contact with a second friction member provided on the steering device by an operation of the second operation member. The first friction member is shaped so as to facilitate compression thereof in a direction of the thickness of the first friction member.

In an embodiment, the first friction member includes a plurality of gaps for facilitating compression of the first friction member in the direction.

In an embodiment, the plurality of gaps are formed by a plurality of projections and depressions.

In an embodiment, the first friction member has a general cylindrical shape, and the plurality of projections and depressions extend across the first friction member in radial directions.

In an embodiment, the plurality of gaps includes a plurality of holes.

In an embodiment, the first friction member has a general cylindrical shape, and the plurality of holes extend across the first friction member in radial directions.

In an embodiment, the plurality of projections and depressions are arranged at equi-angular intervals about a center of the first friction member.

In an embodiment, the plurality of holes are arranged at equi-angular intervals about a center of the first friction member.

In an embodiment, the first friction member is formed in a disk shape so as to be compressed in a direction of the thickness of the first friction member easier than in a radial direction of the first friction member.

According to another aspect of the present invention, an endoscope having an elongated insertion portion provided at a distal end thereof with a steerable bendable portion is provided, the endoscope including a steering device having a first operation member which is manually turned about a shaft to bend the bendable portion so as to direct a tip of the bendable portion toward a target part; a locking device having a second operation member which is manually turned about the shaft to lock the steering device; a first friction member which is provided as an element of the locking device which is movable in a direction of an axis of the shaft and does not rotate about the axis; a second friction member which rotates together with the first operation member; and a cam mechanism, elements of which are provided on the second operation member and the first friction member. The first friction member is moved in the direction of the axis of the shaft to come into contact with the second friction member to restrict rotation of the first operation member via the cam mechanism.

In an embodiment, the locking device includes a rotational member which is provided integral with the second operation member; and an axially-movable lock member which is positioned to face the second friction member and is movable in the direction of the axis of the shaft without being rotatable about the axis, the first friction member being fixed to the axially-movable lock member. The cam mechanism includes at least one cam follower fixed to the rotational member; and at least one cam groove which is formed on the axially-movable lock member and in which the cam follower is engaged. Turning the second operation member causes the axially-movable lock member to move in the direction of the axis of the shaft via an engagement of the cam follower and the cam groove so that the first friction member comes into contact with the second friction member to restrict rotation of the first operation member.

In an embodiment, the cam groove includes an inclined groove portion which is inclined with respect to a plane which is perpendicular to the axis of the shaft.

In an embodiment, the axially-movable lock member includes at least one leaf spring portion which can elastically bend with respect to the axially-movable lock member, and an under surface of the leaf spring portion constitutes a part of a cam surface of the cam groove.

Preferably, the leaf spring portion of axially-movable lock member includes a slit, wherein the cam groove connects with an external portion of the axially-movable lock member via the slit.

Preferably, at least one end of the cam groove is formed to be wider than a middle portion of the cam groove.

Preferably, each of opposite ends of the cam groove is formed to have a substantially circular cross section, and a diameter of each of the opposite ends of the cam groove is slightly greater than a diameter of the cam follower.

The present disclosure relates to subject matter contained in the following six Japanese Patent Applications No.2000-117658 (filed on Apr. 19, 2000), No.2000-121994 (filed on Apr. 24, 2000), No.2000-132203 (filed on May 1, 2000), No.2000-170907 (filed on Jun. 7, 2000), No.2000-229088 (filed on Jul. 28, 2000) and No.2000-229089 (filed on Jul. 28, 2000) which are expressly incorporated herein by reference in their entireties.

BRIEF DESCRIPTION OF THE DRAWINGS

The present invention will be described below in detail with reference to the accompanying drawings in which.

DESCRIPTION OF THE PREFERRED EMBODIMENTS

Figure 30:
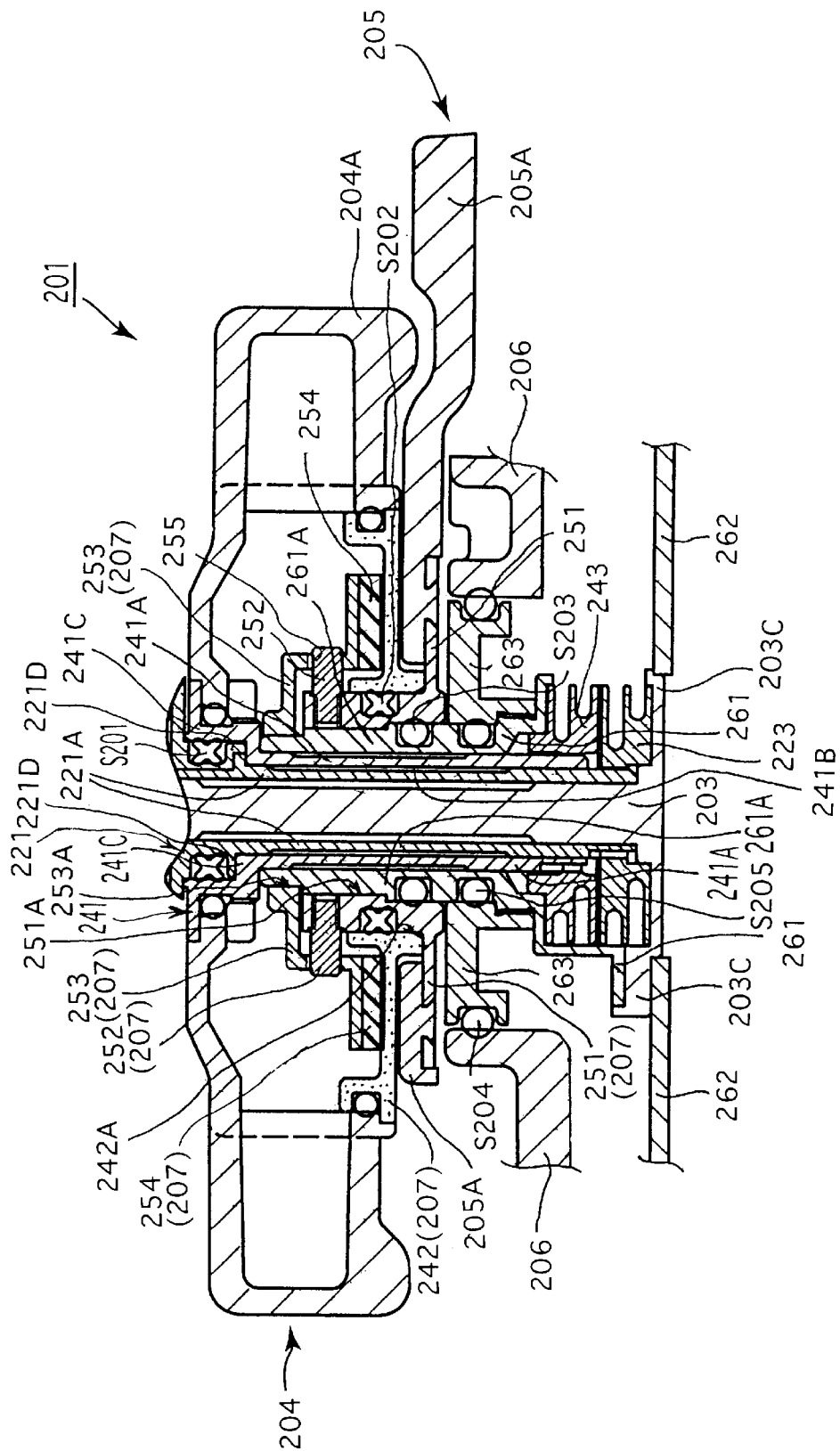
FIG. 30 is a cross sectional view of a lower half of the third embodiment of the control device of the endoscope, showing fundamental elements thereof.
Figure 31:
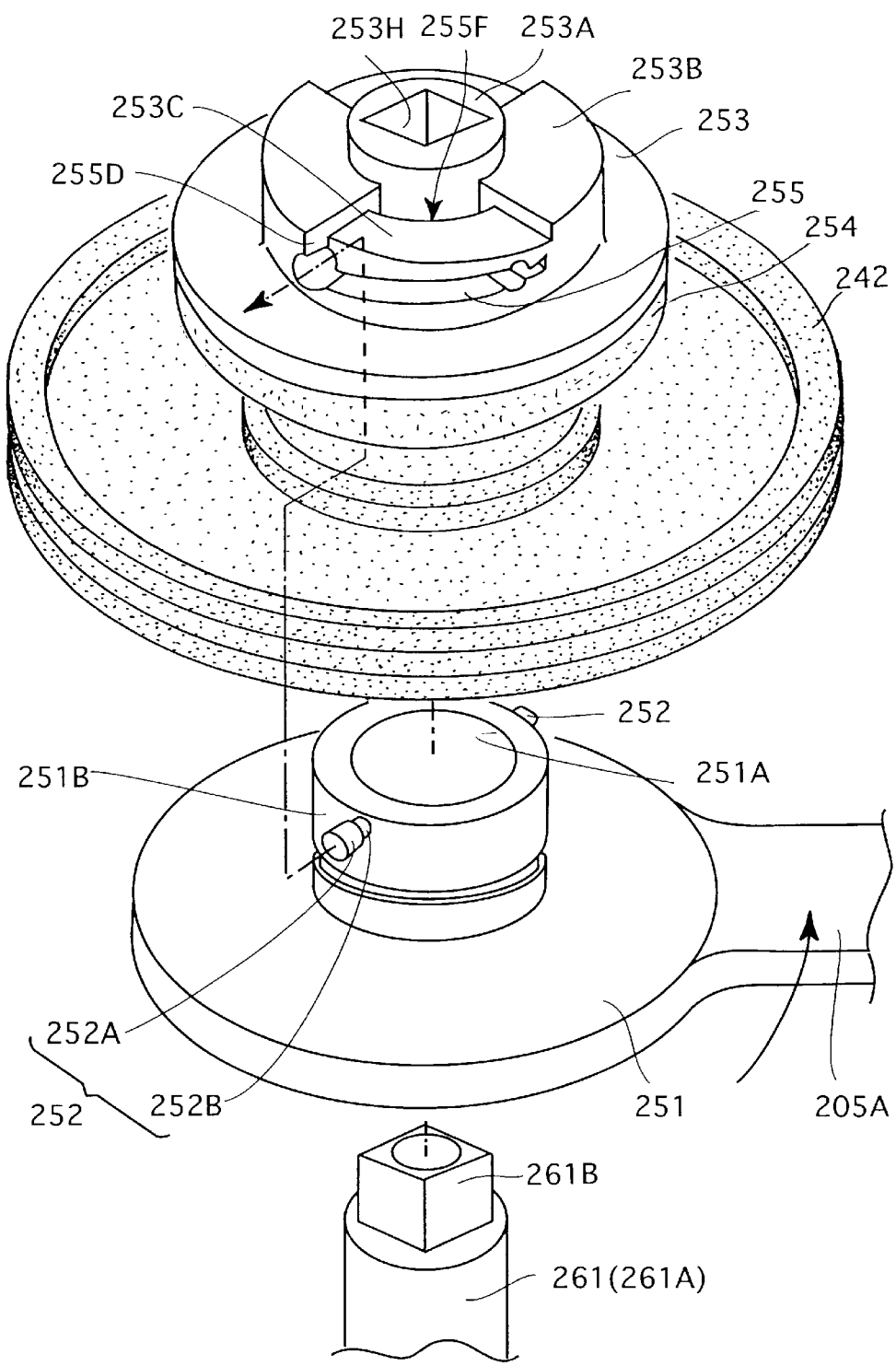
FIG. 31 is a perspective view of fundamental elements of a locking device for the U-D steering device of the control device shown in FIG. 30.
Figure 32:
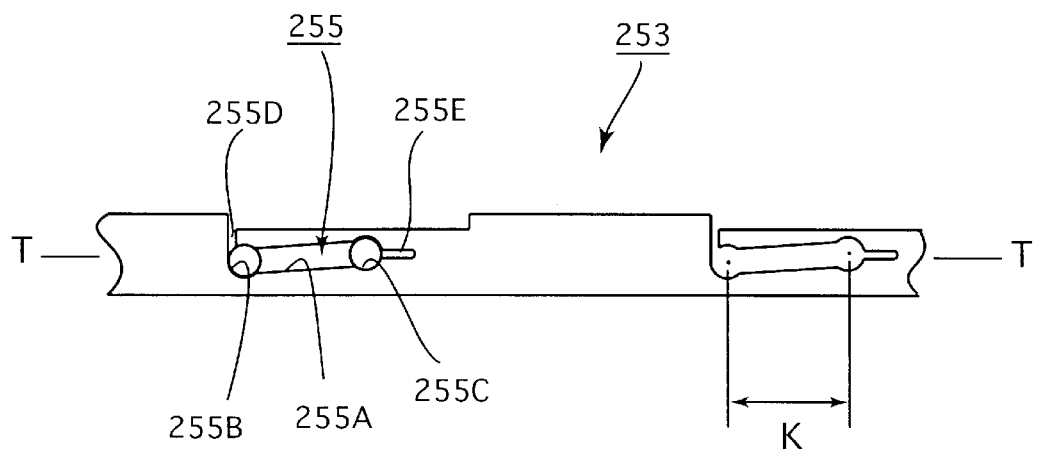
FIG. 32 is a developed view of the outer peripheral surface of an axially-movable lock member shown in FIG. 31, showing the shape of each cam groove formed on the axially-movable lock member.

FIGS. 1 through 20 show the first embodiment of a control device of an endoscope 10. FIGS. 21 through 29 show the second embodiment of the control device of the endoscope 10. FIGS. 30 through 32 show the third embodiment of the control device of the endoscope 10.

Figure 1:
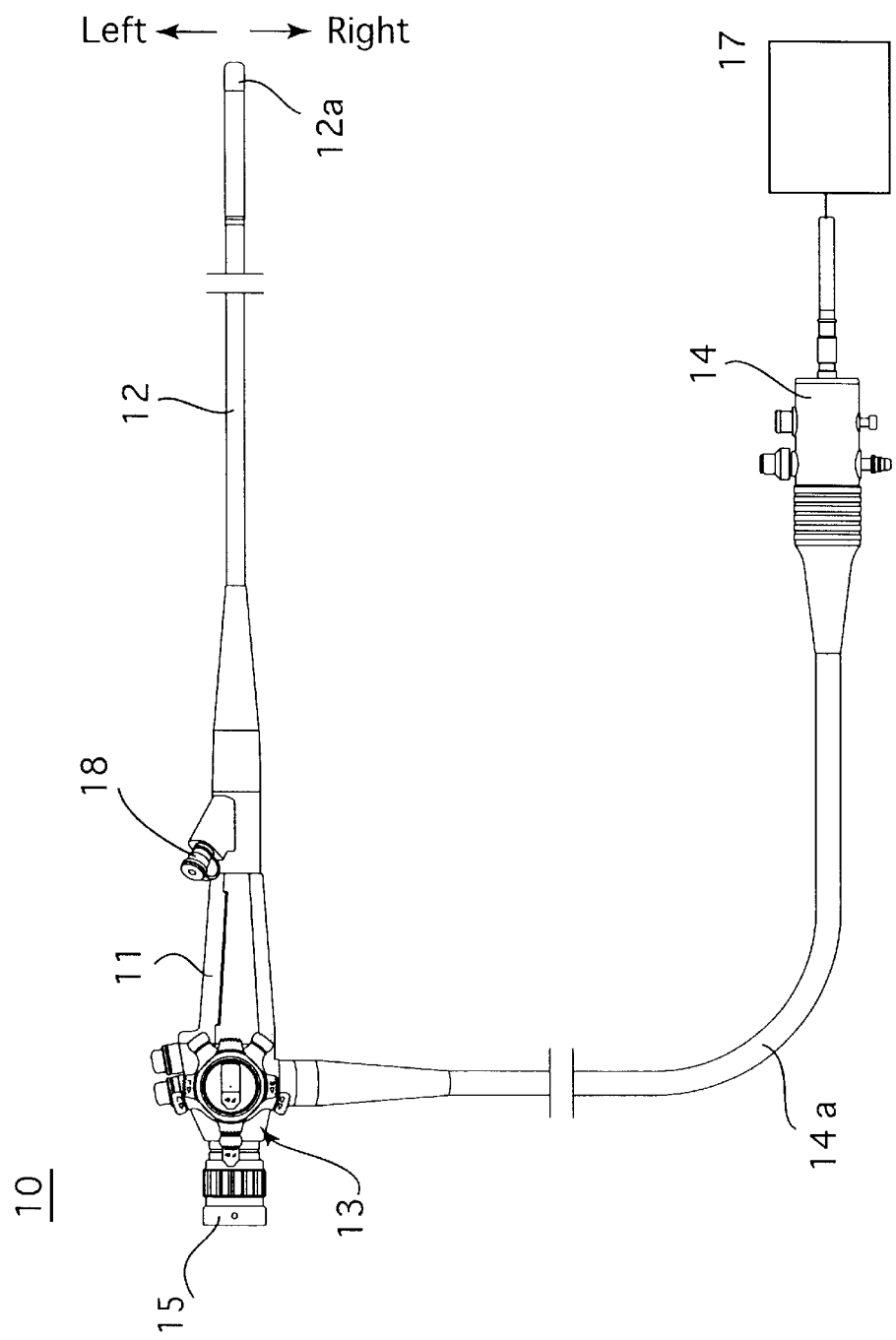
FIG. 1 is an external view of an endoscope having the first embodiment of a control device to which the present invention is applied, showing the overall structure of the endoscope.

The endoscope 10 shown in FIG. 1 is a medical device. The endoscope 10 is provided with a control body 11 and an insertion portion 12 connected to the control body 11. The distal end of the insertion portion 12 is formed as a steerable bendable portion 12a which can be steered to bend right, left, upward and downward by controlling a steering device 13 provided on the control body 11. The bendable portion 12a is provided at the tip thereof with an objective lens portion (not shown) and a light guide portion (not shown). Images of the object to be viewed via the objective lens portion are viewed through an eyepiece portion 15 provided at the rear end (the left end as viewed in FIG. 1) of the control body 11.

Illumination light for illuminating a target part is emitted from a lighting device 17 connected to a connector 14 of the endoscope 10 to the light guide portion provided at the tip of the bendable portion via a light-guide flexible tube 14a. The endoscope 10 is provided between the control body 11 and the insertion portion 12 with a treatment tool insertion opening 18. The tip of a treatment tool (not shown) inserted into a treatment tool insertion channel in the insertion portion 12 via the treatment tool insertion opening 18 projects out of the tip of the treatment tool insertion channel at the tip of the bendable portion 12a.

Figure 2:
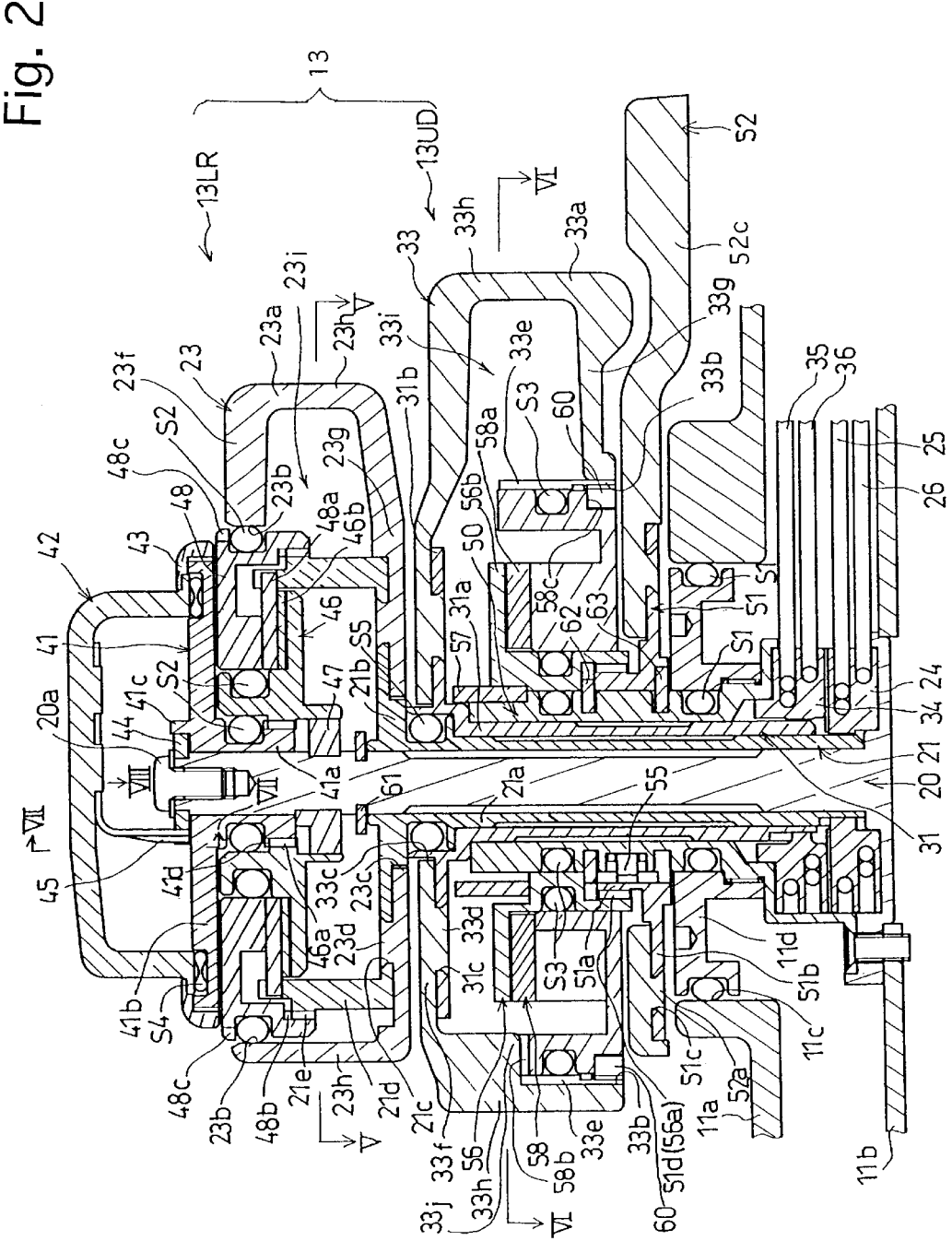
FIG. 2 is a cross sectional view of fundamental portion of the endoscope shown in FIG. 1, showing fundamental elements of the control device of the endoscope.
Figure 3:
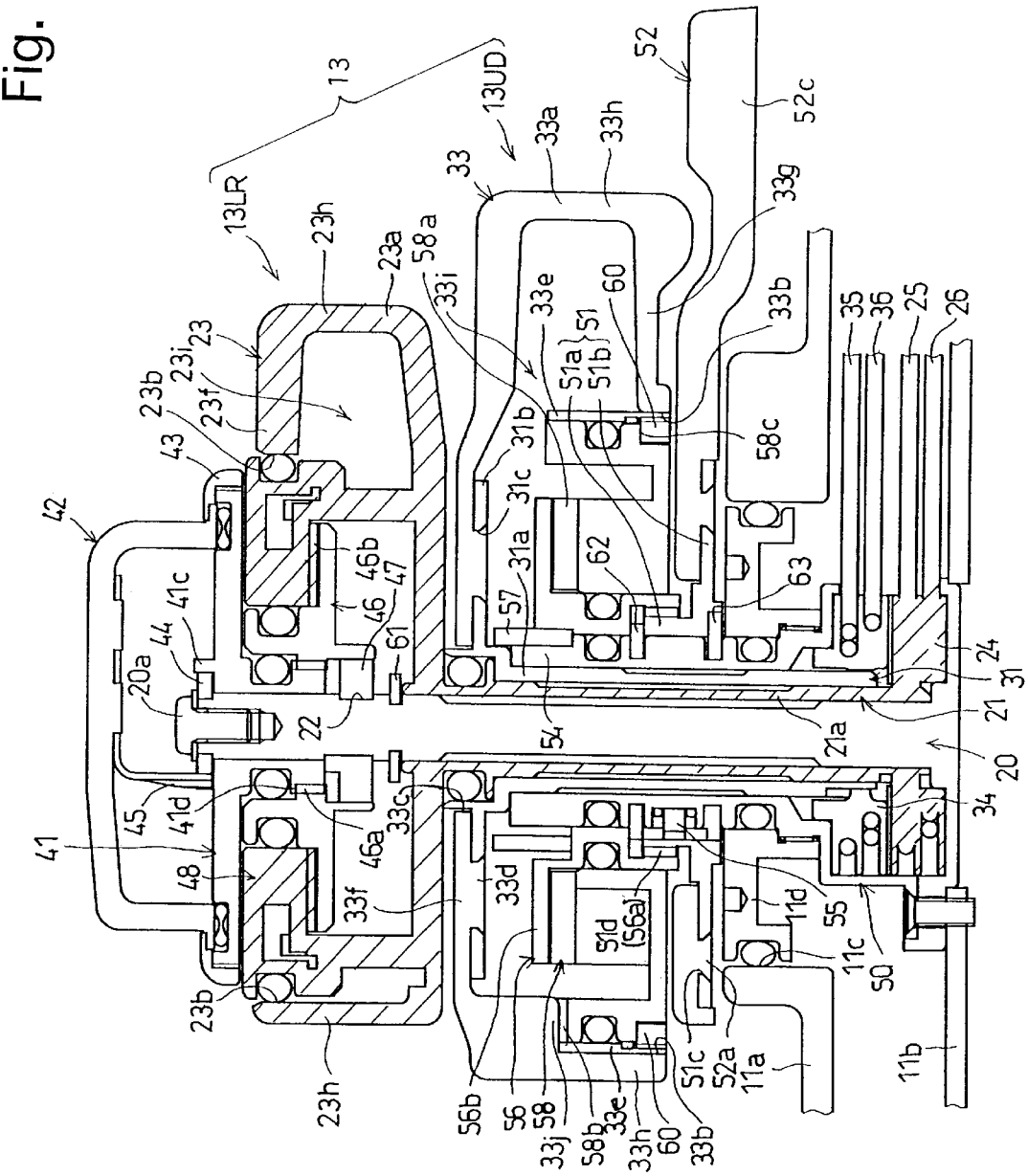
FIG. 3 is a view similar to FIG. 2 and illustrates elements of an L-R steering device which rotate together in the same rotational direction by the same angle of rotation as an integral element for the purpose of illustration.
Figure 4:
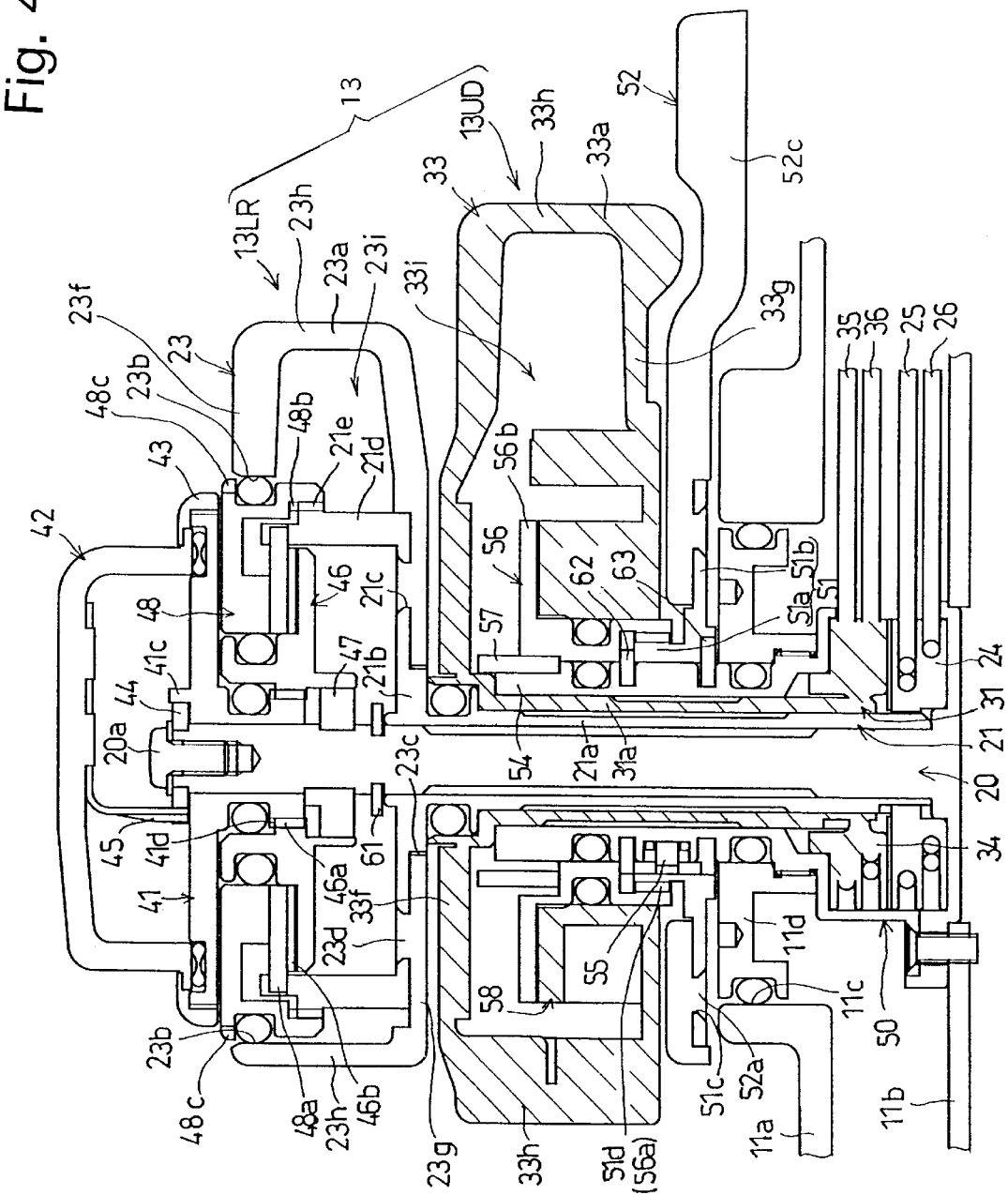
FIG. 4 is a view similar to FIG. 2 and illustrates elements of a U-D steering device which rotate together in the same rotational direction by the same angle of rotation as an integral element for the purpose of illustration.

FIG. 2 is a cross sectional view of a fundamental portion of the endoscope 10, showing the steering device 13 and peripheral elements in cross section. The steering device 13 is provided with an L-R steering device 13LR for bending the bendable portion 12a left and right and a U-D steering device 13UD for bending the bendable portion 12a upward and downward. In FIG. 3, elements of the L-R steering device 13LR which rotate together are illustrated as an integral element for the purpose of illustration. In FIG. 4, elements of the U-D steering device 13UD which rotate together are illustrated as an integral element for the purpose of illustration. In FIG. 3 only the elements of the L-R steering device 13LR which rotate together are hatched. Likewise, in FIG. 4 only the elements of the U-D steering device 13UD which rotate together are hatched. Firstly, the L-R steering device 13LR will be hereinafter discussed in detail.

The control body 11 is provided with a housing 11a to which a substrate 11b is positioned in and fixed. One end (the lower end as viewed in FIG. 2) of a rotational shaft (inner body shaft) 20 is fixed to the substrate 11b. The rotational shaft 20 extends upwards as viewed in FIG. 2 through a through hole 11c formed on the housing 11a. An annular gap between the rotational shaft 20 and the through hole 11c is closed by a covering member 11d positioned between a stationary hollow cylindrical base (outer cylindrical body) 50 and the housing 11a.

The L-R steering device 13LR is provided around the rotational shaft 20 with an inner control shaft 21 rotatably fitted on the rotational shaft 20. The inner control shaft 21 is made of metal and is provided with a cylindrical shaft portion 21a and a disk portion 21b. The cylindrical shaft portion 21a is coaxial to the rotational shaft 20 and fitted on the rotational shaft 20. The disk portion 21b is positioned at the upper end of the cylindrical shaft portion 21a. The disk portion 21b is provided with a plurality of circular holes 21c (see FIG. 5) at equi-angular intervals about an axis 20x of the rotational shaft 20. The disk portion 21b is provided around the outer edge thereof with an outer cylindrical portion 21d which extends upward from the outer edge of the disk portion 21b. The outer cylindrical portion 21d is provided on an outer peripheral surface thereof with a male thread 21e.

Figure 5:
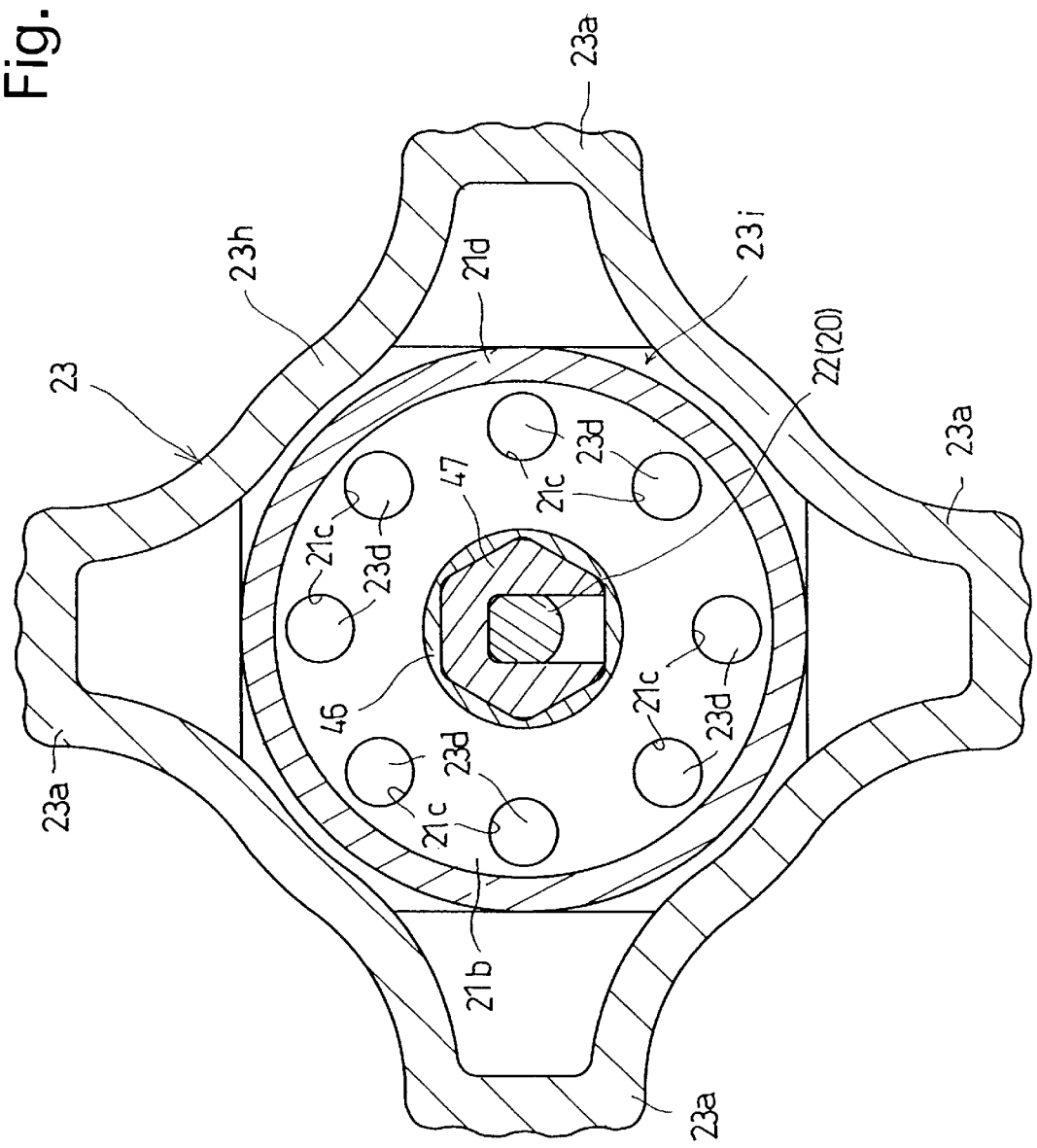
FIG. 5 is a cross sectional view of the first embodiment of the control device of the endoscope shown in FIG. 2, taken along V—V line in FIG. 2, viewed in the direction of the appended arrows.

The L-R steering device 13LR is provided with an L-R angle knob (L-R control knob) 23 that is made of a plastic. The L-R angle knob 23 is fixed to the inner control shaft 21. As can be seen in FIG. 5, the L-R angle knob 23 is provided at equi-angular intervals with four projecting portions 23a which extend radially outwards so that the operator can securely hold and turn the L-R angle knob 23 with his/her fingers engaging with the projecting portions 23a. The L-R angle knob 23 is formed as a hollow element as shown in FIGS. 2 through 4. The L-R angle knob 23 is provided on top and bottom portions thereof with an upper large circular aperture (opening) 23b and a lower small circular aperture 23c which have a large diameter and a small diameter, respectively. The disk portion 21b is fitted in the lower small aperture 23c. The L-R angle knob 23 is provided, on the bottom portion thereof in the vicinity of the lower small aperture 23c, with a plurality of projections 23d at equi-angular intervals about the axis of the rotational shaft 20. The plurality of projections 23d are firstly fitted in the plurality of circular holes 21c, respectively, and subsequently the tip of each projection 23d is melted by heat to fix the L-R angle knob 23 to the inner control shaft 21. Hence the L-R angle knob 23 and the inner control shaft 21 constitute a steering member.

The steering device 13 is provided at the inner end (the lower end as viewed in FIG. 2) of the inner control shaft 21 with a first pulley 24 that is fixed thereto. A first pair of control wires 25 and 26 are fixed to the first pulley 24. The control wire 25 is wound around the first pulley 24 while the control wire 26 is extended from the first pulley 24 toward the distal end of the flexible insertion portion 12 if the first pulley 24 rotates in one rotational direction, while the control wire 26 is wound around the first pulley 24 while the control wire 25 is extended from the first pulley 24 toward the distal end of the flexible insertion portion 12 if the first pulley 24 rotates in the other rotational direction. The first pair of control wires 25 and 26 have respective distal portions thereof anchored to joint rings (not shown) provided in the bendable portion 12a. Pulling and extending actions of the first pair of wires 25 and 26 cause the bendable portion 12a to bend right and left. In the present embodiment, the bendable portion 12a bends left by turning the L-R angle knob 23, which is fixed to the inner control shaft 21, counterclockwise as viewed in FIG. 10, while the bendable portion 12a bends right by turning the L-R angle knob 23 clockwise as viewed in FIG. 10.

The U-D steering device 13UD will be hereinafter discussed in detail. The U-D steering device 13UD is provided around the cylindrical shaft portion 21a of the inner control shaft 21 with an outer control shaft 31 rotatably fitted on the inner control shaft 21. The outer control shaft 31 is made of metal and is provided with a cylindrical shaft portion 31a and a disk portion 31b. The disk portion 31b is provided with a plurality of circular holes 31c at equi-angular intervals about the axis of the rotational shaft 20.

Figure 6:
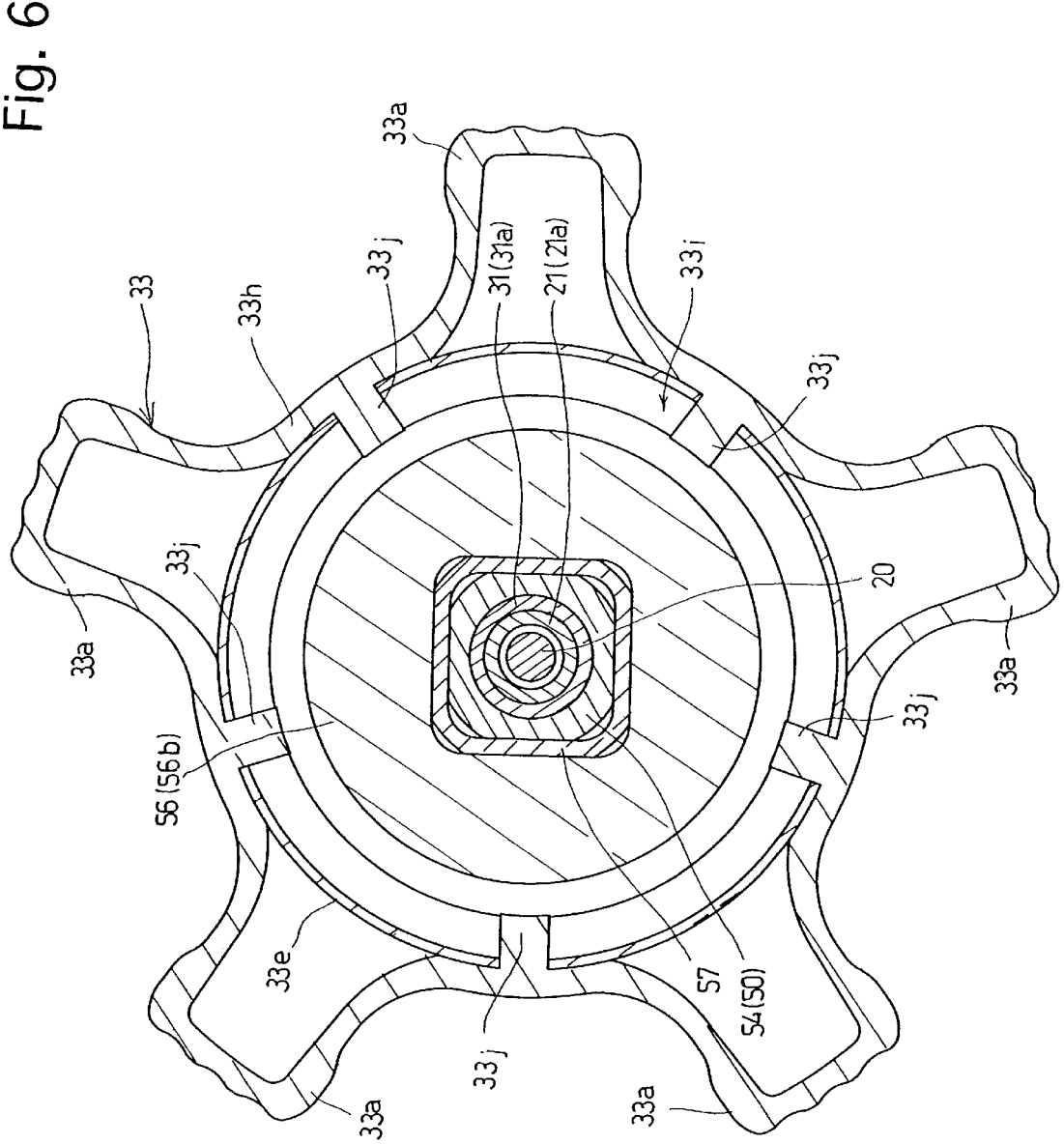
FIG. 6 is a cross sectional view of the first embodiment of the control device of the endoscope shown in FIG. 2, taken along VI—VI line in FIG. 2, viewed in the direction of the appended arrows.

The U-D steering device 13UD is provided with a U-D angle knob (U-D control knob/steering knob) 33 that is made of a plastic. The U-D angle knob 33 is fixed to the outer control shaft 31. As can be seen in FIG. 6, the U-D angle knob 33 is provided at equi-angular intervals with five projecting portions 33a which extend radially outwards so that the operator can securely hold and turn the U-D angle knob 33 with his/her fingers engaging with the projecting portions 33a. The U-D angle knob 33 is formed as a hollow element as shown in FIGS. 2 through 4. The U-D angle knob 33 is provided on top and bottom portions thereof with an upper small circular aperture 33c and a lower large circular aperture (opening) 33b which have a small diameter and a large diameter, respectively. Part of the disk portion 31b is fitted in the upper small aperture 33c. The U-D angle knob 33 is provided, on the upper portion thereof in the vicinity of the upper small aperture 33c, with a plurality of projections 33d at equi-angular intervals about the axis of the rotational shaft 20. The plurality of projections 33d are firstly fitted in the plurality of circular holes 31c, respectively, and subsequently the tip of each projection 33d is melted by heat to fix the U-D angle knob 33 to the outer control shaft 31. Hence the U-D angle knob 33 and the outer control shaft 31 constitute a steering member. A metal ring 33e having a female thread formed on an inner peripheral surface thereof is positioned in the U-D angle knob 33 in the lower large aperture 33b and is fixed to the U-D angle knob 33.

The steering device 13 is provided at the inner end (the lower end as viewed in FIG. 2) of the outer control shaft 31 with a second pulley 34 that is fixed thereto. A second pair of control wires 35 and 36 are fixed to the second pulley 34. The control wire 35 is wound around the second pulley 34 while the control wire 36 is extended from the second pulley 34 toward the distal end of the flexible insertion portion 12 if the second pulley 34 rotates in one rotational direction, while the control wire 36 is wound around the second pulley 34 while the control wire 35 is extended from the second pulley 34 toward the distal end of the flexible insertion portion 12 if the second pulley 34 rotates in the other rotational direction. The second pair of control wires 35 and 36 have respective distal portions thereof anchored to the aforementioned joint rings (not shown) provided in the bendable portion 12a. Pulling and extending actions of the second pair of wires 35 and 36 cause the bendable portion 12a to bend upward and downward. In the present embodiment, the bendable portion 12a bends upward by turning the U-D angle knob 33, which is fixed to the outer control shaft 31, counterclockwise as viewed in FIG. 10, while the bendable portion 12a bends downward by turning the U-D angle knob 33 clockwise as viewed in FIG. 10.

Each of the L-R angle knob 23 and the U-D angle knob 33 is locked with a corresponding locking device to fix the bendable portion 12a to a desired curved shape, i.e., to fix the orientation of the tip of the bendable portion 12a. Firstly, the locking device for the L-R steering device 13LR will be hereinafter discussed in detail.

Figure 9:
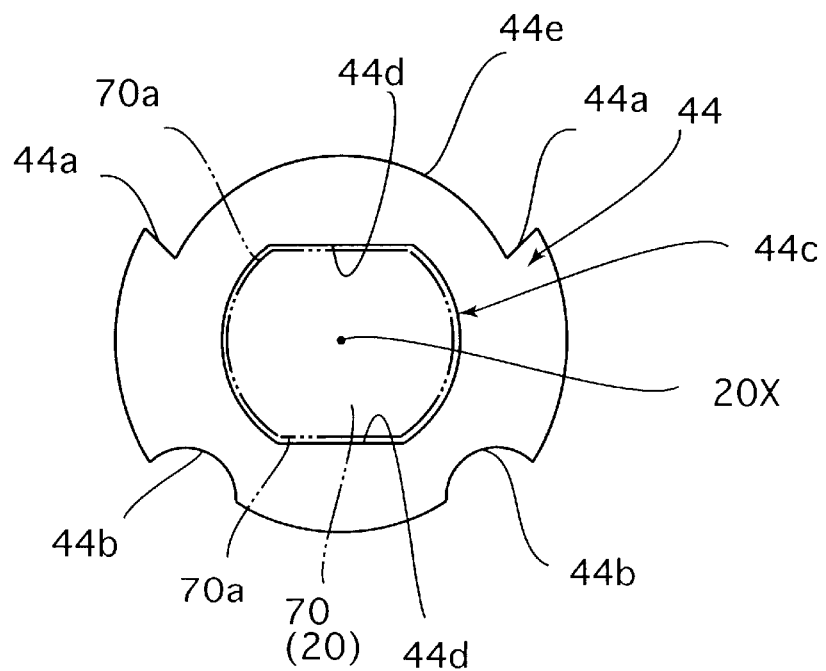
FIG. 9 is a plan view of the retaining ring shown in FIG. 8.

A first rotating member 41 which includes a cylindrical portion 41a and a disk portion 41b is fixed at the upper end of the rotational shaft 20. The cylindrical portion 41a is fitted on the upper end of the rotational shaft 20 to be rotatable relative to the rotational shaft 20, so that the rotational member 41 is rotatable about the rotational shaft 20. An L-R lock knob 42 is fixedly mounted onto the disk portion 41b via a fixing ring 43. The fixing ring 43 is provided on an inner peripheral surface thereof with a female thread, while the outer edge of the disk portion 41b is provided with a male thread which can be engaged with the female thread of the fixing ring 43. The fixing ring 43 is fixed to the disk portion 41b via the male and female threads to fix the L-R lock knob 42 to the rotational member 41, hence constituting a locking member (first locking member). Accordingly, the first rotating member 41 rotates together with the L-R lock knob 42 when the L-R lock knob 42 is turned manually. A retaining ring 44 for preventing the rotational member 41 and the L-R lock knob 42 that is integral with the rotational member 41 from coming off the rotational shaft 20 is fixed at the upper end of the rotational shaft 20. As shown in FIG. 9, the retaining ring 44 is provided at the center thereof with a noncircular hole 44c, while the upper end of the rotational shaft 20 is formed to have a cross sectional shape which corresponds to the shape of the non-circular hole 44c. Due to this structure, the retaining ring 44 is fitted on the upper end of the rotational shaft 20 while being prohibited from rotating about the axis 20x of the rotational shaft 20 relative to the rotational shaft 20. The retaining ring 44 is secured to the upper end of the rotational shaft 20 via a set screw 20a that is screwed into the upper end of the rotational shaft 20. Accordingly, the set screw 20a prevents the retaining ring 44 from coming off the upper end of the rotational shaft 20.

Figure 7:
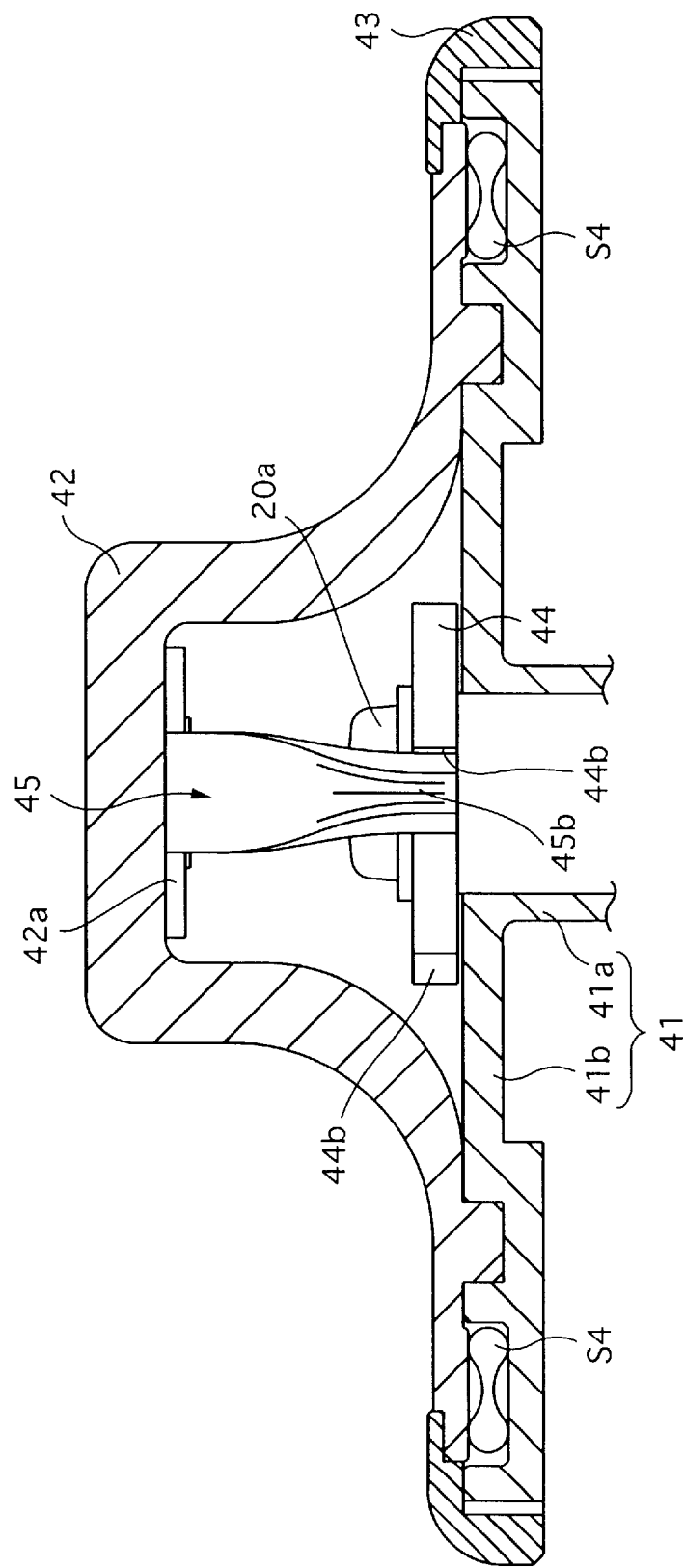
FIG. 7 is a cross sectional view of the first embodiment of the control device of the endoscope shown in FIG. 2, taken along VII—VII line in FIG. 2, viewed in the direction of the appended arrows.
Figure 8:
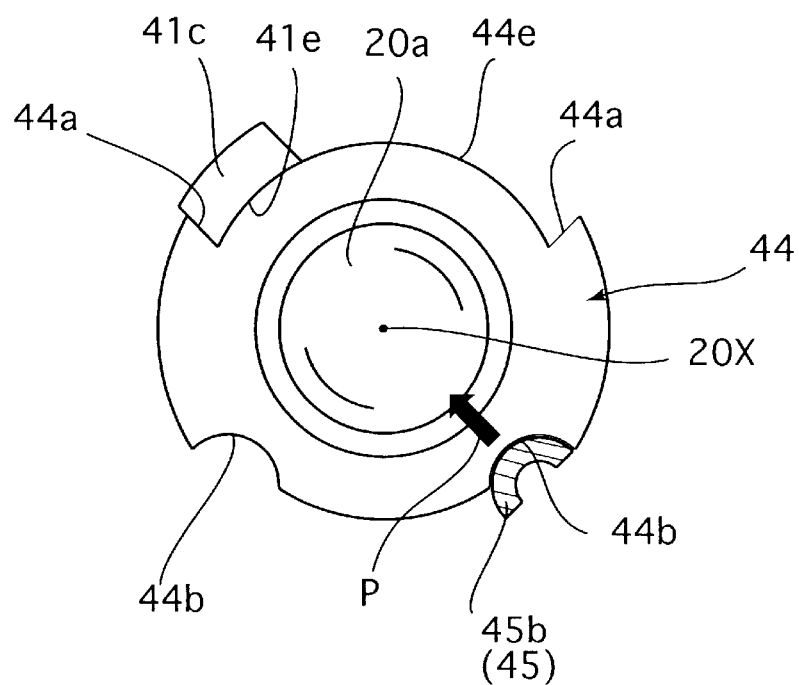
FIG. 8 is a plan view of part of the first embodiment of the control device of the endoscope shown in FIG. 2, showing a retaining ring, a set screw and other peripheral elements, viewed in the direction of an arrow VIII shown in FIG. 8.

As can be understood from FIGS. 7 through 9, the first rotating member 41 and the L-R lock knob 42, which is integral therewith, can rotate within a predetermined range of rotation which is defined by a projection 41c projected from the disk portion 41b and two stop faces 44a formed on the retaining ring 44 at different circumferential positions thereof. The projection 41c abuts against one of the two stop faces 44a when the first rotating member 41 rotates to one end of the predetermined range thereof, while the projection 41c abuts against the other stop face 44a when the first rotating member 41 rotates to the other end of the predetermined range thereof. Accordingly, the predetermined range corresponds to a movable range of the projection 41c between the two stop faces 44a. The retaining ring 44 is further provided with two stop recesses 44b which are positioned substantially on the opposite sides from the two stop faces 44a with respect to the axis 20x of the rotational shaft 20 in radial directions thereof respectively. An engaging spring 45 (see FIGS. 7, 8 and 12) which is fixed to the L-R lock knob 42 engages with a stop recess 44b with a click when the projection 41c abuts against a stop face 44a, the two stop faces 44a determining two stop positions of the integral member which includes the first rotating member 41 and the L-R lock knob 42, respectively.

The cylindrical portion 41a of the first rotating member 41 is provided on an outer peripheral surface thereof with a male thread 41d. The locking device for the L-R steering device 13LR is provided inside the L-R angle knob 23 with an axially-movable lock member (friction brake member) 46. The axially-movable lock member 46 is positioned around the rotational shaft 20 and is provided on an inner peripheral surface thereof with a female thread 46a which is in mesh with the male thread 41d of the cylindrical portion 41a. As shown in FIG. 5, the rotational shaft 20 is partly formed as a non-cylindrical portion 22 having a non-circular cross section. A (removable) retaining member 47 having a generally hexagonal section is fitted on the non-cylindrical portion 22 at the bottom of the axially-movable lock member 46, and is coupled to the axially-movable lock member 46 in a non-rotatable manner relative to the axially-movable lock member 46 to prevent the axially-movable lock member 46 from rotating relative to the rotational shaft 20. Thus, the axially-movable lock member 46 rotates together with the rotational shaft 20. Accordingly, turning the L-R lock knob 42 causes the axially-movable lock member 46 to move along the axis of the rotational shaft 20 without rotating about the rotational shaft 20 due to the engagement of the male thread 41d with the female thread 46a.

If the axially-movable lock member 46 moves up and down by rotation of the integral member including the first rotating member 41 and the L-R lock knob 42, a first friction pad 46b fixed to an upper face of the axially-movable lock member 46 is engaged with and disengaged from a second friction pad 48a fixed to an axially-immovable lock member (friction brake member) 48, respectively. Each of the first and second friction pads 46b and 48a is in the shape of a disk. The first friction pad 46b can be made of a material having a high coefficient of friction such as cork or silicone rubber, while the second friction pad 48a can be made of, for example metal (stainless steel). The axially-immovable lock member 48 is coupled to the inner control shaft 21 via a female thread 48b which is formed on an inner peripheral surface of the axially-immovable lock member 48 and the aforementioned male thread 21e that meshes with the female thread 48b, so that the axially-immovable lock member 48 rotates together with the inner control shaft 21 when the L-R angle knob 23 is turned. If the first friction pad 46b is brought into pressing contact with the second friction pad 48a by an upward movement of the axially-movable lock member 46, the rotation of the axially-immovable lock member 48 is restricted by friction generated between the first and second friction pads 46b and 48a. If the axially-immovable lock member 48 is locked via the first and second friction pads 46b and 48a, the integral member including the inner control shaft 21 and the L-R angle knob 23 is prohibited from rotating, so that the first pulley 24 is also prohibited from rotating. As a result, the bendable portion 12a is prohibited from bending right and left, so that the bendable portion 12a can be locked to a desired curved shape in a left or right direction. More specifically, turning the L-R lock knob 42 in the direction of an arrow F' or a locking force applying direction (i.e., counterclockwise as viewed in FIG. 10) causes the axially-movable lock member 46 to move upward to bring the first friction pad 46b into pressing contact with the second friction pad 48a to thereby restrict the rotation of the L-R angle knob 23. On the other hand, turning the L-R lock knob 42 in the direction shown by a triangular arrow "A" and a letter "F" which are printed on the L-R lock knob 42 or a locking force releasing direction (i.e., clockwise as viewed in FIG. 10) causes the axially-movable lock member 46 to move downward to disengage the first friction pad 46b from the second friction pad 48a to thereby allow the L-R angle knob 23 to be turned freely. Although the L-R lock knob 42 stops with a click at each of the two stop positions thereof as has been described, the L-R angle knob 23 is locked when the L-R lock knob 42 stops at one of the two stop positions, while the L-R angle knob 23 is allowed to be turned when the L-R lock knob 42 stops at the other stop position. The former and latter stop positions are herein referred to as "lock position" and "unlock position", respectively. Each of the axially-movable lock member 46 and the axially-immovable lock member 48 is formed as an annular member so that the first friction pad 46b can be pressed against the second friction pad 48a regardless of the rotational position of the axially-immovable lock member 48, which rotates together with the L-R angle knob 23, relative to the axially-movable lock member 46.

In a state where the integral member including the inner control shaft 21 and the L-R angle knob 23 is prohibited from rotating, only the axially-immovable lock member 48 can be rotated relative to the outer cylindrical portion 21d to adjust the vertical position (i.e., the vertical position as viewed in FIG. 2) of the axially-immovable lock member 48 relative to the axially-movable lock member 46 via the engagement of the female thread 48b with the male thread 21e. If the vertical position of the axially-immovable lock member 48 relative to the axially-movable lock member 46 can be adjusted, the locking force applied to the L-R angle knob 23 can be adjusted since the frictional resistance between the first and second friction pads 46b and 48a in a state where the L-R lock knob 42 stops at the lock position varies. For instance, the frictional resistance between the first and second friction pads 46b and 48a can be set so that the bendable portion 12a is half-locked, i.e., so that the bendable portion 12a in a locked state is unlocked in accordance with the degree of an external force applied to the bendable portion 12a. Such an adjustment of the frictional resistance between the first and second friction pads 46b and 48a can be easily carried out by adjusting the vertical position of the axially-immovable lock member 48 by rotating the axially-immovable lock member 48 relative to the outer cylindrical portion 21d.

In the following description, the locking device for the U-D steering device 13UD will be hereinafter discussed in detail.

The U-D steering device 13UD is provided around the outer control shaft 31 with the aforementioned stationary hollow cylindrical base 50, which is coaxial to the rotational shaft 20. The inner end (the lower end as viewed in FIG. 2) of the cylindrical base 50 is fixed to the substrate 11b together with the rotational shaft 20. The inner and outer control shafts 21 and 31 and the first and second pulleys 24 and 34 are held between the rotational shaft 20 and the cylindrical base 50 A second rotating member 51 which includes a cylindrical portion 51a and a disk portion 51b is fitted on the cylindrical base 50. The cylindrical portion 51a is fitted on the rotational shaft 20 to be rotatable relative to the rotational shaft 20 and to be immovable in the axial direction (the vertical direction as viewed in FIG. 2) of the rotational shaft 20 relative thereto. A U-D lock lever 52 is fixed to the disk portion 51b, so that the second rotating member 51 and the U-D lock lever 52 constitutes a locking member (second locking member). The disk portion 51b is provided with a plurality of circular holes 51c at equiangular intervals about the axis of the rotational shaft 20. The U-D lock lever 52 is provided with a plurality of projections 52a at equiangular intervals about the axis of the rotational shaft 20. The plurality of projections 52a are firstly fitted in the plurality of circular holes 51c, respectively, and subsequently the tip of each projection 52a is melted by heat to fix the U-D lock lever 52 to the second rotating member 51. Accordingly, the U-D lock lever 52 together with the second rotating member 51 is supported by the cylindrical base 50 to be rotatable about the cylindrical portion 51a (i.e., the rotational shaft 20). Unlike the hollow L-R lock knob 42, the U-D lock lever 52 is formed to extend radially in a direction perpendicular to the axis of the rotational shaft 20 so as to be easily turned manually.

An integral member including the second rotating member 51 and the U-D lock lever 52 can rotate within a predetermined range which is defined by a rotational range defining mechanism (not shown) provided between the cylindrical portion 51a and the cylindrical base 50. With the rotational range defining mechanism, the U-D lock lever 52 stops with a click with an engaging spring 55 at each of two stop positions corresponding to the opposite ends of the rotational range of the U-D lock lever 52.

The cylindrical portion 51a of the second rotating member 51 is provided on an outer peripheral surface thereof with a male thread 51d. The locking device for the U-D steering device 13UD is provided inside the U-D angle knob 33 with an axially-movable lock member (friction brake member) 56. The axially-movable lock member 56 is positioned around the rotational shaft 20 and is provided on an inner peripheral surface thereof with a female thread 56a which is in mesh with the male thread 51d of the cylindrical portion 51a. As shown in FIG. 6, the upper end of the cylindrical base 50 is formed as a non-cylindrical portion 54 having a non-circular cross section. An annular joint member 57 which is fixed to the axially-movable lock member 56 and whose cross sectional shape substantially corresponds to that of the non-cylindrical portion 54 of the cylindrical base 50 is firmly fitted on the non-cylindrical portion 54 so that the axially-movable lock member 56 does not rotate relative to the cylindrical base 50 and the rotational shaft 20. Thus, the axially-movable lock member 56 is prohibited from rotating about the cylindrical base 50. Accordingly, turning the U-D lock lever 52 causes the axially-movable lock member 56 to move along the axis 20x of the rotational shaft 20 without rotating about the rotational shaft 20 due to the engagement of the male and female threads 51d and 56a. The annular joint member 57 can be a member separate from the axially-movable lock member 56, or can be formed integral with the axially-movable lock member 56.

If the axially-movable lock member 56 moves up and down by rotation of the integral member including the second rotating member 51 and the U-D lock lever 52, a first friction pad 56b formed integral with the upper end of the axially-movable lock member 56 is engaged with and disengaged from a second friction pad 58a fixed to an axially-immovable lock member (friction brake member) 58, respectively. Each of the first and second friction pads 56b and 58a is in the shape of a disk. The first friction pad 56b can be made of, for example metal (stainless steel), while the second friction pad 58a can be made of, for example cork or silicone rubber. The axially-immovable lock member 58 is coupled to the metal ring 33e of the U-D angle knob 33 so that the axially-immovable lock member 58 rotates together with the U-D angle knob 33 when the U-D angle knob 33 is turned. If the first friction pad 56b is brought into pressing contact with the second friction pad 58a by a downward movement of the axially-movable lock member 56, the rotation of the axially-immovable lock member 58 is restricted by friction generated between the first and second friction pads 56b and 58a. If the axially-immovable lock member 58 is locked via the first and second friction pads 56b and 58a, an integral member including the outer control shaft 31 and the U-D angle knob 33 is prohibited from rotating, so that the second pulley 34 is also prohibited from rotating. As a result, the bendable portion 12a is prohibited from bending upward and downward, so that the bendable portion 12a can be locked to a desired curved shape in an upward or downward direction. More specifically, turning the U-D lock lever 52 in the direction of the arrow F' or a lock-applying direction (i.e., counterclockwise as viewed in FIG. 10) causes the axially-movable lock member 56 to move downward to bring the first friction pad 56b into pressing contact with the second friction pad 58a to thereby restrict the rotation of the U-D angle knob 33. On the other hand, turning the U-D lock lever 52 in the direction shown by a triangular arrow "Δ" and a letter "F" which are printed on the U-D lock lever 52 or a lock-releasing direction (i.e., clockwise as viewed in FIG. 10) causes the axially-movable lock member 56 to move upward to disengage the first friction pad 56b from the second friction pad 58a to thereby allow the U-D angle knob 33 to be turned freely. Although the U-D lock lever 52 stops with a click at each of the two stop positions thereof as has been described, the U-D angle knob 33 is locked when the U-D lock lever 52 stops at one of the two stop positions, while the U-D angle knob 33 is allowed to be turned when the U-D lock lever 52 stops at the other stop position. The former and latter stop positions are herein referred to as "lock position" and "unlock position", respectively. Each of the axially-movable lock member 56 and the axially-immovable lock member 58 is formed as an annular member so that the first friction pad 56b can be pressed against the second friction pad 58a regardless of the rotational position of the axially-immovable lock member 58, which rotates together with the U-D angle knob 33, relative to the axially-movable lock member 56.

The axially-immovable lock member 58 is fitted in the metal ring 33e, which is fixed to the U-D angle knob 33, so that the axial position of the axially-immovable lock member 58 can be adjusted relative to the metal ring 33e. A female thread 33k formed on an inner peripheral surface of the metal ring 33e is in mesh with a male thread 60a formed on an outer peripheral surface of an adjusting ring 60 (see FIG. 15). This adjusting ring 60 supports the axially-immovable lock member 58 from the bottom thereof. If the adjusting ring 60 is rotated in a state where the integral member including the outer control shaft 31 and the U-D angle knob 33 is held so as not to rotate relative to the rotational shaft 20, the vertical position (i.e., the vertical position as viewed in FIG. 2) of the adjusting ring 60 relative to the metal ring 33e can be adjusted due to the engagement of the female thread 33k with the male thread 60a. Accordingly, the vertical position of the axially-immovable lock member 58 relative to the axially-movable lock member 56 can be adjusted by rotating the adjusting ring 60 relative to the metal ring 33e. If the vertical position of the axially-immovable lock member 58 relative to the axially-movable lock member 56 can be adjusted, the locking force applied to the U-D angle knob 33 can be adjusted since the frictional resistance between the first and second friction pads 56b and 58a in a state where the U-D lock lever 52 stops at the lock position varies. For instance, the frictional resistance between the first and second friction pads 56b and 58a can be set so that the bendable portion 12a is half-locked, i.e., so that the bendable portion 12a in a locked state is unlocked in accordance with the degree of an external force applied to the bendable portion 12a. Such an adjustment of the frictional resistance between the first and second friction pads 56b and 58a can be easily carried out by adjusting the vertical position of the axially-immovable lock member 58 relative to the axially-movable lock member 56 by rotating the adjusting ring 60.

The above described elements of each of the L-R steering device 13LR and the U-D steering device 13UD are assembled about the rotational shaft 20 during assembly of the steering device 13. The U-D steering device 13UD is held between the disk portion 21b of the inner control shaft 21 and the first pulley 24, which are elements of the L-R steering device 13LR, so that the vertical position of the U-D steering device 13UD is determined by the disk portion 21b and the first pulley 24. The rotational shaft 20 is provided between the opposite ends thereof with an annular groove in which a retaining member 61 is fitted. The retaining member 61 is engaged with the upper end of the inner control shaft 21. With this structure, the U-D steering device 13UD and the integral member including the inner control shaft 21 and the L-R angle knob 23 are prevented from coming off the rotational shaft 20. The integral member including the first rotating member 41 and the L-R lock knob 42, which is positioned above the L-R angle knob 23, is prevented from coming off the rotational shaft 20 due to the aforementioned retaining ring 44. Accordingly, the whole of the steering device 13 (13LR and 13UD) is supported by the rotational shaft 20 so as not to come off the rotational shaft 20.

The steering device 13 is provided therein with a plurality of sealing members (e.g., elastic O-rings) for preventing any foreign matter (e.g., water, moisture, dust and the like) from entering into the steering device 13. Such a plurality of sealing members include first through fifth sealing member groups S1, S2, S3, S4 and S5. The housing 11a is sealed with the first sealing member group S1. The L-R angle knob 23 is sealed with the second sealing member group S2. The U-D angle knob 33 is sealed with the third sealing member group S3. The L-R lock knob 42 is sealed with the fourth sealing member group S4. The outer control shaft 31 is sealed with respect to the inner control shaft 21 with the fifth sealing member group S5. For instance, in the case where the endoscope 10 is immersed in a disinfecting solution, all the external surfaces of the endoscope 10 are properly disinfected while completely preventing the disinfecting solution from entering into the hollow L-R angle knob 23, the hollow U-D angle knob 33, the hollow L-R lock knob 42 and the housing 11a.

As has been described above, in the L-R steering device 13LR, turning the L-R lock knob 42 to the lock position thereof causes the axially-movable lock member 46 to move upward to bring the first friction pad 46b into pressing contact with the second friction pad 48a to thereby restrict the rotation of the L-R angle knob 23 together with the inner control shaft 21. As a result, the bendable portion 12a is prohibited from bending right and left, so that the bendable portion 12a can be locked to a desired curved shape in a left or right direction. The axially-movable lock member 46 is supported to be movable only in the axial direction of the rotational shaft 20 without rotating together with the L-R lock knob 42 relative to the rotational shaft 20. This makes it possible to lock the bendable portion 12a to a desired curved shape in a left or right direction without transmitting rotation of the L-R lock knob 42 to the L-R angle knob 23. The supporting guide mechanism of the axially-movable lock member 46 will be hereinafter discussed with reference to FIGS. 12 through 14. It should be noted that only a few elements are hatched in FIG. 12 for the purpose of illustration and no elements are hatched in FIGS. 13 and 14 for the purpose of illustration.

That portion of the rotational shaft 20 on which the inner control shaft 21 (the cylindrical shaft portion 21a) is fitted is formed to have a circular cross section so that an integral member including the inner control shaft 21 and the L-R angle knob 23 can rotate about the axis 20x of the rotational shaft 20 relative to the rotational shaft 20. The rotational shaft 20 is provided above the upper end of the inner control shaft 21 with the aforementioned non-cylindrical portion 22 having a non-circular cross section. The non-cylindrical portion 22 is provided with two rotation restricting surfaces 22a which extend vertically in parallel to each other in the direction of the axis 20x of the rotational shaft 20, a connecting surface 22b (see FIG. 13) which extends between the two rotation restricting surfaces 22a to connect the two rotation restricting surfaces 22a, and a pair of vertical opposite surfaces 22c (see FIG. 12) which are separate from each other in the direction of the axis 20x of the rotational shaft 20.

The retaining member 47 is shaped like a hexagonal prism that is formed separately from the axially-movable lock member 46. The retaining member 47 is provided with a groove 47a which extends radially outwards from the center of the retaining member 47, so that the retaining member 47 has a generally C-shape section. The retaining member 47 is provided in the groove 47a with two rotation restricting surfaces 47b which face each other to extend vertically in parallel to each other. The width between the two rotation restricting surfaces 47b corresponds to the width between the two rotation restricting surfaces 22a of the non-cylindrical portion 22. The retaining member 47 is further provided with a connecting surface 47c which extends between the two rotation restricting surfaces 47b to connect these two surfaces 47b. The height (the axial length) of the retaining member 47 corresponds to the width between the pair of vertical opposite surfaces 22c of the non-cylindrical portion 22 of the rotational shaft 20.

Figure 14:
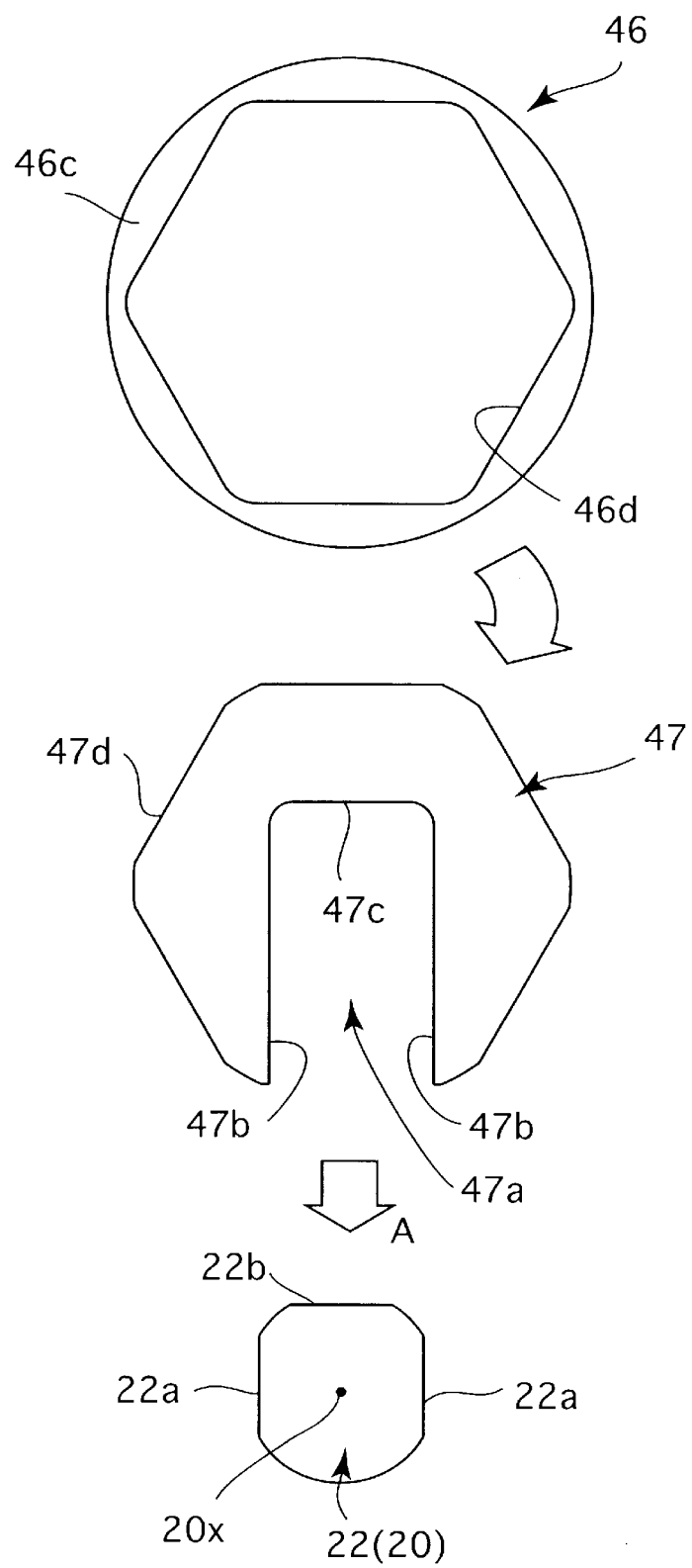
FIG. 14 is an exploded cross sectional view of the elements shown in FIG. 13.

Therefore, if the retaining member 47 is fitted on the non-cylindrical portion 22 of the rotational shaft 20 in a direction perpendicular to the axis 20x of the rotational shaft 20, i.e., in a direction shown by an arrow "A" in FIG. 14 so that the non-cylindrical portion 22 is fitted in the groove 47a, the two rotation restricting surfaces 47b come in contact with the two rotation restricting surfaces 22a, respectively, so that the retaining member 47 does not rotate relative to the rotational shaft 20 about the axis 20x thereof. In this state, the retaining member 47 cannot move in the direction of the axis 20x relative to the rotational shaft 20 either, since the retaining ring 47 is held between the pair of vertical opposite surfaces 22c of the rotational shaft 20. When the retaining member 47 is fitted on the non-cylindrical portion 22, the non-cylindrical portion 22 is inserted into the groove 47a of the retaining ring 47 until the connecting surface 22b comes into contact with the connecting surface 47c (see FIG. 13).

Moreover, a socket portion (guide portion) 46c formed at the bottom center of the axially-movable lock member 46 is fitted on the retaining member 47. The inner peripheral surface of the socket portion 46c is formed as a rotation restricting surface having a hexagonal cross section corresponding to the cross sectional shape of the outer peripheral surface 47d of the retaining member 47. Therefore, if the retaining member 47 is inserted into the socket portion 46c in the direction of the axis 20x, the socket portion 46c is coupled to the retaining member 47 so that the socket portion 46c cannot rotate relative to the retaining member 47. Namely, the axially-movable lock member 46 is coupled to the rotational shaft 20 so that the axially-movable lock member 46 cannot rotate relative to the rotational shaft 20 due to the engagement of the socket portion 46c and the retaining member 47.

The socket portion 46c of the axially-movable lock member 46 is fitted on the retaining member 47 to be slidable thereon in the direction of the axis 20x of the rotational shaft 20. As has been described above, the axially-movable lock member 46 is supported by the integral member including the first rotating member 41 and the L-R lock knob 42 via the male and female threads 41d and 46a. With this structure, turning the L-R lock knob 42 causes the axially-movable lock member 46 to move along the axis 20x of the rotational shaft 20 without rotating about the rotational shaft 20 due to the engagement of the male thread 41d with the female thread 46a. If the first friction pad 46b is brought into pressing contact firmly with the second friction pad 48a by an upward movement of the axially-movable lock member 46, the integral member including the first rotating member 41 and the L-R lock knob 42 is prohibited from rotating. As a result, the bendable portion 12a is prohibited from bending right and left, so that the bendable portion 12a can be locked to a desired curved shape in a left or right direction. The socket portion 46c remains fitted on the retaining member 47 regardless of the movement of the axially-movable lock member 46 relative to the retaining member 47 in the direction of the axis 20x of the rotational shaft 20.

As can be understood from the above descriptions, in the L-R steering device 13LR, the axially-movable lock member 46 does not rotate in the direction of rotation of the L-R lock knob 42 but moves in the direction of the axis 20x, which the L-R lock knob 42 rotates about, when receiving rotational force from the L-R lock knob 42. Since the integral member including the inner control shaft 21 and the L-R angle knob 23, which is to be locked with the axially-movable lock member 46, is an element of the L-R steering device 13LR which is rotated about an axis coaxial to the axis of rotation of the L-R lock knob 42, the direction of movement of the axially-movable lock member 46 is not the same as the rotational direction of the integral member including the inner control shaft 21 and the L-R angle knob 23, either. In other words, the rotation of the L-R lock knob 42 is not transmitted to the L-R angle knob 23 via the axially-movable lock member 46 when the L-R lock knob 42 is turned to the lock position thereof since the L-R steering device 13LR is structured such that the rotational force of the L-R lock knob 42 when it is turned to the lock position thereof is converted solely into the axial moving force for moving the axially-movable lock member 46 in the axis 20x of the rotational shaft 20 (i.e., in the vertical direction as viewed in FIG. 2) to lock the integral member including the inner control shaft 21 and the L-R angle knob 23. Accordingly, the bendable portion 12a does not bend right or left unexpectedly by the rotational movement of the L-R lock knob 42, so that the bendable portion 12a can be securely locked to a desired curved shape in a left or right direction.

Similar to the L-R steering device 13LR, in the U-D steering device 13UD, turning the U-D lock lever 52 to the lock position thereof causes the axially-movable lock member 56 to move downward to bring the first friction pad 56b into pressing in contact with the second friction pad 58a to thereby restrict the rotation of the U-D angle knob 33 together with the outer control shaft 31. As a result, the bendable portion 12a is prohibited from bending upward and downward, so that the bendable portion 12a can be locked to a desired curved shape in an upward or downward direction. The axially-movable lock member 56 is supported to be movable only in the axial direction of the rotational shaft 20 without rotating together with the U-D lock lever 52 relative to the rotational shaft 20. This makes it possible to lock the bendable portion 12a to a desired curved shape in an upward or downward direction without transmitting rotation of the U-D lock lever 52 to the U-D angle knob 33.

Figure 16:
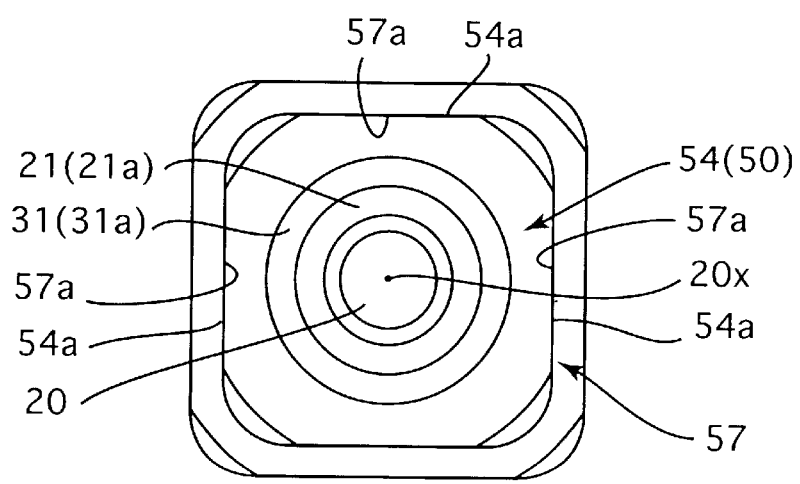
FIG. 16 is a cross sectional view of the first embodiment of the control device of the endoscope shown in FIG. 2, taken along XVI—XVI line in FIG. 15, viewed in the direction of the appended arrows.

The supporting guide mechanism of the axially-movable lock member 56 will be hereinafter discussed with reference to FIGS. 15 and 16. It should be noted that only a few elements are hatched in FIG. 15 for the purpose of illustration and that no elements are hatched in FIG. 16 for the purpose of illustration.

The portion of the stationary hollow cylindrical base 50 on which the second rotating member 51 is fitted is formed to have a circular cross section so that the integral member including the second rotating member 51 and the U-D lock lever 52 can rotate about the axis 20x of the rotational shaft 20 relative to the rotational shaft 20. The cylindrical base 50 is provided at the upper end thereof with the aforementioned non-cylindrical portion 54 having a generally square non-circular cross section (see FIG. 16). The non-cylindrical portion 54 is provided with four rotation restricting surfaces 54a which extend vertically in parallel to the axis 20x of the rotational shaft 20, and a bottom-support surface 54b which extends perpendicular to the two rotation restricting surfaces 54a.

The annular joint member 57, positioned on top of the axially-movable lock member 56, is shaped to have a substantially square cross section to be fitted on the non-cylindrical portion 54. The inner peripheral surface of the annular joint member 57 is formed as a rotation restricting surface 57a which comes in contact with the four rotation restricting surfaces 54a. Therefore, if the annular joint member 57 is fitted on the non-cylindrical portion 54 of the cylindrical base 50, the axially-movable lock member 56 is supported by the cylindrical base 50 so as not to rotate about the axis 20x relative to the cylindrical base 50 due to the engagement of the rotation restricting surface 57a with the four rotation restricting surfaces 54a.

The annular joint member 57 of the axially-movable lock member 56 is fitted on the non-cylindrical portion 54 to be slidable thereon in the direction of the axis 20x of the rotational shaft 20. As has been described, the axially-movable lock member 56 is supported by the integral member including the second rotating member 51 and the U-D lock lever 52 via the male and female threads 51d and 56a. With this structure, turning the U-D lock lever 52 causes the axially-movable lock member 56 to move along the axis 20x of the rotational shaft 20 without rotating about the rotational shaft 20 due to the engagement of the male and female threads 51d and 56a. If the first friction pad 56b is brought into pressing contact firmly with the second friction pad 58a by a downward movement of the axially-movable lock member 56, the integral member including the second rotating member 51 and the U-D lock lever 52 is prohibited from rotating. As a result, the bendable portion 12a is prohibited from bending upward and downward, so that the bendable portion 12a can be locked to a desired curved shape in an upward or downward direction. The annular joint member 57 remains fitted on the non-cylindrical portion 54 regardless of the movement of the axially-movable lock member 56 relative to the annular joint member 57 in the direction of the axis 20x of the rotational shaft 20.

As can be understood from the above descriptions, in the U-D steering device 13UD, the axially-movable lock member 56 does not rotate in the direction of rotation of the U-D lock lever 52 but moves in the direction of the axis 20x, which the U-D lock lever 52 rotates about, when receiving rotational force from the U-D lock lever 52. Since the integral member including the outer control shaft 31 and the U-D angle knob 33, which is to be locked with the axially-movable lock member 56, is an element of the U-D steering device 13UD which is rotated about an axis coaxial to the axis of rotation of the U-D lock lever 52, the direction of movement of the axially-movable lock member 56 is not the same as the rotational direction of the integral member including the outer control shaft 31 and the U-D angle knob 33. In other words, the rotation of the U-D lock lever 52 is not transmitted to the U-D angle knob 33 via the axially-movable lock member 56 when the U-D lock lever 52 is turned to the lock position thereof since the U-D steering device 13UD is structured such that the rotational force of the U-D lock lever 52 when turned to the lock position thereof is converted solely into the axial moving force for moving the axially-movable lock member 56 in the axis 20x of the rotational shaft 20 (i.e., in the vertical direction as viewed in FIG. 2) to lock the integral member including the outer control shaft 31 and the U-D angle knob 33. Accordingly, the bendable portion 12a does not bend upward or downward unexpectedly by the rotational movement of the U-D lock lever 52, so that the bendable portion 12a can be securely fixed to a desired curved shape in upward or downward directions.

The L-R steering device 13LR, the U-D steering device 13UD, the locking device for the L-R steering device 13LR and the locking device for the U-D steering device 13UD that have been all described above are fundamental elements of the first embodiment of the control device of the endoscope 10.

As can be understood from the above descriptions, in the first embodiment of the control device of the endoscope 10, since the axially-movable lock member 46 moves only in the direction of the rotational axis (i.e., the axis 20x) of each of the L-R angle knob 23 and the L-R lock knob 42 in the L-R steering device 13LR when the bendable portion 12a is locked in a left or right direction by turning the L-R lock knob 42, and since the axially-movable lock member 56 moves only in the direction of the rotational axis (i.e., the axis 20x) of each of the U-D angle knob 33 and the U-D lock lever 52 in the U-D steering device 13UD when the bendable portion 12a is locked in an upward or downward direction by turning the U-D lock lever 52, rotation of the L-R lock knob 42 and the U-D lock lever 52 is not transmitted at all to the L-R angle knob 23 and the U-D angle knob 33, respectively. Accordingly, the curved shape of the bendable portion 12a does not change at all by the operation of either the L-R lock knob 42 or the U-D lock lever 52, which ensures accurate operability of the control device of the endoscope 10.

Furthermore, in the first embodiment of the control device of the endoscope 10, the position of the axially-immovable lock member 48 relative to the integral member including the inner control shaft 21 and the L-R angle knob 23 can be adjusted in the direction of movement of the axially-movable lock member 46, while the position of the axially-immovable lock member 58 relative to the integral member including the outer control shaft 31 and the U-D angle knob 33 can be adjusted in the direction of movement of the axially-movable lock member 56. The locking force by the locking device for the L-R steering device 13LR can be finely adjusted by adjusting the position of the axially-immovable lock member 48 in such a manner. Likewise, the locking force by the locking device for the U-D steering device 13UD can be finely adjusted by adjusting the position of the axially-immovable lock member 58 in such a manner.

As can be understood from the foregoing, according to the first embodiment of the control device of the endoscope 10, the curved shape of the distal end of the endoscope 10 does not change by the operation of either the L-R lock knob 42 or the U-D lock lever 52.

The present invention is not limited solely to the above illustrated embodiment. For instance, although the axially-movable lock member 46 is moved along the axis 20x of the rotational shaft 20 without rotating about the rotational shaft 20 via the male and female threads 41d and 46a by turning the L-R lock knob 42, the axially-movable lock member 46 can be moved in the same manner via a cam mechanism by turning the L-R lock knob 42 without the use of threads such as the male and female threads 41d and 46a. Similarly, although the axially-movable lock member 56 is moved along the axis 20x of the rotational shaft 20 without rotating about the rotational shaft 20 via the male and female threads 51d and 56a by turning the U-D lock lever 52, the axially-movable lock member 56 can be moved in the same manner via a cam mechanism by turning the U-D lock lever 52 without the use of threads such as the male and female threads 51d and 56a. In short, each of the axially-movable lock members 46 and 56 only needs to be moved along the axis 20x of the rotational shaft 20 without rotating about the rotational shaft 20 via any device or mechanism by turning the corresponding lock knob (L-R lock knob 42) or lever (U-D lock lever 52) thereof.

The L-R angle knob 23 and the disk portion 21b of the inner control shaft 21, which are elements of the L-R steering device 13LR, and the U-D angle knob 33 and the disk portion 31b of the outer control shaft 31, which are elements of the U-D steering device 13UD, are positioned adjacent to each other in the direction of the axis 20x of the rotational shaft 20. The inner control shaft 21 and the outer control shaft 31 contact each other in the vicinity of the sealing member (an O-ring) S5 in a manner such that a movement of one of the outer and inner control shafts 21 and 31 in the direction of the axis 20x so as to mutually approach each other is transmitted to the other control shaft 21 or 31.

As has been discussed above, in the L-R steering device 13LR, turning the L-R lock knob 42 from the unlock position to the lock position causes the axially-movable lock member 46 to move linearly along the axis of the rotational shaft 20 so that the first friction pad 46b comes into pressing contact with the second friction pad 48a to lock the bendable portion 12 in a left or right direction. A drive force transmitting mechanism for moving the axially-movable lock member 46 along the axis 20x of the rotational shaft 20 in accordance with rotation of the L-R lock knob 42 includes the male and female threads 41d and 46a. The thread profile (direction of inclination) of each of the male and female threads 41d and 46a is determined so that the axially-movable lock member 46 moves upward along the axis 20x (upward as viewed in FIG. 2) by a rotation of the L-R lock knob 42 from the unlock position to the lock position thereof.

Namely, in the L-R steering device 13LR, the axially-movable lock member 46 is structured to press the integral member including the inner control shaft 21 and the L-R angle knob 23 in a direction away from the integral member including the outer control shaft 31 and the U-D angle knob 33 (i.e., upward as viewed in FIG. 2), which is not to be locked by the L-R steering device 13LR, when the L-R lock knob 42 is turned to the lock position to lock the bendable portion 12 in a left or right direction. Therefore, when the L-R lock knob 42 is turned to the lock position to lock the bendable portion 12 in a left or right direction in the L-R steering device 13LR, no force which may interfere with the rotation of the integral member including the outer control shaft 31 and the U-D angle knob 33 is exerted upon the integral member including the outer control shaft 31 and the U-D angle knob 33 by the axially-movable lock member 46. This ensures accurate operability of the U-D angle knob 33.

Contrary to the illustrated embodiment, if the axially-movable lock member 46 were to be structured so as to press the integral member including the inner control shaft 21 and the L-R angle knob 23 in a direction toward the integral member including the outer control shaft 31 and the U-D angle knob 33 (i.e., downward as viewed in FIG. 2) when the L-R lock knob 42 is turned to the lock position to lock the bendable portion 12 in a left or right direction, there is a possibility of the integral member including the inner control shaft 21 and the L-R angle knob 23 being pressed against the integral member including the outer control shaft 31 and the U-D angle knob 33 of the U-D steering device 13UD to thereby transmit part of the locking force of the axially-movable lock member 46 to the U-D steering device 13UD. In other words, there is a possibility of the integral member including the outer control shaft 31 and the U-D angle knob 33 being locked to some extent due to the operation of the L-R lock knob 42 for the L-R steering device 13LR even if the U-D lock lever 52 is positioned at the unlock position thereof. It is of course desirable when using the U-D steering device 13UD that the integral member including the outer control shaft 31 and the U-D angle knob 33 can be turned freely without unnecessary rotational resistance when the U-D lock lever 52 is positioned at the unlock position thereof; however such an operation interference problem is reliably prevented from occurring in control device of the endoscope 10 of the first embodiment.

In the U-D steering device 13UD of the first embodiment, turning the U-D lock lever 52 from the unlock position to the lock position causes the axially-movable lock member 56 to move linearly along the axis of the rotational shaft 20 so that the first friction pad 56b comes into pressing contact with the second friction pad 58a to lock the bendable portion 12 in an upward or downward direction. The drive force transmitting mechanism for moving the axially-movable lock member 56 along the axis 20x of the rotational shaft 20 in accordance with rotation of the U-D lock lever 52 includes the male and female threads 51d and 56a. The thread profile (direction of inclination) of each of the male and female threads 51d and 56a is determined so that the axially-movable lock member 56 moves downward along the axis 20x (downward as viewed in FIG. 2) by a rotation of the U-D lock lever 52 from unlock position to the lock position thereof.

Namely, similar to the L-R steering device 13LR, in the U-D steering device 13UD, the axially-movable lock member 56 is structured to press the integral member including the outer control shaft 31 and the U-D angle knob 33 in a direction away from the integral member including the inner control shaft 21 and the L-R angle knob 23 (i.e., downward as viewed in FIG. 2), which is not to be locked by the U-D steering device 13UD, when the U-D lock lever 52 is turned to the lock position to lock the bendable portion 12 in upward and down directions. Therefore, when the U-D lock lever 52 is turned to the lock position to lock the bendable portion 12 in an upward or downward direction in the U-D steering device 13UD, no force which may interfere with the rotation of the integral member including the inner control shaft 21 and the L-R angle knob 23 is exerted upon the integral member including the inner control shaft 21 and the L-R angle knob 23 by the axially-movable lock member 56. This ensures accurate operability of the L-R angle knob 23.

Contrary to the illustrated embodiment, if the axially-movable lock member 56 were to be structured so as to press the integral member including the outer control shaft 31 and the U-D angle knob 33 in a direction toward the integral member including the inner control shaft 21 and the L-R angle knob 23 (i.e., upward as viewed in FIG. 2) when the U-D lock lever 52 is turned to the lock position to lock the bendable portion 12 in upward and down directions, there is a possibility of the integral member including the outer control shaft 31 and the U-D angle knob 33 being pressed against the integral member including the inner control shaft 21 and the L-R angle knob 23 of the L-R steering device 13LR to thereby transmit part of the locking force of the axially-movable lock member 56 to the L-R steering device 13LR. In other words, there is a possibility of the integral member including the inner control shaft 21 and the L-R angle knob 23 being locked to some extent due to the operation of the U-D lock lever 52 for the U-D steering device 13UD even if the L-R lock knob 42 is positioned at the unlock position thereof. It is of course desirable when using the L-R steering device 13LR that the integral member including the inner control shaft 21 and the L-R angle knob 23 can be turned freely without unnecessary rotational resistance when the L-R lock knob 42 is positioned at the unlock position thereof; however such an operation interference problem is reliably prevented from occurring in the control device of the endoscope 10 of the first embodiment.

As can be understood from the foregoing, in the first embodiment of the control device of the endoscope 10, the steering device 13, in which the integral member including the inner control shaft 21 and the L-R angle knob 23 (i.e., a first hand-operated steering member) and the integral member including the outer control shaft 31 and the U-D angle knob 33 (i.e., a second hand-operated steering member) are positioned adjacent to each other in the direction of the axis 20x of the rotational shaft 20, is structured so that the axially-movable lock member 46 moves in a direction away from the second hand-operated steering member, which is not to be locked by the L-R steering device 13LR, when the L-R lock knob 42 is turned to the lock position to lock the bendable portion 12 in a left or right direction, and so that the axially-movable lock member 56 moves in a direction away from the first hand-operated steering member, which is not to be locked by the U-D steering device 13UD, when the U-D lock lever 52 is turned to the lock position to lock the bendable portion 12 in an upward or downward direction. With this structure, the locking force of the axially-movable lock member 46 for the L-R steering device 13LR does not influence the operability of the U-D angle knob 33 of the U-D steering device 13UD, while the locking force of the axially-movable lock member 56 for the U-D steering device 13UD does not influence the operability of the L-R angle knob 23 of the L-R steering device 13LR. Therefore, the operation of locking the bendable portion 12a can be reliably performed on one of the first and second hand-operated steering members which is operated to lock the bendable portion 12a while ensuring accurate operability of the other of the first and second hand-operated steering members which is not operated to lock the bendable portion 12a. Of course, the operation of locking the bendable portion 12a can be performed on each of the first and second hand-operated steering members at the same time.

The present invention is not limited solely to the above illustrated embodiment. In the above illustrated embodiment, each of the L-R steering device 13LR and the U-D steering device 13UD is structured so that the locking force of the axially-movable lock member does not influence the operability of the angle knob 23 or 33 of the other steering device 13LR or 13UD. This is more preferable than the case where only one of the L-R steering device 13LR and the U-D steering device 13UD is structured in such a manner. However, only one of the L-R steering device 13LR and the U-D steering device 13UD can be structured in such a manner.

A feature of the illustrated embodiment is to prevent the operability of one of the first and second hand-operated steering members from deteriorating by moving one of the first and second hand-operated steering members in a direction away from the other hand-operated steering member when one of the L-R steering device 13LR and the U-D steering device 13UD is actuated to lock the bendable portion 12a. From this point of view, contrary to the illustrated embodiment, the steering device 13 can be modified so that the integral member including the outer control shaft 31 and the U-D angle knob 33 can be pressed downward with respect to FIG. 2 by an axially-movable lock member corresponding to the axially-movable lock member 46 to lock the bendable portion 12a in an upward or downward direction, and so that the integral member including the inner control shaft 21 and the L-R angle knob 23 can be pressed upward with respect to FIG. 2 by an axially-movable lock member corresponding to the axially-movable lock member 56 to lock the bendable portion 12a in a left or right direction. In this case, the axially-movable lock member corresponding to the axially-movable lock member 46 moves in a direction to approach the axially-movable lock member corresponding to the axially-movable lock member 56 to lock the bendable portion 12a in a left or right direction, while the axially-movable lock member corresponding to the axially-movable lock member 56 moves in a direction to approach the axially-movable lock member corresponding to the axially-movable lock member 46 to lock the bendable portion 12a an upward or downward direction. However, if this alternative embodiment is adopted, the structure of the locking device for each of the U-D steering device 13UD and the L-R steering device 13LR becomes quite complicated. Accordingly, it is preferable that the axially-movable lock member 46 move in a direction away from the axially-movable lock member 56 to lock the bendable portion 12a in a left or right direction, and that the axially-movable lock member 56 move in a direction away from the axially-movable lock member 46 to lock the bendable portion 12a in an upward or downward direction, just as the above illustrated embodiment.

Figure 12:
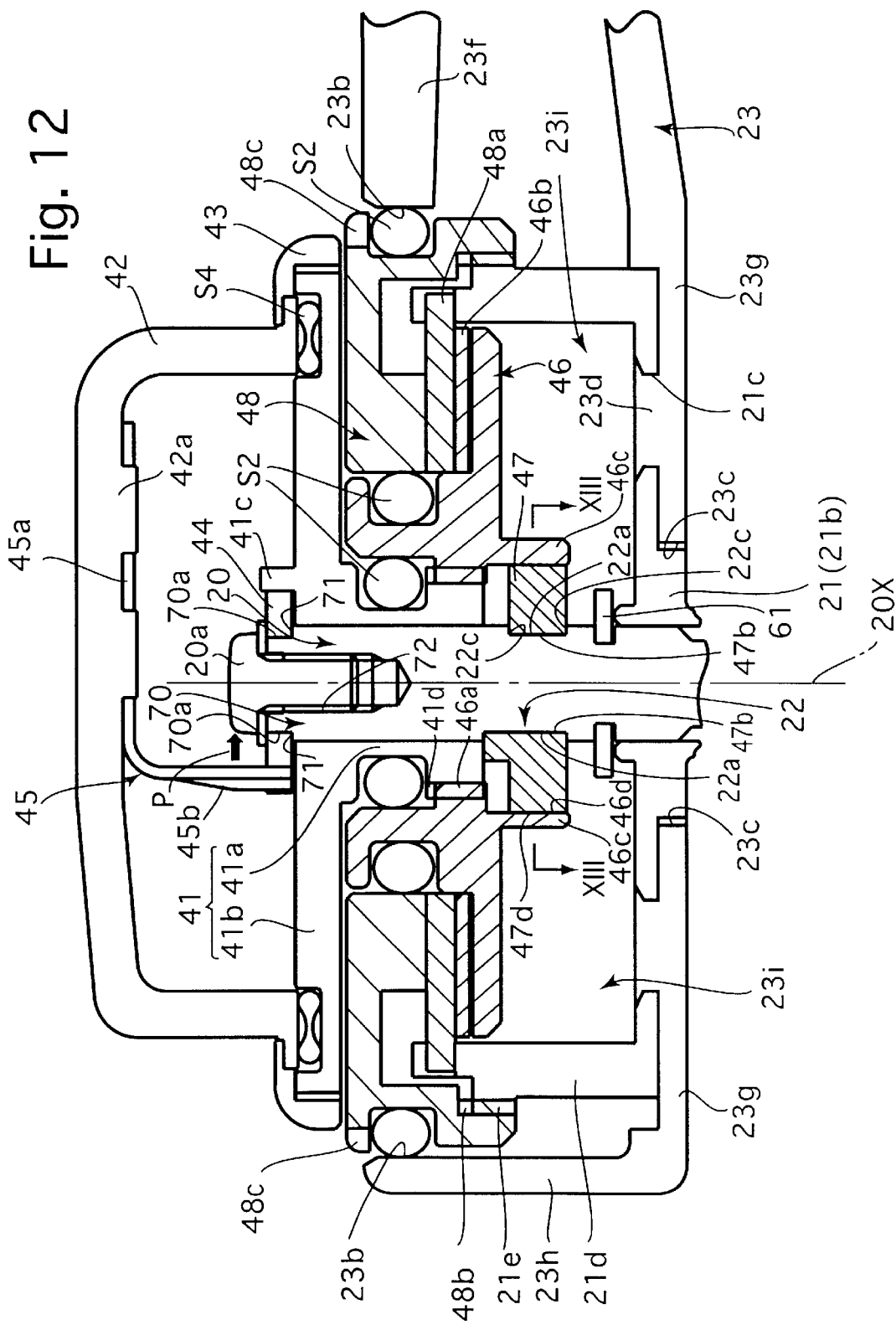
FIG. 12 is a cross sectional view of fundamental elements of the locking device for the L-R steering device and peripheral elements thereof.
Figure 13:
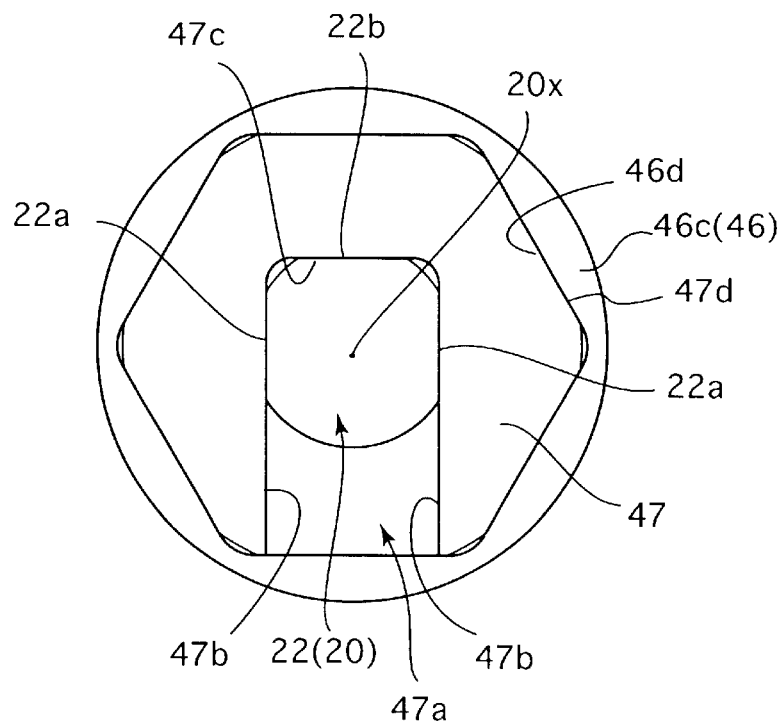
FIG. 13 is a cross sectional view of the first embodiment of the control device of the endoscope shown in FIG. 2, taken along XIII—XIII line in FIG. 12, viewed in the direction of the appended arrows.

The first embodiment of the control device of the endoscope 10 is further characterized by the supporting structure for supporting the L-R lock knob 42 that is used for locking the L-R steering device 13LR. This characteristic will be hereinafter discussed with reference to FIGS. 7, 8, 9 and 12. As has been described above, the integral member including the inner control shaft 21 and the L-R angle knob 23 of the L-R steering device 13LR is prohibited from rotating upon turning the integral member including the first rotating member 41 and the L-R lock knob 42, which are secured to each other via the fixing ring 43, to the lock position, while the integral member including the inner control shaft 21 and the L-R angle knob 23 of the L-R steering device 13LR is allowed to rotate upon turning the integral member including the first rotating member 41 and the L-R lock knob 42 to the unlock position. As shown in FIG. 12, the integral member including the first rotating member 41 and the L-R lock knob 42 is supported by the rotational shaft 20 in the vicinity of the upper end thereof to be rotatable about the axis 20x of the rotational shaft 20. More specifically, the integral member including the first rotating member 41 and the L-R lock knob 42 is supported by the rotational shaft 20 in the vicinity of the upper end thereof to be rotatable about the axis 20x of the rotational shaft 20 via the engagement of the inner peripheral surface of the cylindrical portion 41a with an outer peripheral surface of the rotational shaft 20. AS can be seen in FIG. 12, the axially-immovable lock member 48 prevents the integral member including the first rotating member 41 and the L-R lock knob 42 from moving downward as viewed in FIG. 12 along the axis 20x.

Upper end of the rotational shaft 20 which projects upward (upward as viewed in FIG. 12) from the upper end of the cylindrical portion 41a of the first rotating member 41 is formed as a non-circular end portion 70 having a non-circular section. The non-circular end portion 70 is provided with a pair of parallel surfaces 70a (see FIG. 9) which extends vertically in parallel to the axis 20x of the rotational shaft 20. The upper end of the rotational shaft 20 is provided with a pair of shoulders 71 (see FIG. 12) which extends perpendicular to the axis 20x from the lower ends of the pair of parallel surfaces 70a, respectively. The retaining ring 44 is provided in the non-circular hole 44c thereof with a pair of parallel surfaces 44d which are in contact with the pair of parallel surfaces 70a of the non-circular end portion 70, respectively. The retaining ring 44 is fitted on the non-circular end portion 70 of the rotational shaft 20 with the pair of parallel surfaces 44d being respectively engaged with the pair of parallel surfaces 70a so as to be supported by the non-circular end portion 70 on the pair of shoulders 71 without rotating about the rotational shaft 20.

The upper end of the rotational shaft 20 is provided with a screw hole 72 which extends downward as viewed in FIG. 12 along the axis 20x from the upper end of the rotational shaft 20. The retaining ring 44 is secured to the upper end of the rotational shaft 20 (i.e., the non-circular end portion 70) via the aforementioned set screw 20a that is screwed into the screw hole 72. The set screw 20a prevents the retaining ring 44 from coming off the upper end of the rotational shaft 20.

The retaining ring 44, which is fixed to the upper end of the rotational shaft 20 to be held between the pair of shoulders 71 and the set screw 20a, has a diameter greater than that of the rotational shaft 20, so that the lower end face of the retaining ring 44 faces the disk portion 41b of the first rotating member 41 as shown in FIG. 12. Therefore, the retaining ring 44 prevents the first rotating member 41 from moving upward as viewed in FIG. 12 so that the first rotating member 41 does not come off the upper end of the rotational shaft 20. In a state where the retaining ring 44 is fixed to the rotational shaft 20, a slight gap is secured between the lower face of the retaining ring 44 and the disk portion 41b of the first rotating member 41 so that the integral member including the first rotating member 41 and the L-R lock knob 42 can rotate about the axis 20x even if the set screw 20a is tightly screwed into the screw hole 72.

Accordingly, the retaining ring 44 functions to prevent the integral member including the first rotating member 41 and the L-R lock knob 42 from coming off the upper end of the rotational shaft 20 while allowing the integral member including the first rotating member 41 and the L-R lock knob 42 to rotate about the axis 20x of the rotational axis 20. As has been described above, the retaining ring 44 also functions as an element for controlling the stopping position in rotation of the integral member including the first rotating member 41 and the L-R lock knob 42.

FIG. 9 is a plan view of the retaining ring 44. The aforementioned two stop faces 44a are formed on the outer edge of the retaining ring 44 at different circumferential positions about the axis 20x. The aforementioned projection 41c, which is formed integral with the first rotating member 41, abuts against one of the two stop faces 44a when the L-R lock knob 42 is turned to the lock position thereof, while the projection 41c abuts against the other stop face 44a when the L-R lock knob 42 is turned to the unlock position thereof (see FIG. 8). In other words, the circumferential space between the two stop faces 44a is determined to correspond to the amount of rotation of the L-R lock knob 42 between the lock position and the unlock position thereof. The retaining ring 44 is provided between the two stop faces 44a with a circular arc face 44e which extends about the axis 20x. The projection 41c is provided with a corresponding arc face 41e which slides on the circular arc face 44e when the L-R lock knob 42 is turned between the lock position and the unlock position thereof.

The aforementioned two stop recesses 44b are formed on the outer edge of the retaining ring 44 at different circumferential positions about the axis 20x. The circumferential distance between the two stop recesses 44b corresponds to the circumferential distance between the two stop faces 44a. As has been described above, the two stop recesses 44b are positioned substantially on the opposite sides from the two stop faces 44a with respect to the rotational shaft 20, respectively.

The L-R lock knob 42 is provided on an inner peripheral surface thereof with a spring-supporting slot 42a (see FIG. 12). The aforementioned engaging spring 45, which is fixed to the L-R lock knob 42, is an L-shaped leaf spring provided with a flat portion 45a that is inserted into the spring-supporting slot 42a to be supported thereby, and an elastic free end portion 45b which extends substantially perpendicular to the flat portion 45a toward the first rotating member 41. The engaging spring 45 rotates together with the L-R lock knob 42 about the axis 20x of the rotational shaft 20. The free end portion 45b extends on a straight line extending substantially parallel to the axis 20x with a predetermined space between the straight line and the axis 20x so that the free end portion 45b can be engaged with the two stop recesses 44b with a click when the L-R lock knob 42 is turned to the lock position and the unlock position, respectively. The tip of the free end portion 45b is shaped to have a circular ark section corresponding to the shape of each stop recess 44b. The tip of the free end portion 45b is normally in press-contact with the retaining ring 44 in a direction toward the axis 20x (i.e., in the direction shown by an arrow P in FIG. 8 or 12). The free end portion 45b and the projection 41c are positioned substantially on opposite sides of the axis 20x, so that the projection 41c is positioned on an extension of a line in the direction of the arrow P. Since the L-R lock knob 42, to which the engaging spring 45 is fixed, and the first rotating member 41, on which the projection 41c is formed, rotate together, the positional relationship between the free end portion 45b and the projection 41c about the axis 20x is the same at all times regardless of the rotation of the L-R lock knob 42 and the first rotating member 41.

When the projection 41c of the first rotating member 41 is engaged with one of the two stop faces 44a, namely, when the L-R lock knob 42 is positioned at either the lock position or the unlock position, the free end portion 45b of the engaging spring 45 is engaged with one of the two stop recesses 44b with the spring force of the free end portion 45b to hold the L-R lock knob 42 at the lock position or the unlock position. In this state, turning the L-R lock knob 42 from the current stop position toward the other stop position thereof causes the free end portion 45b to be disengaged from the currently-engaged stop recess 44b against the biasing force of the free end portion 45b. Further turning the L-R lock knob 42 causes the first rotating member 41 to be engaged with the other stop face 44a and at the same time causes the free end portion 45b to be engaged with the other stop recess 44b, so that the integral member including the first rotating member 41 and the L-R lock knob 42 is stably held again. Accordingly, the integral member including the first rotating member 41 and the L-R lock knob 42 is controlled to stop with a click at each of the lock position and the unlock position via the two stop faces 44a, the two stop recesses 44b, the engaging spring 45 that rotates together with the L-R lock knob 42, and the projection 41c that is formed integral with the first rotating member 41.

As can be clearly understood from the above descriptions, in the first embodiment of the steering device 13 of the endoscope 10, the retaining ring 44, which functions to prevent the integral member including the first rotating member 41 and the L-R lock knob 42 from coming off the upper end of the rotational shaft 20, also functions as an element for controlling the stopping position of rotation of the integral member including the first rotating member 41 and the L-R lock knob 42 so as to stop with a click at each of the lock position and the unlock position. This reduces the number of elements of the steering device since more than one retaining member does not have to be provided to achieve the aforementioned two functions, to thereby simplifying the structure of the steering device 13.

In the first embodiment of the steering device 13 of the endoscope 10, the free end portion 45b and the projection 41c are positioned substantially on opposite sides of the axis 20x, while the one stop face 44a and the corresponding stop recess 44b of the retaining ring 44 which determine the lock position of the L-R lock knob 42 are correspondingly positioned substantially on the opposite sides of the axis 20x of the rotational shaft 20 in a radial direction thereof, and the other stop face 44a and the other corresponding stop recess 44b of the retaining ring 44 which determine the unlock position of the L-R lock knob 42 are correspondingly positioned substantially on the opposite sides of the axis 20x of the rotational shaft 20 in a radial direction thereof. In short, the retaining ring 44 is held elastically between the projection 41c and the free end portion 45b (which are formed on the integral member including the first rotating member 41 and the L-R lock knob 42) in a direction perpendicular to the axis 20x. According to this structure, when the integral member including the first rotating member 41 and the L-R lock knob 42 is positioned at the lock position or the unlock position thereof, play between the rotational shaft 20 and the retaining ring 44 in a direction perpendicular to the axis 20x is prevented from occurring while the retaining ring 44 is stably held, since the circular arc face 44e of the retaining ring 44 is pressed against the arc face 41e of the projection 41c by a spring force of the free end portion 45b that is applied to the retaining ring 44 in the direction shown by the arrow P.

As can be understood from the above descriptions, according to the first embodiment of the steering device 13 of the endoscope 10, the integral member including the first rotating member 41 and the L-R lock knob 42 can be prevented from coming off the rotational shaft 20 while the stopping position of rotation of the integral member including the first rotating member 41 and the L-R lock knob 42 can be controlled with a simple mechanism. Moreover, the retaining ring 44 is held on the rotational shaft stably by a simple mechanism.

The present invention is not limited solely to the above illustrated embodiment. For instance, the mechanism for preventing the integral member comprised of including the first rotating member 41 and the L-R lock knob 42 from coming off the upper end of the rotational shaft 20 and for controlling the stopping position in rotation of the integral member comprised of including the first rotating member 41 and the L-R lock knob 42 to stop with a click at each of the lock position and the unlock position can be applied to not only an endoscope but also any other devices. Although the illustrated embodiment of such a mechanism provides the integral member comprised of including the first rotating member 41 and the L-R lock knob 42 with the predetermined two stopping positions, i.e., the lock position and the unlock position, the mechanism can be modified to provide only one stopping position for one of the lock position and the unlock position. In this case, a retaining member which corresponds to the retaining ring 44 needs to be provided with only one stop face and a corresponding stop recess which corresponds to one stop face 44a and the corresponding stop recess 44b of the retaining ring 44, respectively. Alternatively, the mechanism can be modified to provide more than two stopping positions. In this case, a retaining member which corresponds to the retaining ring 44 only simply needs to be provided with more than two stop faces and corresponding more than two stop recesses.

Another feature of the first embodiment of the control device of the endoscope 10 is that the locking force of the locking device for fixing the bendable portion 12a can be easily adjusted. As has been described, in the L-R steering device 13LR, the L-R angle knob 23 is locked by pressing the first friction pad 46b of the axially-movable lock member 46, which is positioned in the L-R angle knob 23, against the second friction pad 48a, and the L-R angle knob 23 is unlocked by disengaging the first friction pad 46b from the second friction pad 48a. The axially-movable lock member 46 is moved by manually rotating the integral member including the first rotating member 41 and the L-R lock knob 42, which is coaxial to the L-R angle knob 23. In a state where the L-R angle knob 23 is locked with the locking device for the L-R steering device 13LR, the bendable portion 12a is locked to a given curved shape in a left or right direction.

As has been described, the locking force by the locking device for the L-R steering device 13LR can be adjusted by adjusting the position of the axially-immovable lock member 48 in the vertical direction as viewed in FIG. 2 (i.e., in the direction of the axis 20x of the rotational shaft 20). Namely, by adjusting the initial space between the first friction pad 46b on the axially-immovable lock member 46 and the second friction pad 48a on the axially-immovable lock member 48 in the direction of the axis 20x of the rotational shaft 20. The axially-immovable lock member 48 is coupled to the inner control shaft 21 with the female thread 48b thereof being engaged with the male thread 21e that is fixed relative to the L-R angle knob 23, so that the axially-immovable lock member 48 moves in the direction of the axis 20x of the rotational shaft 20 if the axially-immovable lock member 48 is rotated with the L-R angle knob 23 being locked.

Figure 17:
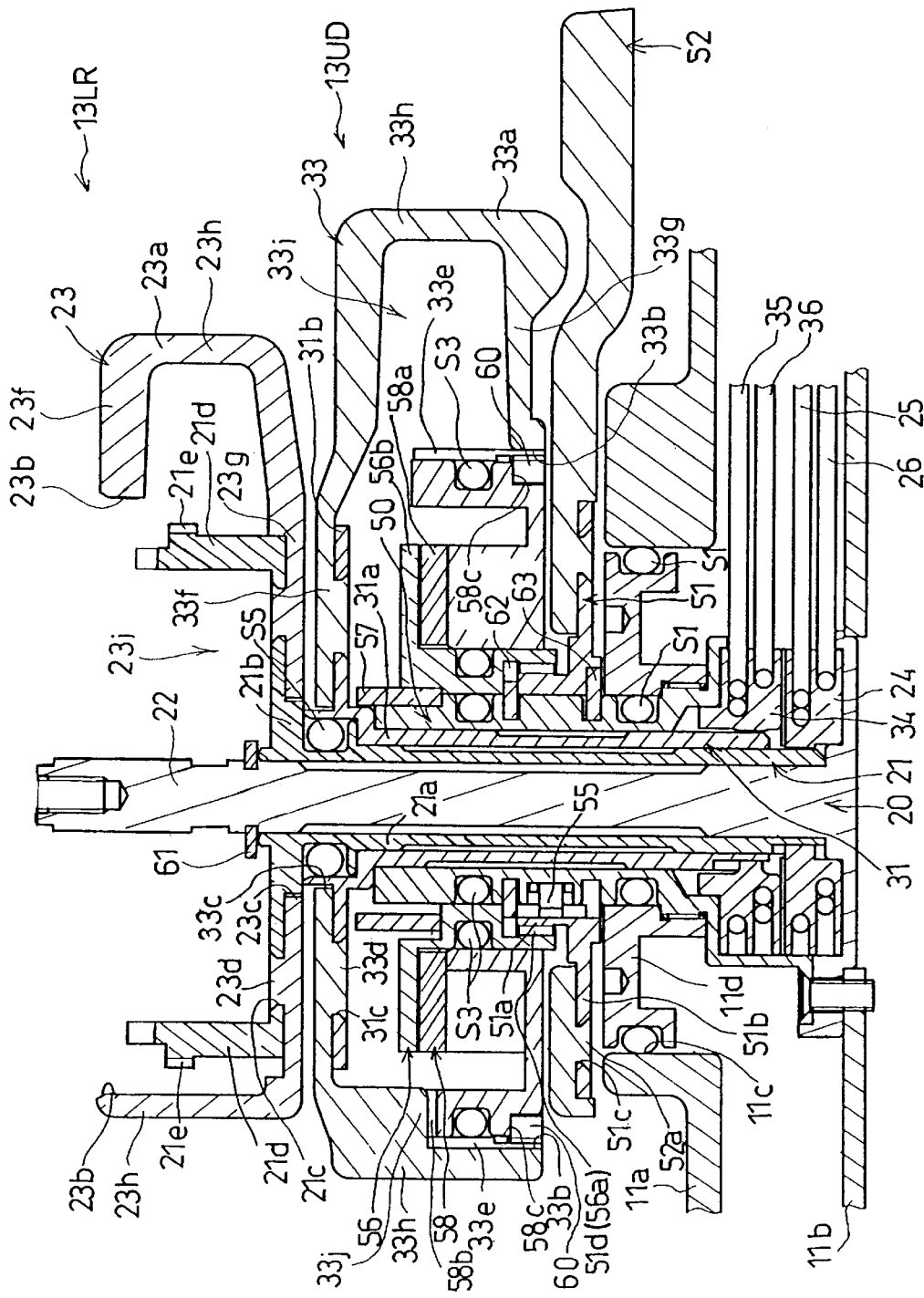
FIG. 17 is a cross sectional view of fundamental elements of the control device shown in FIG. 2 explaining the process of disassembling the control device.

As shown in FIGS. 12 and 17, the L-R angle knob 23 is a bottomed hollow substantially cylindrical member having an inner space 23i which includes upper and lower walls 23f and 23g and a connecting wall 23h. The upper and lower walls 23f and 23g extend substantially perpendicular to the axis 20x of the rotational shaft 20, while the connecting wall 23h extends substantially parallel to the axis 20x of the rotational shaft 20 to connect the upper wall 23f with the lower wall 23g. The lower wall 23g is provided with the aforementioned small aperture 23c having the center coaxial to the axis 20x of the rotational shaft 20. The disk portion 21b of the inner control shaft 21 is fitted in the small aperture 23c. The upper wall 23f has a narrow radial width (the length in radial directions as viewed in FIG. 10) except for that portion of the upper wall 23f which forms the aforementioned four projecting portions 23a of the L-R angle knob 23 since the top of the L-R angle knob 23 has a wide opening which forms the large aperture 23b via which the inner space 23i has a communicative connection with the outside of the L-R angle knob 23 (see FIG. 12). The center of the large circular aperture 23b is coaxial to the axis 20x of the rotational shaft 20.

An upper outer edge of the axially-immovable lock member 48 is exposed upwards to the outside of the L-R angle knob 23 via the large aperture 23b. The axially-immovable lock member 48 is provided, on the exposed upper outer edge thereof on radially opposite sides of the rotational shaft 20, with a pair of engaging holes 48c in which a pair of pins 75b provided on a pin face wrench 75 shown in FIG. 10 can be engaged. The male thread 21e, the axially-immovable lock member 48, the female thread 48b, and the pair of engaging holes 48c constitute an adjusting device (locking force adjusting device). Accordingly, the axially-immovable lock member 48 can be rotated about the axis 20x relative to the L-R angle knob 23 with such a pin face wrench without disassembling the L-R steering device 13LR. Accordingly, the locking force of the locking device for the L-R steering device 13LR can be easily adjusted without disassembling the L-R steering device 13LR.

In the illustrated embodiment of the locking device for the L-R steering device 13LR, even though the integral member including the first rotating member 41 and the L-R lock knob 42, which is operated to move the axially-movable lock member 46, is positioned so as to face and cover the upper large aperture 23b, the axially-immovable lock member 48 can be rotated without removing the integral member including the first rotating member 41 and the L-R lock knob 42.

More specifically, in the illustrated embodiment of the locking device for the L-R steering device 13LR, although the fixing ring 43 is positioned in the outermost region of the locking device in a radial direction about the rotational axis 20, the inner diameter of the large aperture 23b of the L-R angle knob 23 is greater than the outer diameter of the fixing ring 43, to therefore provide an annular gap T1 (see FIG. 10) between the outer edge of the fixing ring 43 and the inner peripheral surface of the large aperture 23b of the L-R angle knob 23. The pair of holes 48c are formed to be exposed to the outside of the L-R angle knob 23 via the large aperture 23b so as to be positioned in the annular gap T1. Therefore, the pair of holes 48c are not covered by the integral member including the first rotating member 41 and the L-R lock knob 42 even in a state where it is mounted to the rotational shaft 20, which makes it possible for the axially-immovable lock member 48 to be rotated about the axis 20x relative to the L-R angle knob 23 via the large aperture 23b.

Figure 10:
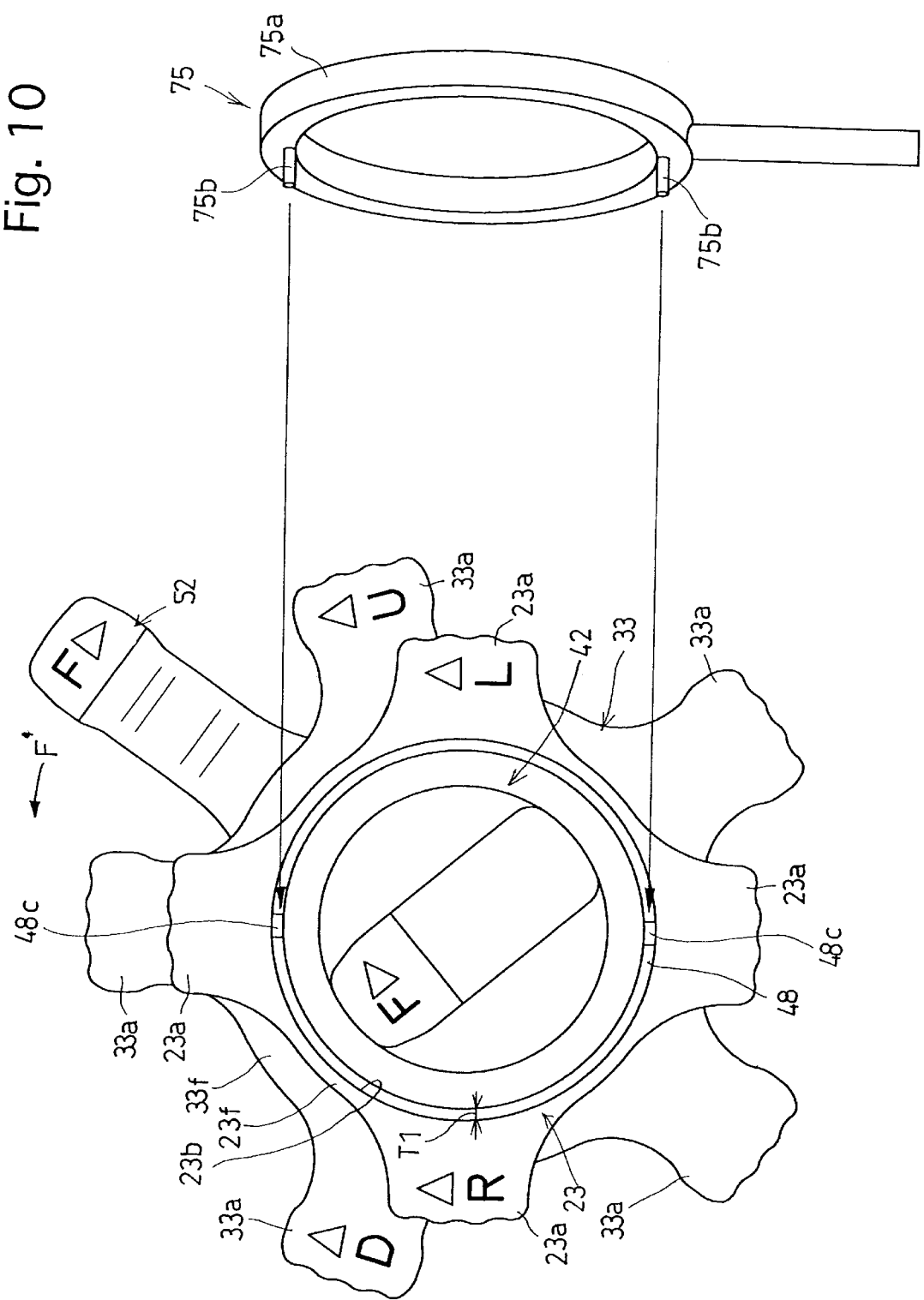
FIG. 10 shows a plan view of the control device of the endoscope shown in FIG. 1 and a perspective view of a pin face wrench which is used when the locking force of a locking device for the L-R steering device is adjusted, showing how to engage a pair of pins of the pin face wrench with a pair of engaging holes formed on an axially-immovable lock member of the control device.

The locking force by the locking device for the L-R steering device 13LR is adjusted with the pin face wrench 75 shown in FIG. 10. Alternatively, a similar pin face wrench can be used instead of the pin face wrench 75. The pin face wrench 75 is provided with a ring portion 75a from which the pair of pins 75 project. The pair of pins 75 are positioned on the ring portion 75a to be engageable with the pair of holes 48c. The inner diameter of the ring portion 75a is determined larger than the outer diameter of the fixing ring 43 so as not to interfere with the integral member including the first rotating member 41 and the L-R lock knob 42. In order to adjust the locking force of the locking device for the L-R steering device 13LR, the ring portion 75a is placed over the upper wall 23f of the L-R angle knob 23, and at the same time, the pair of pins 75b are respectively inserted into the pair of engaging holes 48c (see FIG. 10). In this state of engagement of the pair of pins 75b with the pair of engaging holes 48c, turning the pin face wrench 75 while holding the L-R angle knob 23, so that the L-R angle knob does not be rotated together with the axially-immovable lock member 48, causes the axially-immovable lock member 48 to rotate relative to the outer cylindrical portion 21d of the inner control shaft 21 via the pair of pins 75b and the pair of holes 48c. At this time, the axially-immovable lock member 48 moves along the axis 20x of the rotational shaft 20 while rotating relative to the L-R angle knob 23 due to the engagement of the female thread 48b with the male thread 21e. According to the movement of the axially-immovable lock member 48 along the axis 20x, the locking force of the locking device for the L-R steering device 13LR, at the time the L-R lock knob 42 is turned to the lock position thereof, can be adjusted. After the axially-immovable lock member 48 has been turned to a position where a desired locking force is obtained, the pin face wrench 75 is removed from the upper wall 23f of the L-R angle knob 23. After the pin face wrench 75 is removed, since the axially-immovable lock member 48 rotates together with the L-R angle knob 23 when the L-R angle knob 23 is manually turned, the L-R steering device 13LR can be controlled (e.g., can be half-locked) with a prescribed locking force applied to the L-R angle knob 23 without the need for any complicated operations.

As can be understood from the above descriptions, in the L-R steering device 13LR, the large aperture 23b is formed on the L-R angle knob 23, while the axially-immovable lock member 48, which is an element utilized for adjusting the locking force applied to the L-R angle knob 23 via the large aperture 23b, is structured to be manually rotated, so that the locking force of the locking device for the L-R steering device 13LR can be easily adjusted without removing the integral member including the first rotating member 41 and the L-R lock knob 42 when the locking force of the locking device for the L-R steering device 13LR needs to be adjusted.

Several sealing elements (the second and fourth sealing member groups S2 and S4) are disposed in gaps formed in the locking device for the L-R steering device 13LR to prevent any fluid from entering into the inner space 23i via the large aperture 23b. For instance, an annular sealing member in the second sealing member group is disposed in a gap between an outer peripheral surface of the axially-immovable lock member 48 and an inner peripheral surface of the large aperture 23b of the connecting wall 23h. With this structure, any foreign matter (e.g., water, moisture, dust and the like) is prevented from entering into the steering device 13. Therefore, even if the endoscope 10 is immersed in a chemical solution, the solution is completely prevented from entering into the hollow L-R angle knob 23.

As shown in FIG. 12, the axially-movable lock member 46 and the axially-immovable lock member 48 are positioned in the large aperture 23b of the L-R angle knob 23 so that the upper face of the axially-movable lock member 46 and the axially-immovable lock member 48 are substantially flush with respect to each other and are substantially flush with the upper face of the upper wall 23f of the L-R angle knob 23, while the pair of holes 48c, which is used to rotate the axially-immovable lock member 48 with the pin face wrench 75, are recessed inwards (i.e., downward as viewed in FIG. 12). Accordingly, since no part of the axially-immovable lock member 48 largely projects outward from the L-R angle knob 23, there is no likelihood of part of the axially-immovable lock member 48 getting snagged on something during operation of the endoscope 10 to cause the axially-immovable lock member 48 to rotate to thereby vary the locking force applied to the L-R angle knob 23 accidentally.

The U-D steering device 13UD will be hereinafter discussed. In the U-D steering device 13UD, the U-D angle knob 33 is locked by moving the axially-movable lock member 56, which is positioned in the U-D angle knob 33, in the direction of the axis of the stationary hollow cylindrical base 50 so as to press the first friction pad 56b of the axially-movable lock member 56 against the second friction pad 58a, and the U-D angle knob 33 is unlocked by moving the axially-movable lock member 56 in the opposite direction so as to disengage the first friction pad 56b from the second friction pad 58a. The axis of the stationary hollow cylindrical base 50 is coincident with the axis 20x of the rotational shaft 20.

The mechanism for adjusting the locking force by the locking device for the U-D steering device 13UD is different from the mechanism for adjusting the locking force by the locking device for the L-R steering device 13LR. The U-D angle knob 33 is provided with five projections 33j (see FIGS. 6 and 15) each of which projects radially inwards in an inner space 33i of the U-D angle knob 33 to be engaged in a corresponding recess 58b formed on the axially-immovable lock member 58 (see FIG. 15). Only one of the five recesses 58b are shown in FIG. 15. In a state where the five projections 33j are respectively engaged in the five recesses 58b, the axially-immovable lock member 58 is movable in the direction of the axis 20x of the rotational shaft 20 relative to the U-D angle knob 33, and is not rotatable about the axis 20x relative to the U-D angle knob 33. Therefore, although the axially-immovable lock member 58 rotates together with the U-D angle knob 33 when the U-D angle knob 33 is turned, the axially-immovable lock member 58 can be moved in the direction of the axis 20x relative to the U-D angle knob 33.

A lower outer edge of the axially-immovable lock member 58 is exposed to the outside of the U-D angle knob 33 via the large aperture 33b. The axially-immovable lock member 58 is provided, on the exposed lower outer edge thereof on radially opposite sides of the rotational shaft 20, with an annular recessed portion 58c in which the aforementioned adjusting ring 60, which is provided as a member separate from the axially-immovable lock member 58, is positioned. As has been described, the female thread 33k formed on an inner peripheral surface of the metal ring 33e is in mesh with the male thread 60a formed on an outer peripheral surface of the adjusting ring 60. Therefore, the adjusting ring 60 moves in the direction of the axis 20x via the male thread 60a and the female thread 33k if rotated relative to the metal ring 33e. This movement of the adjusting ring 60 in the direction of the axis 20x causes the axially-immovable lock member 58 to move in the same direction. For instance, if the adjusting ring 60 is rotated in a predetermined rotational direction to move upward with respect to FIG. 2, the axially-immovable lock member 58 also moves upward. This upward movement of the axially-immovable lock member 58 reduces the initial space between the first friction pad 56b on the axially-immovable lock member 56 and the second friction pad 58a on the axially-immovable lock member 58 to thereby increase the locking force applied to the U-D angle knob 33 when the L-R lock knob 42 is positioned at the lock position thereof. Conversely, if the adjusting ring 60 is rotated in the other predetermined rotational direction to move downward with respect to FIG. 2, the axially-immovable lock member 58 also moves downward. This downward movement of the axially-immovable lock member 58 increases the initial space between the first friction pad 56b on the axially-immovable lock member 56 and the second friction pad 58a on the axially-immovable lock member 58 to thereby decrease the locking force applied to the U-D angle knob 33 when the L-R lock knob 42 is positioned at the lock position thereof.

Figure 15:
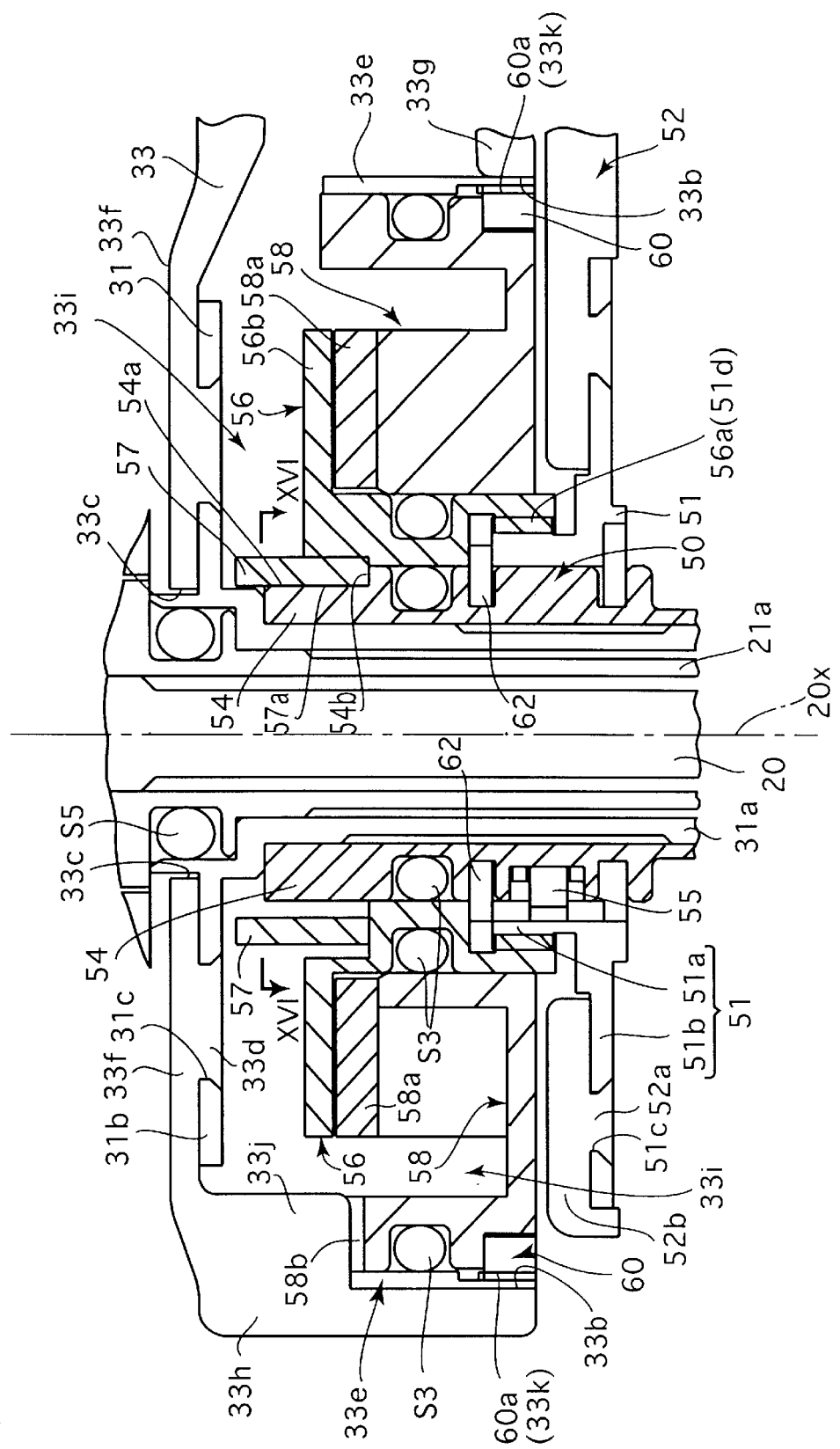
FIG. 15 is a cross sectional view of fundamental elements of the locking device for the U-D steering device and peripheral elements thereof.

As shown in FIG. 15 or 17, the U-D angle knob 33 is an inverted bottomed substantially cylindrical hollow member having the inner space 33i which includes upper and lower walls 33f and 33g and a connecting wall 33h. The upper and lower walls 33f and 33g extend substantially perpendicular to the axis 20x of the rotational shaft 20, while the connecting wall 33h extends substantially parallel to the axis 20x of the rotational axis 20 to connect the upper with the lower walls 33f and 33g. The upper wall 33f is provided with the aforementioned small aperture 33c having a center coaxial to the axis 20x of the rotational shaft 20. Part of the disk portion 31b is fitted in the small aperture 33c. The lower wall 33g has a narrow radial width (the length in a radial direction as viewed in FIG. 11) except for the portion of the lower wall 33g which forms the aforementioned five projecting portions 33a of the U-D angle knob 33, since the bottom of the U-D angle knob 33 is widely open to form the large aperture 33b via which the inner space 33i has a communicative connection with the outside of the U-D angle knob 33 (see FIG. 15). The center of the large circular aperture 33b is coaxial to the axis 20x of the rotational shaft 20.

A lower outer part of the axially-immovable lock member 58 and also the lower face of the adjusting ring 60 are exposed downwards to the outside of the U-D angle knob 33 via the large aperture 33b. The adjusting ring 60 is provided, on the exposed lower face thereof on radially opposite sides of the rotational shaft 20, with a pair of engaging holes 60b in which a pair of pins 76b provided on a pin face wrench 76, shown in FIG. 11, can be engaged. The female thread 33k, the adjusting ring 60, the male thread 60a, and the pair of engaging holes 60b constitute an adjusting device (locking force adjusting device). Therefore, the adjusting ring 60 can be rotated about the axis 20x relative to the U-D angle knob 33 with such a pin face wrench without disassembling the U-D steering device 13UD. Accordingly, the locking force of the locking device for the U-D steering device 13UD can be easily adjusted without disassembling the U-D steering device 13UD.

In the illustrated embodiment of the locking device for the U-D steering device 13UD, even though the integral member including the first rotating member 51 and the U-D lock lever 52, which is operated to move the axially-movable lock member 56, is positioned so as to face and cover the large aperture 33b, the axially-immovable lock member 58 can be rotated without removing the integral member including the first rotating member 51 and the U-D lock lever 52. More specifically, in the illustrated embodiment of the locking device for the U-D steering device 13UD, although the outer edge of a disc portion 52b (see FIGS. 11 and 15)of the U-D lock lever 52 is positioned in the outermost region of the locking device in a radial direction about the rotational axis 20 except for an elongated lever portion 52c of the U-D lock lever 52, the inner diameter of the large aperture 33b of the U-D angle knob 33 is greater than the outer diameter of the disc portion 52b of the U-D lock lever 52 so as to provide an annular gap T2 (see FIG. 11) between the outer edge of the disc portion 52b and the inner peripheral surface of the large aperture 33b of the U-D angle knob 33. The pair of holes 60b of the adjusting ring 60 are formed to be exposed to the outside of the U-D angle knob 33 via the large aperture 33b so as to be positioned in the annular gap T2. Therefore, the pair of holes 60b are not covered by the integral member including the first rotating member 51 and the U-D lock lever 52 even in a state where it is mounted to the cylindrical base 50, which makes it possible for the axially-immovable lock member 58 to be rotated about the axis 20x relative to the U-D angle knob 33 via the large aperture 33b.

Figure 11:
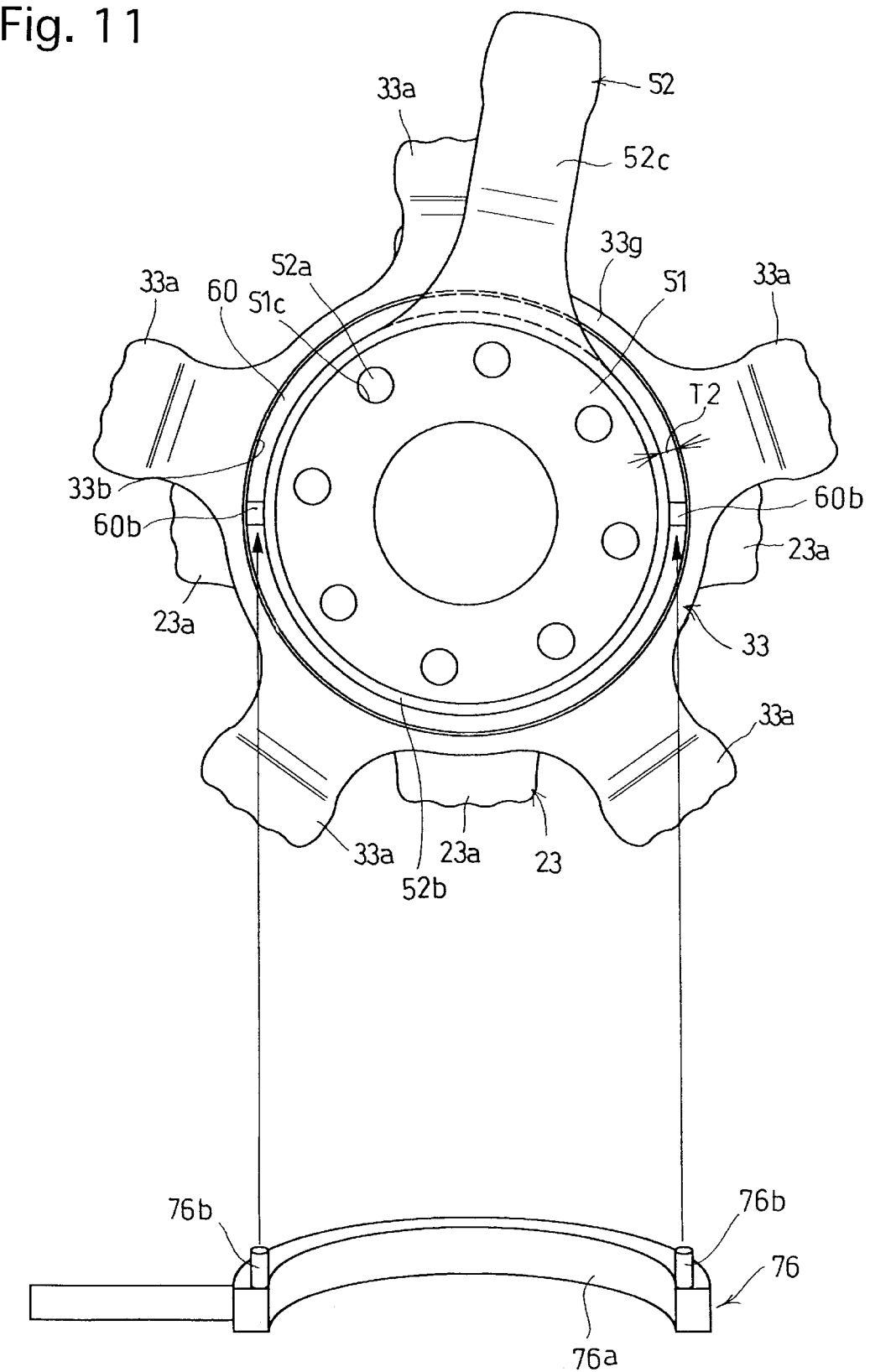
FIG. 11 shows a bottom view of fundamental elements of the control device of the endoscope shown in FIG. 1 and a perspective view of another pin face wrench which is used when the locking force of a locking device for the U-D steering device is adjusted, showing how to engage a pair of pins of the another pin face wrench with a pair of engaging holes formed on an adjusting ring of the control device.

The locking force by the locking device for the U-D steering device 13UD is adjusted with the pin face wrench 76 shown in FIG. 11. Of course, a similar pin face wrench can be used instead of the pin face wrench 76. The pin face wrench 76 is provided with a semi-ring portion 76a from which the pair of pins 76 projects. The pair of pins 76 are positioned on the semi-ring portion 76a to be engageable with the pair of holes 60b. In order to adjust the locking force of the locking device for the U-D steering device 13UD, the semi-ring portion 76a is inserted into a gap between the housing 11a and the U-D steering device 13UD, and subsequently the pair of pins 76b are respectively inserted into the pair of engaging holes 60b (see FIG. 11). In this state of engagement of the pair of pins 76b with the pair of engaging holes 60b, turning the pin face wrench 76 while holding the U-D angle knob 33 so that the U-D angle knob does not rotate together with the axially-immovable lock member 58 causes the axially-immovable lock member 58 to rotate relative to the metal ring 33e via the pair of pins 76b and the pair of holes 60b. At this time, the axially-immovable lock member 58 moves along the axis 20x of the rotational shaft 20 while rotating relative to the U-D angle knob 33 due to the engagement of the female thread 33k with the male thread 60a. Due to the movement of the axially-immovable lock member 58 along the axis 20x relative to the U-D angle knob 33, the locking force of the locking device for the U-D steering device 13UD can be adjusted at the time the U-D lock lever 52 is turned to the lock position thereof. After the axially-immovable lock member 58 has been turned to a position where a desired locking force is obtained, the pin face wrench 76 is removed. After the pin face wrench 76 is removed, since the axially-immovable lock member 58 rotates together with the U-D angle knob 33 when the U-D angle knob 33 is manually turned, the U-D steering device 13UD can be controlled (e.g., can be half-locked) with a prescribed locking force applied to the U-D angle knob 33 without the need for any complicated operations.

As can be understood from the above descriptions, similar to the L-R steering device 13LR, in the U-D steering device 13UD, the large aperture 33b is formed on the U-D angle knob 33, while the axially-immovable lock member 58, which is an element utilized for adjusting the locking force applied to the U-D angle knob 33 via the large aperture 33b, is structured so as to be manually rotated, so that the locking force of the locking device for the U-D steering device 13UD can be easily adjusted without removing the integral member including the first rotating member 51 and the U-D lock lever 52 when the locking force of the locking device for the U-D steering device 13UD needs to be adjusted.

Several sealing elements (the third sealing member group S3) are disposed in gaps formed in the locking device for the U-D steering device 13UD to prevent any fluid from entering into the inner space 33i via the large aperture 33b. Therefore, even if the endoscope 10 is immersed in a chemical solution, the solution is completely prevented from entering into the hollow U-D angle knob 33.

As shown in FIGS. 15 and 17, the axially-immovable lock member 58 and the adjusting ring 60 are positioned in the large aperture 33b of the U-D angle knob 33 so that the lower face of the axially-immovable lock member 58 and the adjusting ring 60 is substantially flush with the lower face of the lower wall 33g of the U-D angle knob 33, while the pair of holes 60b, which is used to rotate the axially-immovable lock member 58 with the pin face wrench 76, are recessed inwards (i.e., upward as viewed in FIG. 15). Accordingly, since any part of the axially-immovable lock member 58 or the adjusting ring 60 does not largely project outward from the U-D angle knob 33, there is no possibility of part of the axially-immovable lock member 58 or part of the adjusting ring 60 getting snagged on something during operation of the endoscope 10 to cause the axially-immovable lock member 58 to rotate to thereby vary the locking force applied to the U-D angle knob 33 accidentally.

In the steering device 13, the L-R angle knob 23 of the L-R steering device 13LR and the U-D angle knob 33 of the U-D steering device 13UD are positioned adjacent to each other in the direction of a common axis (i.e., the axis 20x of the rotational shaft 20), the large aperture 23b of the L-R angle knob 23 is open upwards, and the large aperture 33b of the U-D angle knob 33 is open downwards. The reduction in size of the steering device 13 is achieved with such an arrangement of the large aperture 23b and the large aperture 33b that are formed to be open in opposite directions so as not to face each other. More specifically, the reduction in size of the steering device 13 is achieved with such an arrangement because it is not necessary to make a wide gap between the lower wall 23g of the L-R angle knob 23 and the upper wall 33f of the U-D angle knob 33 for the pin face wrench 75 or 76 to be inserted into such a gap, which makes it possible to position the L-R angle knob 23 and the U-D angle knob 33 closely to each other with a minimum gap between the lower wall 23g and the upper wall 33f. Accordingly, with such an arrangement the steering device 13 can be made smaller in the direction of the axis 20x of the rotational shaft 20.

A method of disassembling the steering device 13 will be hereinafter discussed with reference to FIGS. 2 and 17 through 20. In order to disassemble the steering device 13 from a state shown in FIG. 2, firstly the fixing ring 43 is removed and subsequently the L-R lock knob 42 is removed from the first rotating member 41. In this state the set screw 20a is exposed to the outside of the endoscope 10. After the set screw 20a is removed from the upper end of the rotational shaft 20, an assembly of fundamental elements (e.g., the first rotating member 41, the axially-immovable lock member 48 and the axially-movable lock member 46) of the locking device of the L-R angle knob 23 can be dismounted upward with respect to FIG. 2 from the steering device 13 via the large aperture 23b of the L-R angle knob 23 since the large aperture 23b is open toward the upper end of the rotational shaft 20. When such an assembly is dismounted, the assembly is removed upward with respect to FIG. 2 while being rotated about the rotational shaft 20 in order to release the engagement of the female thread 48b of the axially-immovable lock member 48 with the aforementioned male thread 21e of the inner control shaft 21. When the assembly of the locking device of the L-R angle knob 23 is dismounted, the second sealing member group S2 is dismounted together with the assembly. After the assembly of the locking device of the L-R angle knob 23 is dismounted, the assembly itself can be disassembled by releasing the engagement of the male thread 41d of the first rotating member with the female thread 46a of the axially-movable lock member 46.

The retaining member 47, which has a generally hexagonal section as shown in FIG. 5, can be removed from the non-cylindrical portion 22 of the rotational shaft 20 in a direction perpendicular to the axis 20x of the rotational shaft 20 after the assembly of the locking device of the L-R angle knob 23 is dismounted. FIG. 17 shows a state of the steering device 13 where fundamental elements of the locking device for locking the L-R angle knob 23 which include the first rotating member 41, the L-R lock knob 42, the axially-immovable lock member 48 and the axially-movable lock member 46 are dismounted from the steering device 13 before the retaining member 47 is disengaged from the rotational shaft 20. In this state, the retaining member 61 remains engaged with the rotational shaft 20.

At the disassembly stage shown in FIG. 17, most of the elements of the steering device 13 which are positioned below the retaining member 61 can be dismounted after the retaining member 61 is removed from the rotational shaft 20. Similar to the retaining member 47, the retaining member 61 can be removed from the rotational shaft 20 in a direction perpendicular to the axis 20x of the rotational shaft 20. After the retaining member 61 is removed from the rotational shaft 20 in a state shown in FIG. 17, firstly the integral member including the inner control shaft 21 and the L-R angle knob 23 of the L-R steering device 13LR is dismounted from the rotational shaft 20 upwards with respect to FIG. 17. At this stage, the fifth sealing member group S5 is removed together with the integral member including the inner control shaft 21 and the L-R angle knob 23. The lower end of the cylindrical shaft portion 21a of the inner control shaft 21 is fitted in the first pulley 24 to be engaged therewith in a manner so that the cylindrical shaft portion 21a does not rotate about the axis 20x relative to the first pulley 24 (i.e., rotates about the axis 20x together with the first pulley 24 about the axis 20x) when the rotational shaft 20 rotates, and the cylindrical shaft portion 21a can be pulled out of the first pulley 24 in the direction of the axis 20x of the rotational shaft 20.

Figure 18:
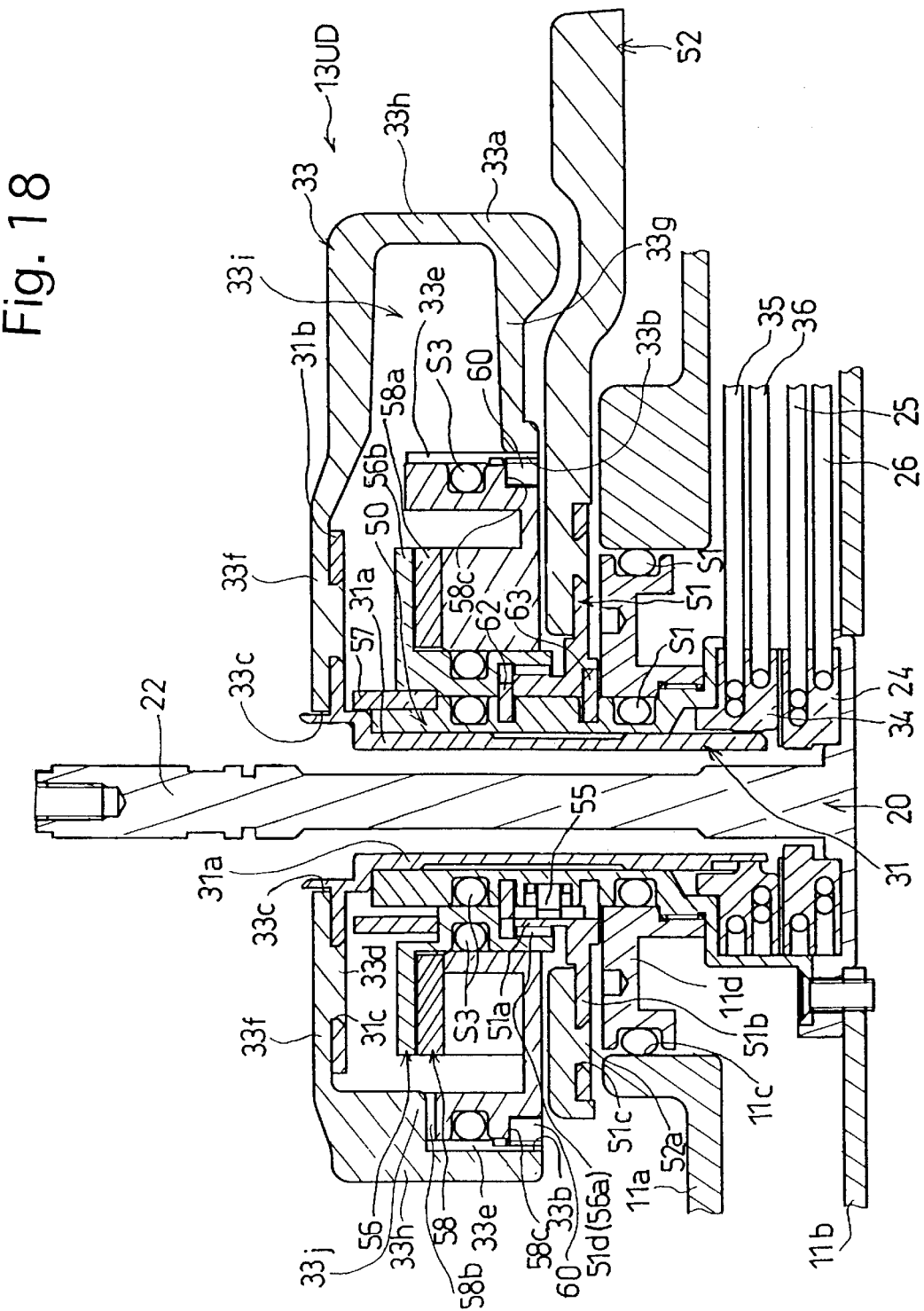
FIG. 18 is a cross sectional view of fundamental elements of the control device shown in FIG. 2 explaining the process of disassembling the control device.

FIG. 18 shows a state of the steering device 13 where the retaining member 61 and the integral member including the inner control shaft 21 and the L-R angle knob 23 of the L-R steering device 13LR are dismounted from the steering device 13. Subsequently, the U-D steering device 13UD can be dismounted in a state shown in FIG. 18. In order to further disassemble the steering device 13 in a state shown in FIG. 18, firstly the integral member including the outer control shaft 31 and the U-D angle knob 33 is removed after the adjusting ring 60 is removed. At this time, for instance, turning the U-D angle knob 33 while holding the adjusting ring 60 with the pin face wrench 76 so that the adjusting ring 60 does not rotate together with the U-D angle knob 33 causes the male thread 60a of the adjusting ring 60 to be disengaged from the female thread 33k of the U-D angle knob 33. After the adjusting ring 60 is removed, the integral member including the outer control shaft 31 and the U-D angle knob 33 is pulled out of the stationary hollow cylindrical base 50 upward as viewed in FIG. 18. Since the large aperture 33b of the U-D angle knob 33 is open downwards so as to allow the axially-movable lock member 56 and the axially-immovable lock member 58 to be removed from the inner space 33i of the U-D angle knob 33 via the large aperture 33b, the axially-movable lock member 56 and the axially-immovable lock member 58 are not interrupted by the integral member including the outer control shaft 31 and the U-D angle knob 33 when removed from the inner space 33i of the U-D angle knob 33. The lower end of the cylindrical shaft portion 31a of the outer control shaft 31 is fitted in the second pulley 34 to be engaged therewith in a manner so that the cylindrical shaft portion 31a does not rotate about the axis 20x relative to the second pulley 34 (i.e., rotates about the axis 20x together with the second pulley 34 about the axis 20x) when the rotational shaft 20 rotates, and the cylindrical shaft portion 31a can be pulled out of the second pulley 34 in the direction of the axis 20x of the rotational shaft 20.

Figure 19:
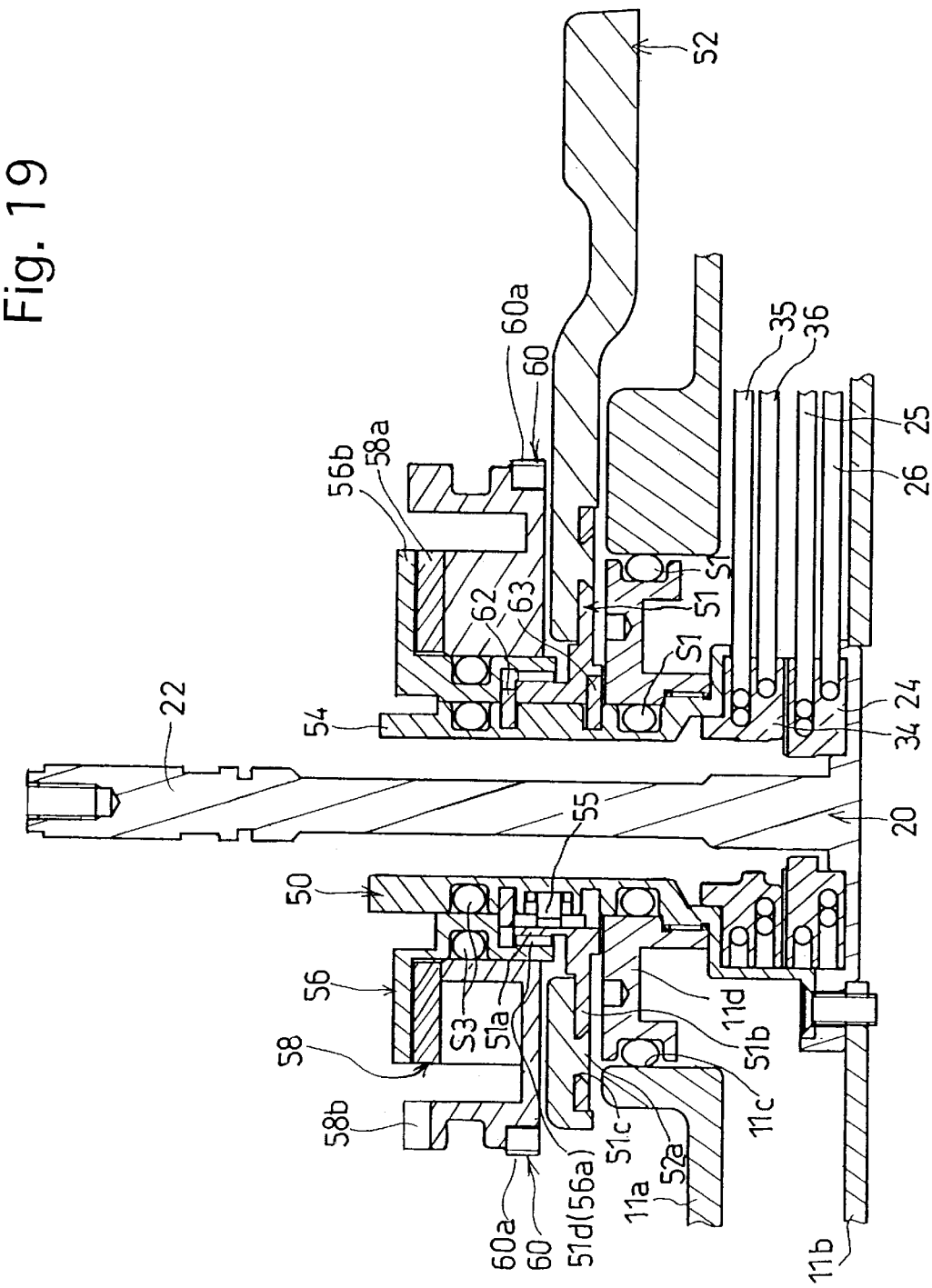
FIG. 19 is a cross sectional view of fundamental elements of the control device shown in FIG. 2 explaining the process of disassembling the control device.

FIG. 19 shows a state of the steering device 13 where the integral member including the outer control shaft 31 and the U-D angle knob 33 of the L-R steering device 13LR is removed from the steering device 13 shown in FIG. 18. In this state shown in FIG. 19, fundamental elements of the locking device for locking the U-D angle knob 33 can be removed. Firstly, the axially-movable lock member 56 is removed upward as viewed in FIG. 2 while being rotated about the rotational shaft 20. The axially-movable lock member 56 needs to be removed while being rotated about the rotational shaft 20 in order to release the engagement of the male thread 51d of the cylindrical portion 51a of the second rotating member 51 with the female thread 56a of the axially-movable lock member 56. After the axially-movable lock member 56 is removed, the axially-immovable lock member 58 and the adjusting ring 60 can be removed.

The integral member including the second rotating member 51 and the U-D lock lever 52 is prevented from moving in the direction toward the upper end of the stationary hollow cylindrical base 50 by a retaining member 62. The cylindrical base 50 is provided between the opposite ends thereof with an annular groove in which the retaining member 62 is fitted, and the angular range of rotation of the integral member including the second rotating member 51 and the U-D lock lever 52 is limited by a rotation limiting member 63. Each of the retaining member 62 and the rotation limiting member 63 can be inserted into and pulled out of the corresponding annular groove of the cylindrical base 50 in a direction perpendicular to the axis of the cylindrical base 50. If the axially-movable lock member 56 is removed from the cylindrical base 50 in the direction toward the upper end thereof in a state shown in FIG. 19, the retaining member 62 is exposed externally. Subsequently, if the retaining member 62 is removed from the cylindrical base 50, the integral member including the second rotating member 51 and the U-D lock lever 52 can be dismounted from the cylindrical base 50 in the direction toward the upper end of the stationary hollow cylindrical base 50. If the integral member including the second rotating member 51 and the U-D lock lever 52 is removed from the cylindrical base 50, the rotation limiting member 63 is exposed externally, so that the rotation limiting member 63 can be removed from the cylindrical base 50.

In short, when the steering device 13 is disassembled, the locking device for the locking the L-R angle knob 23, the L-R angle knob 23 (which is supported by the rotational shaft 20 on the upper end thereof), the U-D angle knob 33 (which is supported by the rotational shaft 20 on the lower end thereof, i.e., on the side of the housing 11a), and the locking device for the locking the U-D angle knob 33 are removed in that order.

Figure 20:
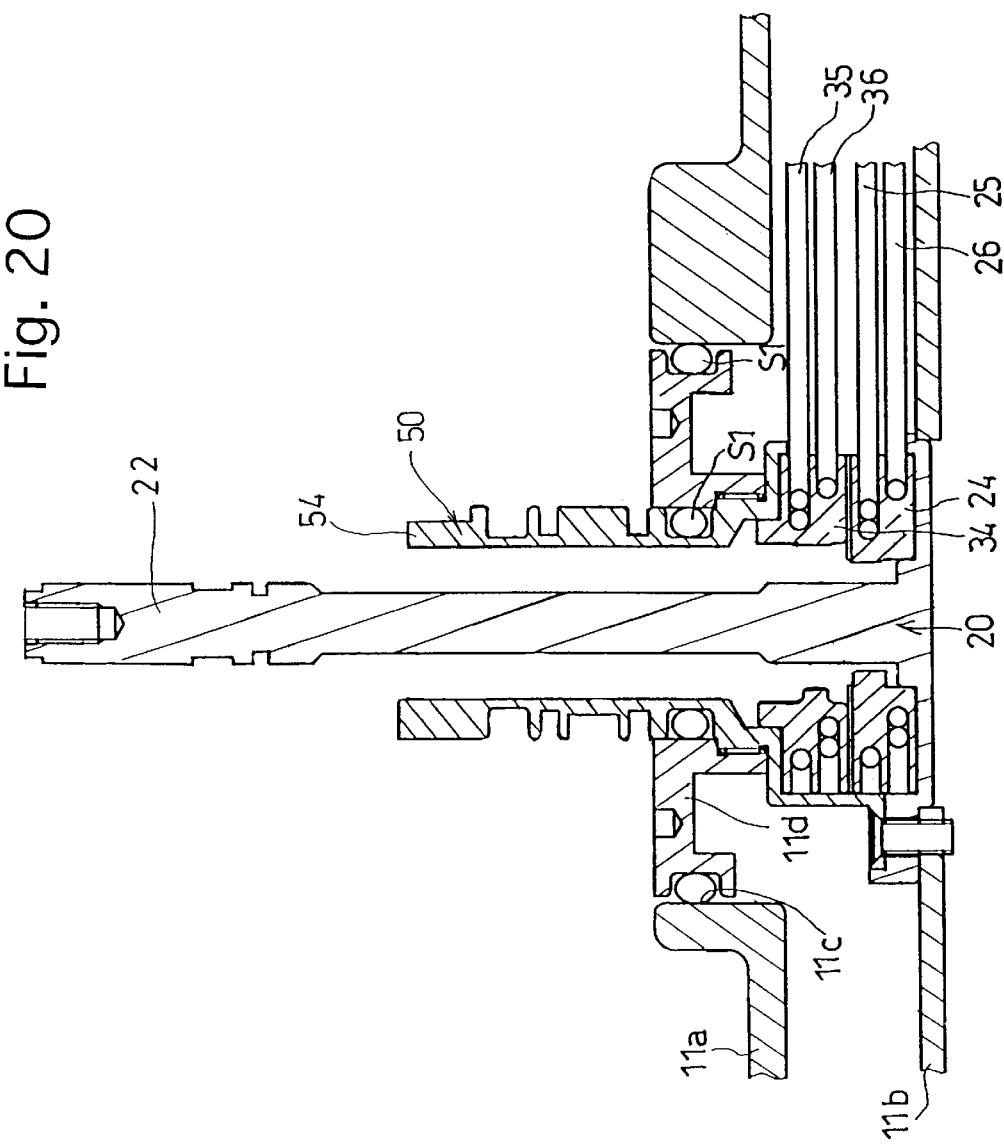
FIG. 20 is a cross sectional view of fundamental elements of the control device shown in FIG. 2 explaining the process of disassembling the control device.

After the U-D steering device 13UD is removed as shown in FIG. 20, the covering member 11d can be removed from the housing 11a, which is an element of the control body 11, if necessary. After the covering member 11d is removed from the housing 11a, the stationary hollow cylindrical base 50 and the rotational shaft 20 can be dismounted from the substrate 11b.

The method of assembling the steering device 13 is reverse to the above described method of disassembling the steering device 13. Since the method of disassembling the steering device 13 has been described in detail, the manner of assembling the steering device 13 will not be hereinafter discussed in detail. In brief, when the steering device 13 is reassembled, the locking device for the locking the U-D angle knob 33, the U-D angle knob 33, the L-R angle knob 23 and the locking device for the locking the L-R angle knob 23 are mounted in that order.

As can be understood from the above descriptions, in a state where the steering device 13 is in assembled condition, the upper large aperture 23b functions as an opening via which an adjusting mechanism (which includes the axially-immovable lock member 48) for adjusting the locking force by the locking device for the L-R steering device 13LR can be manually operated with the pin face wrench 75, while the lower large aperture 33b functions as an opening via which another adjusting mechanism (which includes the axially-immovable lock member 58) for adjusting the locking force by the locking device for the U-D steering device 13UD can be manually operated with the pin face wrench 76. On the other hand, when the steering device 13 is disassembled or assembled, the upper large aperture 23b functions as an opening via which fundamental elements (which includes the first rotating member 41, the axially-movable lock member 46, and the axially-immovable lock member 48) of the locking device for locking the L-R angle knob 23 are mounted to or dismounted from the inside of the hollow L-R angle knob 23, while the lower large aperture 33b functions as an opening via which fundamental elements (which includes the second rotating member 51, the axially-movable lock member 56, and the axially-immovable member 58) of the locking device for locking the U-D angle knob 33 are mounted to or dismounted from the inside of the hollow U-D angle knob 33. Accordingly, in a state where the steering device 13 is in assembled condition, the locking force generated by each of the aforementioned two locking devices can be easily adjusted via the upper or lower large aperture 23b or 33b. Moreover, fundamental elements (which includes the first rotating member 41, the axially-movable lock member 46, and the axially-immovable lock member 48) of the locking device for locking the L-R angle knob 23 can be removed from or mounted to the inner space 23i of the L-R angle knob 23 via the upper large aperture 23b without disassembling the L-R angle knob 23 when the L-R steering device 13LR is disassembled or assembled, which achieves outstanding efficiency in disassembling and assembling of the L-R steering device 13LR. Similarly, fundamental elements (which includes the second rotating member 51, the axially-movable lock member 56, and the axially-immovable lock member 58) of the locking device for locking the U-D angle knob 33 can be removed from or mounted to the inner space 33i of the U-D angle knob 33 via the lower large aperture 33b without disassembling the U-D angle knob 33 when the U-D steering device 13UD is disassembled or reassembled, which achieves outstanding efficiency in disassembling and reassembling of the U-D steering device 13UD.

As can be understood from the above descriptions, in the first embodiment of the control device of the endoscope 10, each angle knob (23 or 33) is formed as a hollow element having an opening (23i or 33i) via which the associated adjusting mechanism for adjusting the locking force by the corresponding locking device for the steering device (13LR or 13UD) can be manually operated with the pin face wrench 75 or 76, so that the locking force by either locking device can be adjusted easily without the need of disassembling the steering device.

Accordingly, according to the first embodiment of the control device of the endoscope 10, the locking force applied to each of the two angle knobs 22 and 23 can be easily adjusted via the corresponding opening (23i or 33i) without the need of disassembling the steering device.

The present invention is not limited solely to the above illustrated embodiment. For instance, although the a pair of angle knobs, i.e. the L-R angle knob 23 and the U-D angle knob 33, are disposed adjacent to each other in the direction of the axis 20x of the rotational shaft 20, the present invention can be applied to not only an endoscope having a pair of angle knobs but also any other endoscope having only one angle knob or more than two angle knobs. Furthermore, although a pair of engaging holes 48c or 60b is provided for adjusting the locking force by the locking device for the steering device 13LR or 13UD, respectively, the number of such engaging holes is not limited solely to two, but can be more than two. Further, such engaging holes can be modified in shape as long as the function thereof does not change.

FIGS. 21 through 29 show the second embodiment of the control device of the endoscope. Control device of the endoscope shown in FIGS. 21 through 25 corresponds to the above described first embodiment of the control device of the endoscope 10 but is different in structure from the above described first embodiment of the control device of the endoscope.

The second embodiment of the control device is provided above a housing 106 with a rotational shaft 103, an L-R steering portion 102, a U-D steering portion 104, an L-R lock operating portion 101 for locking the distal end of the endoscope in a left or right direction, a U-D lock operating portion 105 for locking the distal end of the endoscope in upward and downward directions, and a locking mechanism. The locking mechanism includes an L-R locking mechanism 107A for locking an L-R angle knob 102A of the L-R steering portion 102, and a U-D locking mechanism 107B for locking a U-D angle knob 104A of the U-D steering portion 104.

The L-R lock operating portion 101 is manually operated to lock the L-R angle knob 102A. An L-R lock knob 101A which is rotatably fitted on the rotational shaft 103, a cylindrical member 111 which is fixed to the L-R lock knob 101A, an upper lock cylinder 112 which is fixed to the cylindrical member 111 via a set screw 11A, an axially-movable lock member 113, and a friction pad 114 which is fixed to the axially-movable lock member 113 are fundamental elements of the L-R lock operating portion 101.

The cylindrical member 111 is fixed to the L-R lock knob 101A with a conventional fixing device such as set screws (not shown). A set screw 131 having a long cylindrical head is screwed into the upper end of the rotational shaft 103. The axially-movable lock member 113 is provided with a hollow cylindrical slide portion 113B having a square hole 113H which is slidably fitted on a square shaft end 103A formed at the upper end of the rotational shaft 103. The cylindrical member 111 is fitted on both the cylindrical head of the set screw 131 and the hollow cylindrical slide portion 113B of the axially-movable lock member 113 so as to be rotatable about the an axis L of the rotational shaft 103 relative to both the set screw 131 and the hollow cylindrical slide portion 113B when the L-R lock knob 101A is turned.

Figure 22:
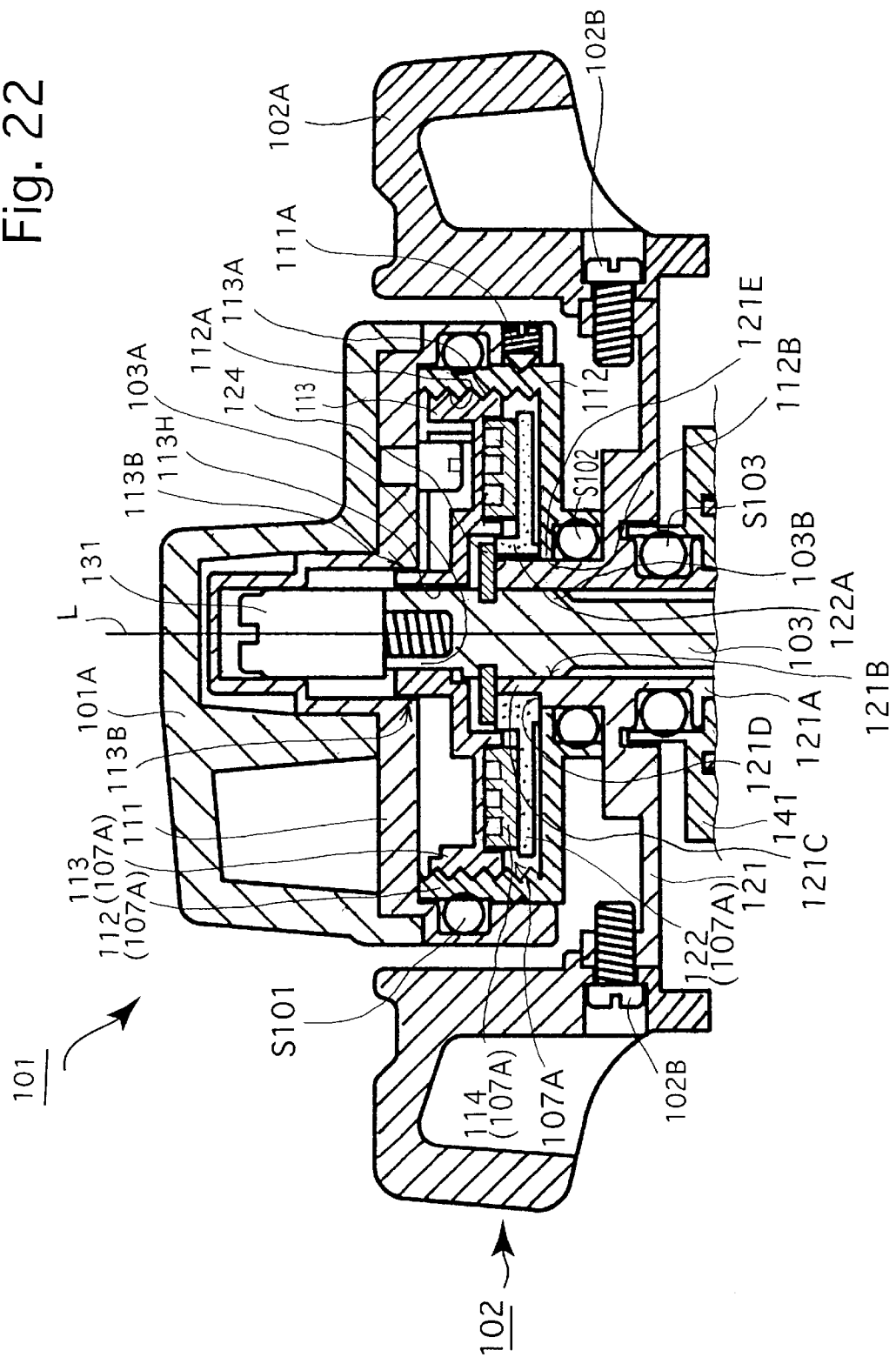
FIG. 22 is a cross sectional view of an upper half of the control device shown in FIG. 21.

The cylindrical member 111 is secured to the upper lock cylinder 112 via the set screw 111A after the position of the cylindrical member 111 relative to the upper lock cylinder 112 in the vertical direction as viewed in FIG. 22 (i.e., in the direction of the axis of the rotational shaft 103) is finely adjusted. With this structure, the L-R lock knob 101A and the upper lock cylinder 112 rotate together in the same rotational direction by the same angle of rotation when the L-R lock knob 101A is turned. The cylindrical member 111 can be rotated about the axis L of the rotational shaft 103 relative to the upper lock cylinder 112 if the set screw 111A is unscrewed. An O-ring S101 (see FIG. 22) is positioned between the cylindrical member 111 and the upper lock cylinder 112 to seal the gap therebetween in a watertight fashion.

The upper lock cylinder 112 is formed as a hollow cylindrical member, the upper end of which is open. The upper lock cylinder 112 is provided on an inner peripheral surface thereof with a female thread 112A. The upper lock cylinder 112 is further provided at a bottom center thereof with an opening 112B in which a cylindrical portion 121E of a first rotatable member 121 (see FIGS. 22 and 24) is fitted in a rotatable manner about the axis L of the rotational shaft 103. An O-ring S102 is positioned between the upper lock cylinder 112 and the first rotatable member 121 to seal the gap therebetween in a watertight fashion.

Figure 24:
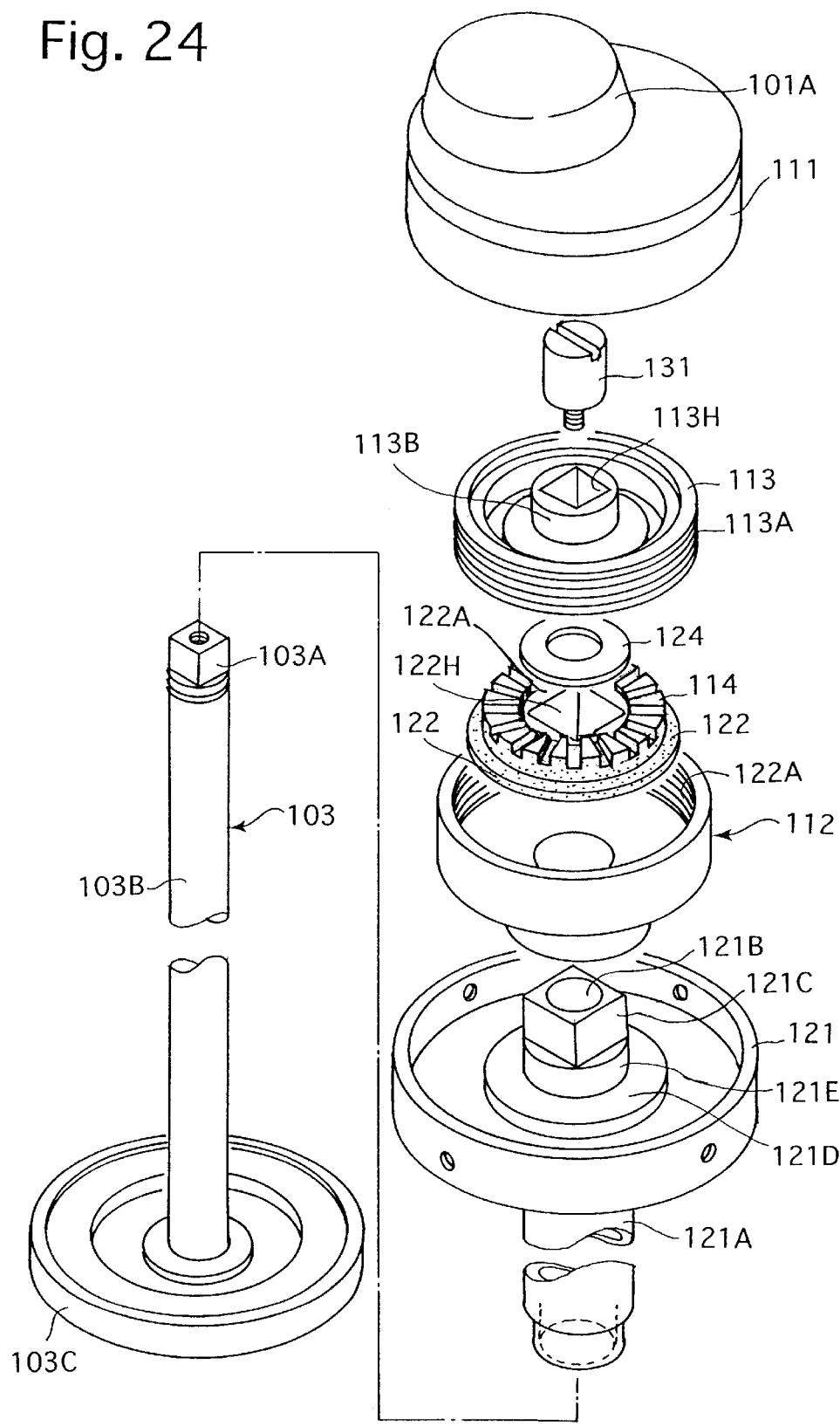
FIG. 24 is an exploded perspective view of fundamental elements of the control device shown in FIG. 21.

The axially-movable lock member 113 is provided on an outer peripheral surface thereof with a male thread 113A (see FIG. 24). The axially-movable lock member 113 is screwed into the upper lock cylinder 112 from the upper side thereof with the male thread 113A being in mesh with the female thread 112A.

The square shaft end 103A, which is formed at the upper end of the rotational shaft 103, is fitted in the square hole 113H of the hollow cylindrical slide portion 113B of the axially-movable lock member 113 to be slidable in the direction of the axis L relative to the axially-movable lock member 113. The outer peripheral surface of the hollow cylindrical slide portion 113B is a cylindrical surface which allows the cylindrical member 111 to rotate freely about the axis L relative to the hollow cylindrical slide portion 113B. With this structure, if the upper lock cylinder 112 is rotated by turning the L-R lock knob 101A via the cylindrical member 111, the axially-movable lock member 113 moves in the direction of the axis L of the rotational shaft 103 without rotating relative to the rotational shaft 103 while the hollow cylindrical slide portion 113B is sliding on the square shaft end 103A, in the direction of the axis L of the rotational shaft 103, due to the engagement of the male thread 113A with the female thread 112A and due to the engagement of the square shaft end 103A in the square hole 113H of the hollow cylindrical slide portion 113B.

The friction pad 114 is made of a material having a high coefficient of friction such as cork or silicon rubber. In this particular embodiment, the friction pad 114 is shaped to have a high elasticity in the direction of the thickness thereof, i.e., in the direction of the axis L of the rotational shaft 103.

The L-R steering portion 102 is provided with an L-R angle knob 102A which is manually controlled to steer the distal end of the insertion portion of the endoscope in left and right directions, similar to the L-R angle knob 23 of the first embodiment. The L-R steering portion 102 is further provided with the aforementioned first rotatable member 121, a disk pad 122, and a first pulley 123 (see FIG. 23).

The L-R angle knob 102A is fixed to the first rotatable member 121 via four set screws 102B (only two of them are shown in FIG. 22). Turning the L-R angle knob 102A clockwise and counterclockwise causes the distal end of the insertion portion of the endoscope to bend right and left, respectively.

Figure 23:
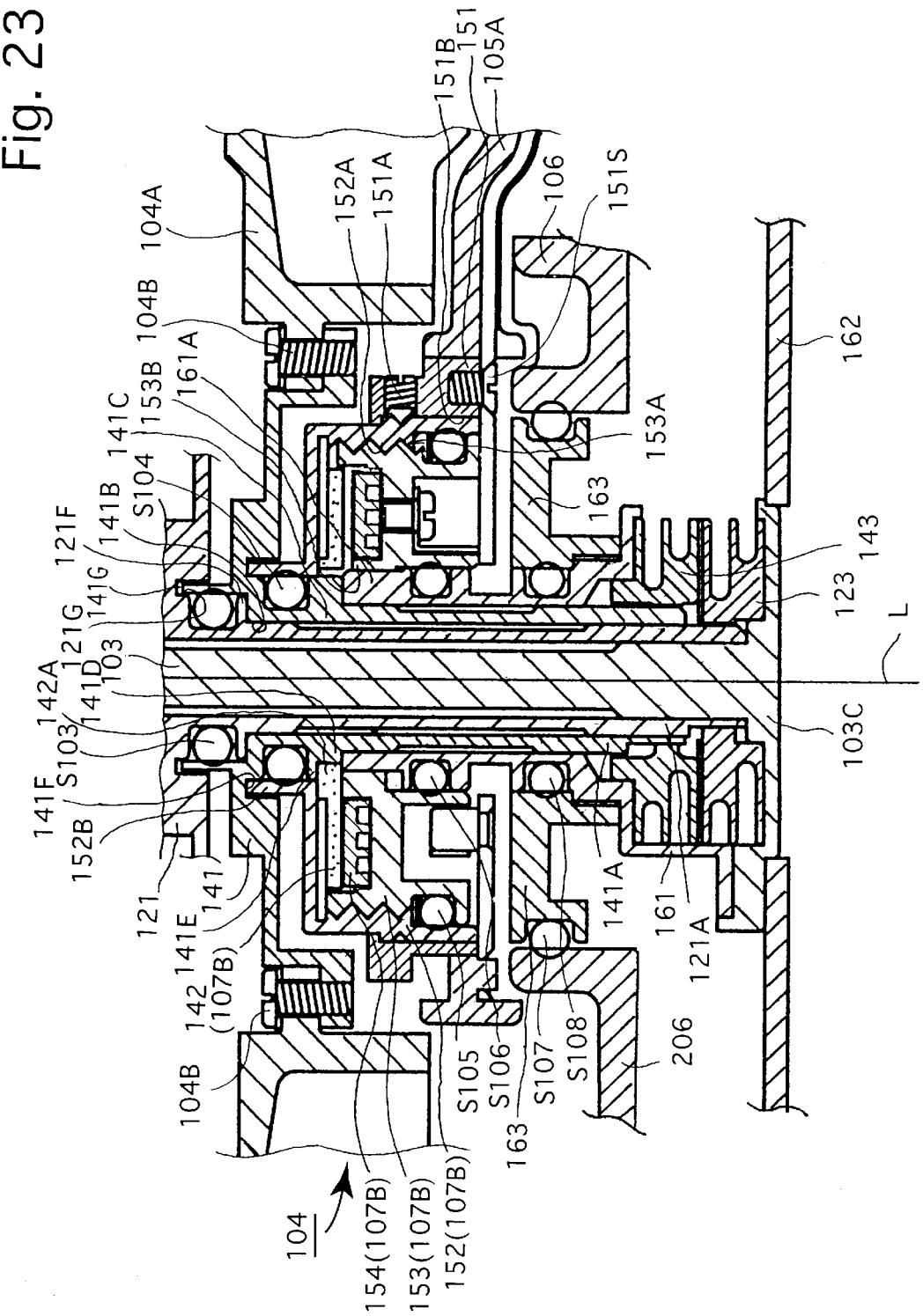
FIG. 23 is a cross sectional view of a lower half of the control device shown in FIG. 21.

The first rotatable member 121 is provided with a cylindrical shaft portion 121A the major part of which extends downwards from the bottom of the first rotatable member 121 with respect to, e.g., FIG. 23. The cylindrical shaft portion 121A is provided along the axis thereof with an axial hole 121B in which the rotational shaft 103 is fitted so that the first rotatable member 121 can rotate about the axis L of the rotational shaft 103 relative to the rotational shaft 103. As shown in FIG. 23, the lower end of the cylindrical shaft portion 121A is in contact with a base 103C of the rotational shaft 103. When the L-R angle knob 102A is turned, the cylindrical shaft portion 121A rotates together with the L-R angle knob 102A while the lower end of the cylindrical shaft portion 121A remains in contact with the base 103C of the rotational shaft 103. The aforementioned first pulley 123 is fixed coaxially to the lower end of the cylindrical shaft portion 121A. A pair of control wires (not shown) which are similar to the first pair of control wires 25 and 26 in the first embodiment are fixed to the first pulley 123.

One of the first pair of control wires (a first control wire) is wound around the first pulley 123 while the other wire (the second control wire) is extended from the first pulley 123 toward the distal end of the flexible insertion portion of the endoscope if the first pulley 123 rotates in one rotational direction (i.e., if the L-R angle knob 102A is turned in one rotational direction), while the second control wire is wound around the first pulley 123 while the first control wire is extended from the first pulley 123 toward the distal end of the flexible insertion portion of the endoscope if the first pulley 123 rotates in the other rotational direction (i.e., if the L-R angle knob 102A is turned in the other rotational direction). The first pair of control wires have respective distal portions thereof anchored to joint rings (not shown) provided in the bendable distal end of the flexible insertion portion of the endoscope. Pulling and extending actions of the first pair of wires cause the bendable distal end to bend left and right.

The disk pad 122 is positioned in the upper lock cylinder 112 immediately below the friction pad 114. The disk pad 122 is provided at the center thereof with an engaging portion 122A having a square hole 122H (see FIG. 24) extending along the axis of the disk pad 122. The upper end of the cylindrical shaft portion 121A extends upwards from the first rotatable member 121 to form the aforementioned cylindrical portion 121E and a square shaft end 121C formed on top of the cylindrical portion 121E as clearly shown in FIG. 24. The square shaft end 121C is fitted in the square hole 122H of the disk pad 122. With this structure, the disk pad 122 rotates together with the first rotatable member 121 when the first rotatable member 121 rotates. The engaging portion 122A of the disk pad 122 is held between a ring member 124 and a round mounting portion 121D (see FIG. 24) of the first rotatable member 121 so that the disk pad 122 rotates without moving along the rotational shaft 103 thereon when the first rotatable member 121 is rotated by turning the L-R angle knob 102A.

The rotational shaft 103 is provided with the square shaft end 103A, a cylindrical shaft portion 103B and the aforementioned base 103C in that order from the upper end to the lower end of the rotational shaft 103. The set screw 131 is screwed into the square shaft end 103A from the top thereof, and the first pulley 123 is fixed coaxially to the base 103C. The rotational shaft 103 is fixed to a substrate 162 (see FIGS. 21 and 23) which is fixed to and positioned in the housing 106.

The U-D steering portion 104 is provided with a U-D angle knob 104A which is manually controlled to steer the distal end of the insertion portion of the endoscope in upward and downward directions, similar to the U-D angle knob 33 of the first embodiment. The U-D steering portion 104 is further provided with a second rotatable member 141, a disk pad 142 and a second pulley 143 (see FIG. 23).

The U-D angle knob 104A is fixed to the second rotatable member 141 via four set screws 104B (only two of them are shown in FIG. 23). Turning the U-D angle knob 104A clockwise and counterclockwise causes the distal end of the insertion portion of the endoscope to bend downward and upward, respectively.

The second rotatable member 141 is provided with a cylindrical shaft portion 141A which extends in the vertical direction as viewed in FIG. 23. The cylindrical shaft portion 141A is provided along an axis thereof with an axial hole 141B in which the cylindrical shaft portion 121A of the first rotatable member 121 is fitted so that the second rotatable member 141 can rotate about the axis L of the rotational shaft 103 relative to the rotational shaft 103.

The second rotatable member 141 is provided on top thereof with an annular projection 141G which is fitted in an annular groove 121G formed at the bottom of the first rotatable member 121. An O-ring S103 is positioned between the first rotatable member 121 and the second rotatable member 141 to seal the gap therebetween in a watertight fashion.

The cylindrical shaft portion 141A is provided between the upper and lower ends thereof with a radial projecting portion 141C. The radial projecting portion 141C is held between the lower face of a stop flange 121F formed integral with the cylindrical shaft portion 121A and the upper face of a guide support 161A formed integral with a stationary hollow cylindrical base 161 in a manner so that the cylindrical shaft portion 141A can rotate about the rotational shaft 103. The cylindrical shaft portion 141A is provided thereon around an outer peripheral surface thereof with a square shaft portion 141D. The aforementioned second pulley 143 is fixed coaxially to the lower end of the cylindrical shaft portion 141A. A second pair of control wires (not shown) which are similar to the second pair of control wires 35 and 36 in the first embodiment are fixed to the second pulley 143.

One of the second pair of control wires (the third control wire) is wound around the second pulley 143 while the other wire (the fourth control wire) is extended from the second pulley 143 toward the distal end of the flexible insertion portion of the endoscope if the second pulley 143 rotates in one rotational direction (i.e., if the U-D angle knob 104A is turned in one rotational direction), while the fourth control wire is wound around the second pulley 143 while the third control wire is extended from the second pulley 143 toward the distal end of the flexible insertion portion of the endoscope if the second pulley 143 rotates in the other rotational direction (i.e., if the U-D angle knob 104A is turned in the other rotational direction).

The second pair of control wires have respective distal portions thereof anchored to joint rings (not shown) provided in the bendable distal end of the flexible insertion portion of the endoscope. Pulling and extending actions of the second pair of wires cause the bendable distal end to bend upward and downward.

The disk pad 142 is positioned in a lower lock cylinder 152 immediately above a friction pad 154 (see FIG. 23). The disk pad 142 is provided at the center thereof with an engaging portion 142A having a square hole 142H extending along the axis of the disk pad 142. The square shaft portion 141D of the cylindrical shaft portion 141A of the second rotatable member 141 is fitted in the square hole 142H of the disk pad 142. With this structure, the disk pad 142 rotates together with the second rotatable member 141 when the second rotatable member 141 rotates.

The engaging portion 142A of the disk pad 142 is held between a round mounting portion 141E (see FIG. 23) and the guide support 161A of the stationary hollow cylindrical base 161 so that the disk pad 142 rotates together with the U-D angle knob 104A without moving along the cylindrical shaft portion 141A thereon when the second rotatable member 141 is rotated by turning the U-D angle knob 104A.

The U-D lock operating portion 105 is manually operated to lock the U-D angle knob 104A of the U-D steering portion 104. A U-D lock lever 105A which can rotate about the rotational shaft 103, a cylindrical member 151 to which the U-D lock lever 105A is fixed, the aforementioned lower lock cylinder 152 which is fixed to the cylindrical member 151 via a set screw 151A, an axially-movable lock member 153, and the aforementioned friction pad 154 which is fixed to the axially-movable lock member 153 are fundamental elements of the U-D lock operating portion 105.

The U-D lock lever 105A is fixed to the cylindrical member 151 with set screws 151S (only one of them is shown in FIG. 23). The cylindrical member 151 is secured to the lower lock cylinder 152 via the set screw 151A after the position of the cylindrical member 151 relative to the lower lock cylinder 152 in the vertical direction as viewed in FIG. 23 (i.e., in the direction of the axis of the rotational shaft 103) is finely adjusted. With this structure, the U-D lock lever 105A and the lower lock cylinder 152 rotate together in the same rotational direction by the same angle of rotation when the U-D lock lever 105A is turned.

The lower lock cylinder 152 is formed as a hollow cylindrical member, the lower end of which is open. The lower lock cylinder 152 is provided on top thereof with an annular projection 152B which is fitted in an annular groove 141F formed on a bottom face of the second rotatable member 141. An O-ring S104 is positioned between the second rotatable member 141 and the lower lock cylinder 152 to seal the gap therebetween in a watertight fashion.

Figure 25:
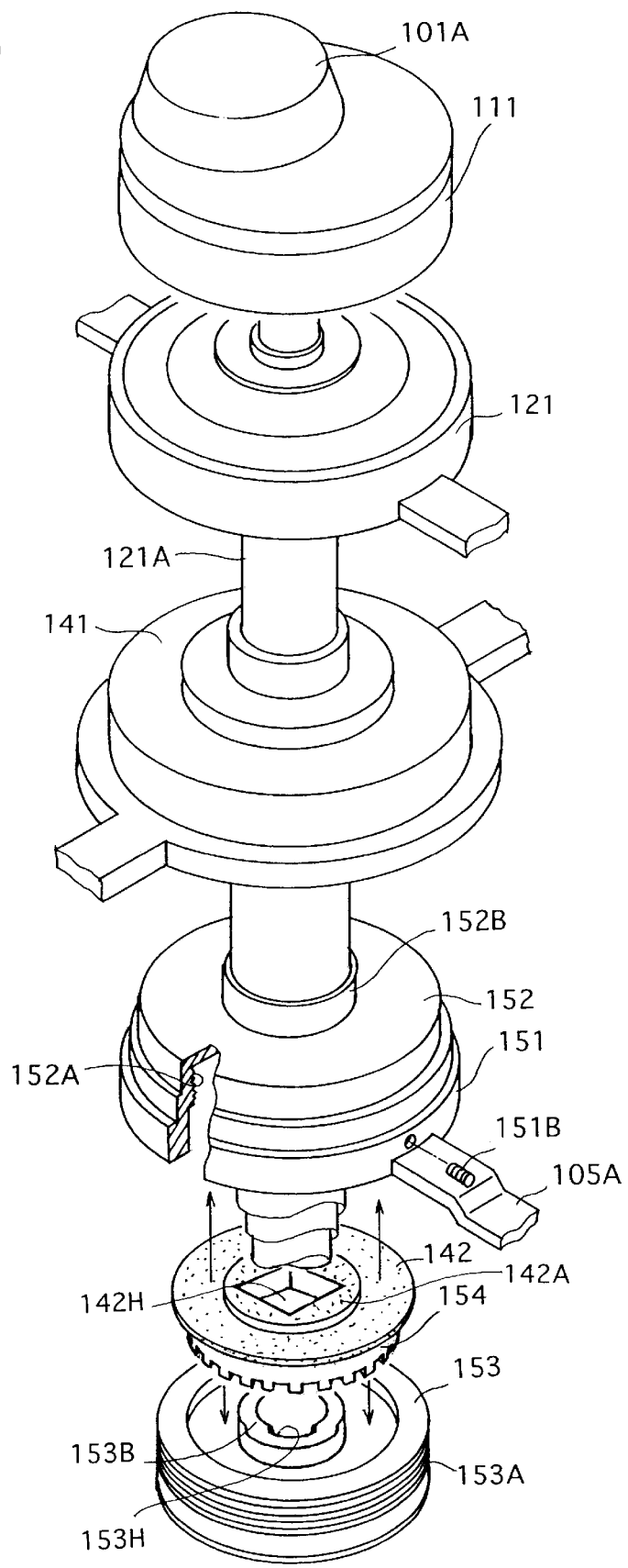
FIG. 25 is a perspective view, partly exploded, of fundamental elements of the control device shown in FIG. 21.

The axially-movable lock member 153 is substantially in the shape of a cylinder and is provided on an outer peripheral surface thereof with a male thread 153A (see FIG. 25). The axially-movable lock member 153 is screwed into the lower lock cylinder 152 from the lower side thereof with the male thread 153A being in mesh with the female thread 152A. An O-ring S105 is positioned between axially-movable lock member 153 and the lower lock cylinder 152 to seal the gap therebetween in a watertight fashion. The axially-movable lock member 153 is provided at the center thereof with a hollow slide portion 153B having a non-circular hole 153H (see FIG. 25). The guide support 161A, which is formed at the upper end of the stationary hollow cylindrical base 161, has a non-circular cross section corresponding to the cross sectional shape of the non-circular hole 153H. The guide support 161A is fitted in the non-circular hole 153H of the hollow slide portion 153B to be slidable vertically with respect to FIG. 23. An O-ring S106 is positioned between the guide support 161A and the hollow slide portion 153B to seal the gap therebetween in a watertight fashion. With this structure, if the lower lock cylinder 152 is rotated by turning the U-D lock lever 105A via the cylindrical member 151, the axially-movable lock member 153 moves in the direction of the axis L of the rotational shaft 103 without rotating relative to the rotational shaft 103 while the hollow slide portion 153B is sliding on the guide support 161A due to the engagement of the male thread 153A with the female thread 152A and due to the engagement of the guide support 161A in the non-circular hole 153H of the hollow slide portion 153B of the axially-movable lock member 153.

The friction pad 154 is made of a material having a high coefficient of friction such as cork or silicon rubber. In this particular embodiment, the friction pad 154 is shaped to have a high elasticity in the direction of the thickness thereof, i.e., in the direction of the axis L of the rotational shaft 103.

Figure 21:
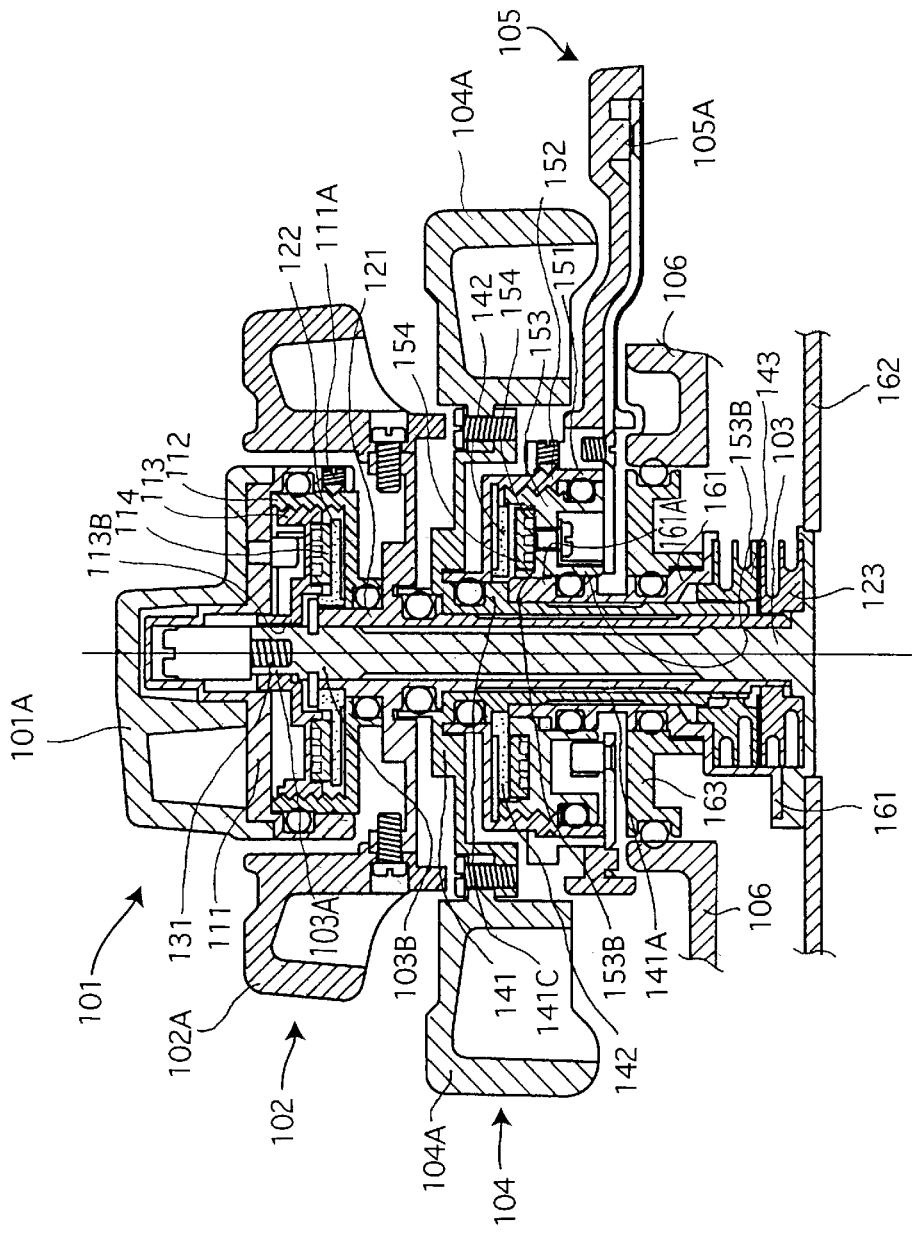
FIG. 21 is a view similar to FIG. 2 and illustrates fundamental elements of the second embodiment of the control device of the endoscope.

As can be seen in FIG. 21, the aforementioned stationary hollow cylindrical base 161, the aforementioned substrate 162 and a cover plate 163 are positioned in the housing 106. The cylindrical base 161 supports each of the cylindrical shaft portion 121A of the first rotatable member 121 and the cylindrical shaft portion 141A of the second rotatable member 141 so that each of the cylindrical shaft portion 121A and the cylindrical shaft portion 141A can rotate freely about the rotational shaft 103. The cover plate 163 closes an annular gap between the housing 106 and the cylindrical base 161 via two O-rings S107 and S108.

As mentioned above, the locking mechanism includes the U-D locking mechanism 107A and the U-D locking mechanism 107B. The L-R locking mechanism 107A functions to lock the L-R angle knob 102A so that the L-R angle knob 102A does not rotate when unnecessary, to thereby lock the distal end of the insertion portion of the endoscope temporarily in a left or right direction. The U-D locking mechanism 107B functions to lock the U-D angle knob 104A so that the U-D angle knob 104A does not rotate when unnecessary, to thereby lock the distal end of the insertion portion of the endoscope temporarily in an upward or downward direction.

The upper lock cylinder 112, the axially-movable lock member 113, the friction pad 114 and the disk pad 122 are fundamental elements of the L-R locking mechanism 107A. The axially-movable lock member 113 moves in the direction of the axis L (i.e., in the vertical direction as viewed in FIG. 21) by rotation of the upper lock cylinder 112. This vertical movement of the axially-movable lock member 113 causes the friction pad 114 to come into pressing contact with the disk pad 122 to thereby prohibit the disk pad 122 from rotating (i.e., prohibit the L-R angle knob 102A from rotating) with friction between the friction pad 114 and the disk pad 122.

The lower lock cylinder 152, the axially-movable lock member 153, the friction pad 154 and the disk pad 142 are fundamental elements of the U-D locking mechanism 107B. The axially-movable lock member 153 moves in the direction of the axis L (i.e., in the vertical direction as viewed in FIG. 21) by rotation of the lower lock cylinder 152. This vertical movement of the axially-movable lock member 153 causes the friction pad 154 to come into pressing contact with the disk pad 142 to thereby prohibit the disk pad 142 from rotating (i.e., prohibit the U-D angle knob 104A from rotating) with friction between the friction pad 154 and the disk pad 142.

Figure 26:
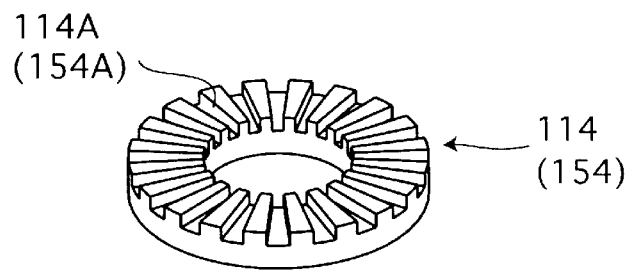
FIG. 26 is a perspective view of a friction pad which is utilized as an element of the locking device for each of the L-R steering device and the U-D steering device.
Figure 33:
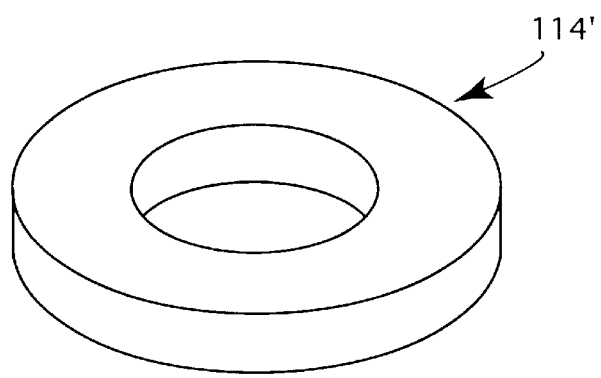
FIG. 33 is a perspective view of a conventional friction pad which is to be compared with the friction pad shown in FIG. 26.

The friction pads 114 and 154 will be hereinafter discussed in detail with reference to FIGS. 26 through 29. Note that the friction pads 114 and 154 are the same. As shown in FIG. 26, the friction pad 114(154) is in the shape of a doughnut. Unlike a conventional friction pad 114' shown in FIG. 33, the surface of the friction pad 114(154) which is fixed to the axially-movable lock member 113(153) has a plurality of radial projections and depressions 114A (154A) formed thereon arranged at equi-angular intervals. This structure gives the friction pad 114(154) high elasticity in the direction of the thickness thereof (i.e. in the direction of the axis L of the rotational shaft 103). In other words, the friction pad 114(154) is structured to be compressed easily in the direction of the thickness thereof (see FIG. 28).

In the illustrated embodiment, although the plurality of radial projections and depressions 114A (154A) are formed on the surface of the friction pad 114 (154) which is fixed to the axially-movable lock member 113(153), the plurality of radial projections and depressions 114A (154A) can be formed on the opposite surface of the friction pad 114(154), i.e., on the surface of the friction pad 114(154) which comes into pressing contact with the disk pad 122(142).

Figure 29A:
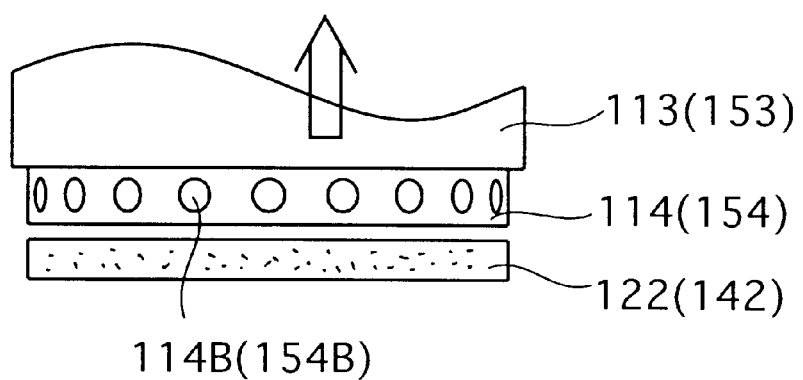
FIG. 29A is an explanatory view of the operation of another embodiment of the friction pad when the associated locking device is in an unlocked state.
Figure 29B:
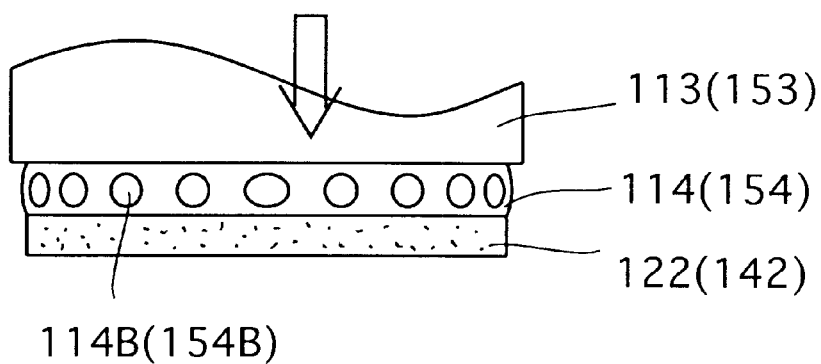
FIG. 29B is an explanatory view of the operation of the friction pad shown in FIG. 29A when the associated locking device is in a locked state.

As shown in FIGS. 29A and 29B, instead of the plurality of radial projections and depressions 114A(154A), a plurality of radial holes 114B (115B) which penetrate the friction pad 114(154) in radial directions at equi-angular intervals can be formed in the friction pad 114(154) so as to be compressed easily in the direction of the thickness of the friction pad 114(154).

The operation of the L-R locking mechanism 107A using the friction pad 114 will be hereinafter discussed. For instance, turning the L-R lock knob 101A in a direction to lock the steerable bendable portion 12a after the steerable bendable portion 12a has been bent to a desired curved shape causes the upper lock cylinder 112, which is fixed to the L-R lock knob 101A, to rotate together with the L-R lock knob 101A in the same rotational direction by the same angle of rotation. This rotation of the upper lock cylinder 112 causes the axially-movable lock member 113 to move inwards (downwards as viewed in FIG. 21) in the direction of the axis L of the rotational shaft 103 due to the engagement of the male thread 113A with the female thread 112A and due to the engagement of the square shaft end 103A in the square hole 113H of the hollow cylindrical slide portion 113B. Therefore, the friction pad 114, which is fixed to the axially-movable lock member 113, also moves downwards together the axially-movable lock member 113 (see FIG. 27B). If the L-R lock knob 101A is turned in the other direction to unlock the steerable bendable portion from the state shown in FIG. 27B, the axially-movable lock member 113 moves upwards along the axis L of the rotational member 103 to thereby disengage the friction pad 114 from the disk pad 122 (see FIG. 27A).

Figures 27A, 27B:
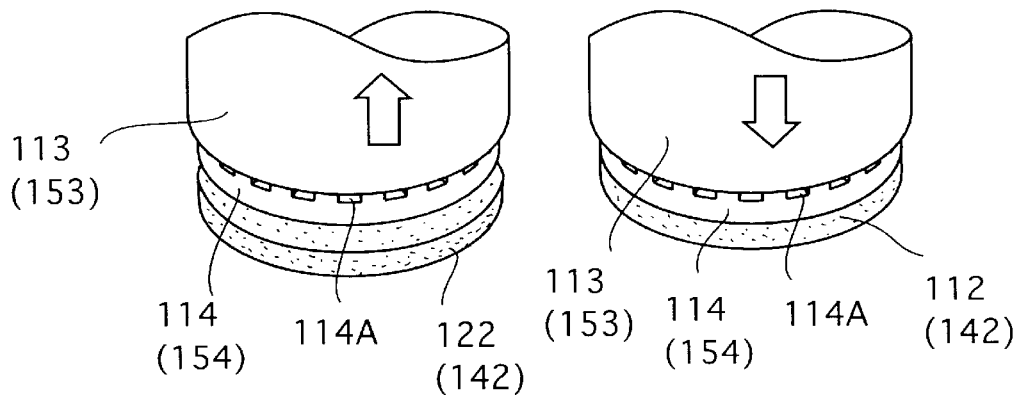
FIG. 27A is an explanatory view of the operation of the friction pad shown in FIG. 26 when the associated locking device is in an unlocked state.
FIG. 27B is an explanatory view of the operation of the friction pad shown in FIG. 26 when the associated locking device is in a locked state.
Figure 28:
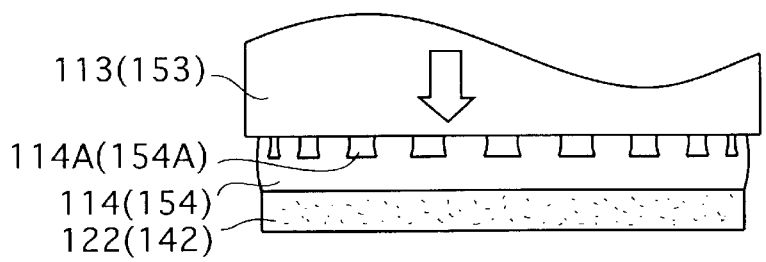
FIG. 28 is a side elevational view of the friction pad shown in FIG. 26 and peripheral elements thereof, showing a state where the friction pad is elastically compressed when the associated locking device is in a locked state.

The downward movement of the friction pad 114 brings the friction pad 114 into pressing contact with the disk pad 122 that is fixed to the first rotatable member 121 (see FIGS. 27B and 28). Further turning the L-R lock knob 101A in a direction to lock the steerable bendable portion causes the friction pad 114 to be further pressed against the disk pad 122, to thereby prohibit the L-R angle knob 102A from rotating via the friction between the friction pad 114 and the disk pad 122.

Accordingly, when the operator is looking at a target portion with the steerable bendable portion of the insertion portion of the endoscope being inserted into a hollow organ or part such as an body cavity or an inner part of a jet engine, the distal end can be securely locked in a desired curved shape in a left or right direction even if the operator's finger or something else accidentally touches the L-R angle knob 102A of the L-R steering portion 102. This makes it possible to prevent the distal end of the insertion portion of the endoscope from moving accidentally by an accidental rotation of the L-R angle knob 102A to thereby prevent the image of a target part from deviating from the field of view of the endoscope during operation of the endoscope.

The operation of the U-D locking mechanism 107B using the friction pad 154 is substantially to the same as the operation of the L-R locking mechanism 107A using the friction pad 114, therefore the description about the operation of the U-D locking mechanism 107B is omitted.

According to the friction pad 114(154) having the above described structure, the friction pad 114(154) can be elastically deformed largely, which makes it possible to increase the maximum amount of movement of the axially-movable lock member 113(153) relative to the disk pad 122(142) in the direction of the axis L. This in turn makes it possible to secure sufficient play between the lock position and the unlocked position of each of the L-R locking mechanism 107A and the U-D locking mechanism 107B.

Consequently, the distal end of the endoscope can be half-locked easily with the locking device in an easy and quick manner. This improves the operability of the control device of the endoscope.

Further, according to the friction pad 114(154) having the above described structure, since it is possible to increase the maximum amount of movement of the axially-movable lock member 113(153) relative to the disk pad 122(142) in the direction of the axis L, a variation of the locking force applied to each of the L-R lock knob 101A and the U-R lock lever 105A per unit of movement can be easily adjusted. As a consequence, the locking force can be easily adjusted, and a fine adjustment of the locking force does not have to be carried out.

As can be understood from the foregoing, according to the second embodiment of the control device of the endoscope, since each friction pad (114 and 154) is shaped to have a high elasticity in the direction of the thickness thereof, the amount of movement of the axially-movable lock member 113(153) between the lock position and the unlock position thereof can be increased, and at the same time, the locking force can be easily adjusted and does not have to be finely adjusted.

Furthermore, according to the second embodiment of the control device of the endoscope, since the amount of movement of the axially-movable lock member 113(153) between the lock position and the unlock position thereof can be increased, a position between the lock position and the unlock position where the distal end of the endoscope can be half-locked can be freely set within a wide range, so that such a position can be easily set.

FIGS. 30, 31 and 32 show the third embodiment of the control device of the endoscope. Although only a lower half portion of the third embodiment of the control device of the endoscope, which includes a U-D steering device 201 for bending the steerable bendable portion of the endoscope upward and downward and a locking device for the U-D steering device 201, is illustrated in FIG. 30, the third embodiment of the control device of the endoscope also includes an L-R steering device for bending the steerable distal end of the endoscope right and left and a locking device for the L-R steering device, which are arranged coaxially to the U-D steering device and the locking device for the U-D steering device, similar to each of the above described first and second embodiments of the control device. Since the basic structures of the L-R steering device and the locking device for the L-R steering device are identical to those of the U-D steering device 201 and the locking device for the U-D steering device 201, only the U-D steering device 201 and the locking device for the U-D steering device 201 will be hereinafter discussed with reference to FIGS. 30, 31 and 32 to discuss features of the third embodiment of the control device of the endoscope.

FIGS. 31 and 32 show fundamental elements of the U-D steering device 201. The U-D steering device 201 is provided, on a substrate 262 fixed to a housing 206, with a rotational shaft 203, a U-D steering portion 204, a U-D lock operating portion 205 for locking the distal end of the endoscope in a left or right direction, and a U-D locking mechanism 207.

The rotational shaft 203 is provided at the lower end thereof with a base 203C. A first pulley 223 which corresponds to the first pulley 123 of the second embodiment is positioned on the base 203C, while a second pulley 243 which corresponds to the second pulley 143 of the second embodiment is positioned on the first pulley 223. The base 203C of the rotational shaft 203 is fixed to the substrate 262 which is fixed to and positioned in the housing 206.

The U-D steering portion 204 is provided with a U-D angle knob (operational member) 204A which is manually controlled to steer the distal end of the insertion portion of the endoscope in upward and downward directions, similar to the U-D angle knob 33 of the first embodiment. The U-D steering portion 204 is further provided with a second rotatable member 241 (which corresponds to the second rotatable member 141 of the second embodiment), a disk pad (friction member) 242 and the aforementioned second pulley The U-D angle knob 204A is fixed to the second rotatable member 241 via set screws (not shown). Tuning the U-D angle knob 204A clockwise and counterclockwise causes the distal end of the insertion portion of the endoscope to bend downward and upward, respectively.

The second rotatable member 241 is provided with a cylindrical shaft portion 241A which extends in the vertical direction as viewed in FIG. 30. The cylindrical shaft portion 241A is provided along an axis thereof with an axial hole 241B in which a cylindrical shaft portion 221A of a first rotatable member 221 (which corresponds to the first rotatable member 121 of the second embodiment)is fitted so that the second rotatable member 241 can rotate about the axis L of the rotational shaft 203 relative to the rotational shaft 203.

The cylindrical shaft portion 241A is provided between the upper and lower ends thereof with a radial projecting portion 241C. The radial projecting portion 241C is held between a stop flange 221D formed integral with the cylindrical shaft portion 221A and the upper face of a guide support 261A formed integral with a stationary hollow cylindrical base 261 (which corresponds to the stationary hollow member 161 of the second embodiment) in a manner so that the cylindrical shaft portion 241A can rotate about the rotational shaft 203. An O-ring S201 having an X-shape cross section is positioned between the radial projecting portion 241C and the cylindrical shaft portion 221A to seal the gap therebetween in a watertight fashion. The aforementioned second pulley 243 is fixed coaxially to the lower end of the cylindrical shaft portion 241A. A pair of control wires (not shown) which are similar to the second pair of control wires 35 and 36 in the first embodiment are fixed to the second pulley 243.

One of the pair of control wires (the first control wire) is wound around the second pulley 243 while the other wire (the second control wire) is extended from the second pulley 243 toward the distal end of the flexible insertion portion of the endoscope if the second pulley 243 rotates in one rotational direction (i.e., if the U-D angle knob 204A is turned in one rotational direction), while the second control wire is wound around the second pulley 243 while the first control wire is extended from the second pulley 243 toward the distal end of the flexible insertion portion of the endoscope if the second pulley 243 rotates in the other rotational direction (i.e., if the U-D angle knob 204A is turned in the other rotational direction).

The disk pad 242 is coaxially fixed to the bottom of the U-D angle knob 204A immediately below a friction pad 254. The disk pad 242 is provided at the center thereof with a circular hole 242A. A cylindrical member 251 with which a U-D lock lever (operation member) 205A is formed integral is fitted in the circular hole 242A. The cylindrical member 251 is provided thereon along an axis thereof with a cylindrical portion 251B (see FIG. 31) in which a circular through hole 251A is formed along the axis of the cylindrical member 251. The cylindrical portion 251B is provided on an outer peripheral surface thereof with an annular groove in which an O-ring S202 having an X-shape cross section is fitted. The O-ring S202 is held between the cylindrical member 251 and the disk pad 242. The disk pad 242 rotates together with the U-D angle knob 204A without moving on the cylindrical shaft portion 241A when the second rotatable member 241 is rotated by turning the U-D angle knob 204A.

The U-D lock operating portion 205 is manually operated to lock the U-D angle knob 204A of the U-D steering portion 204. A U-D lock lever 205A which can rotate about the rotational shaft 203, the aforementioned cylindrical member 251, a pair of cam followers 252, an axially-movable lock member 253 which is engaged with the cam followers 252, and the friction pad 254 which is fixed to the axially-movable lock member 253 are fundamental elements of the U-D lock operating portion 205.

As shown in FIG. 31, the U-D lock lever 205A is formed integral with the cylindrical member 251. The guide support 261A of the stationary hollow cylindrical base 261 is fitted in the circular through hole 251A of the cylindrical portion 251B of the cylindrical member 251 with an O-ring S203 being positioned between the guide support 261A and the cylindrical portion 251B so that the cylindrical member 251 can rotate about the guide support 261A. When the U-D lock lever 205A is turned, the cylindrical member 251 rotates together with the U-D lock lever 205A in the same rotational direction by the same angle of rotation without moving in the direction of the axis of the rotational shaft 203 (i.e., in the vertical direction as viewed in FIG. 30). The aforementioned pair of cam followers 252 are fixed to the cylindrical portion 251B of the cylindrical member 251 on opposite sides of the cylindrical portion 251B (i.e., at intervals of 180 degrees about the axis of the cylindrical portion 251B) to extend radially outwards.

As shown in FIG. 31, each cam follower 252 is provided with a large diameter portion 252A and a small diameter portion 252B and is fixed to the cylindrical portion 251B. The diameter D1 of the large diameter portion 252A is greater than the diameter D2 of the small diameter portion 252B. The large diameter portion 252A of each cam follower 252 is engaged in a corresponding cam groove 255 of the axially-movable lock member 253.

The axially-movable lock member 253 is formed as a substantially thin disk, and is made of, for example metal (copper beryllium alloy or phosphor bronze and nickel). The axially-movable lock member 253 is provided with a pair of cam grooves 255 which are symmetrically formed with respect to the axis of the axially-movable lock member 253. The large diameter portions 252A of the pair of cam followers 252 are engaged in the pair of cam grooves 255, respectively.

The axially-movable lock member 253 is further provided, on top thereof along the axis of the axially-movable lock member 253, with a hollow cylindrical slide portion 253A having a square hole 253H which is slidably fitted on a square shaft end 261B formed at the upper end of the guide support 261A of the stationary hollow cylindrical base 261. The axially-movable lock member 253 is provided, around the hollow cylindrical slide portion 253A, with two high sector portions 253B and two low sector portions 253C which are alternately arranged at intervals of 90 degrees around the hollow cylindrical slide portion 253A. The pair of cam grooves 255 are formed below the two low sector portions 253C, respectively. As shown in FIG. 32, a slit 255D is formed on the axially-movable lock member 253 at one of the two circumferential ends (the left end as viewed in FIG. 32) of each lower sector portion 253C. Therefore, two slits 255D are symmetrically formed in total with respect to the hollow cylindrical slide portion 253A. Each slit 255D penetrates into the corresponding cam groove 255 from the top face of the corresponding low sector portion 253C. Furthermore, a circular arc slit 255F (only one is partly shown in FIG. 31) is formed along the border between each low sector portion 253B and the hollow cylindrical slide portion 253A. Therefore, two circular arc slits 255F are formed in total symmetrically with respect to the hollow cylindrical slide portion 253A. Each circular arc slit 255F penetrates into the corresponding cam groove 255 from top face of the corresponding low sector portion 253C. Accordingly, each of the two low sector portions 253C functions as an arc-shaped leaf spring which can elastically bend vertically as viewed in FIG. 31.

Each cam groove 255 is upwardly inclined gradually in a counterclockwise direction as viewed in FIG. 31 (i.e., in the direction from left to right as viewed in FIG. 32).

With the above described structures, the cylindrical member 251 and the pair of cam followers 252 rotate together in the same rotational direction by the same angle of rotation when the U-D lock lever 205A is turned. This rotation of the cylindrical member 251 and the pair of cam followers 252 causes the axially-movable lock member 253 to move vertically in the direction of the axis of the rotational shaft 203 due to the engagement of the pair of cam followers 252 with the pair of cam grooves 255 and due to the engagement of the square shaft end 261B in the square hole 253H of the hollow cylindrical slide portion 253A. Therefore, the friction pad 254, which is fixed to the axially-movable lock member 253, also moves vertically together the axially-movable lock member 253.

The friction pad 254 is made of a material having a high coefficient of friction such as cork or silicon rubber. The friction pad 254 is shaped like a doughnut in this particular embodiment, and it is preferable that the friction pad 254 have a high elasticity in the direction of the thickness thereof, i.e., in the direction of the axis of the rotational shaft 203.

As has been described above, the two cam grooves 255 are formed circumferentially on the axially-movable lock member 253 at equi-angular intervals. As shown in FIG. 32, each cam groove 255 is provided with an inclined groove portion 255A which extends in a slanting direction in a predetermined circumferential range having a circumferential length K. The inclined groove portion (255A) is inclined with respect to a plane T (FIG. 32) which is perpendicular to the axis of the rotational shaft 203. Each cam groove 255 is further provided with a lower engaging hole 255B and an upper engaging hole 255C which are formed on the left end and the right end of each cam groove 255 as viewed in FIG. 32, respectively. Each of the lower engaging hole 255B and the upper engaging hole 255C has a substantially circular cross section. The diameter of each of the lower and upper engaging holes 255B and 255C is slightly greater than the diameter of the large diameter portion 252A of each cam follower 252, while the width of each inclined groove portion 255A is substantially equal to or slightly greater than the diameter of the large diameter portion 252A of each cam follower 252. Each cam groove 255 is further provided, on the opposite side of the upper engaging hole 255C with respect to the inclined groove portion 255A, with a slit 255E so that each low sector portion 253C can bend elastically with more ease. The aforementioned slit 255D extends upwards from each of the two lower engaging holes 255B. The maximum angle of rotation of the U-D lock lever 205A depends on the circumferential length K of each cam groove 255, so that the maximum angle of rotation of the U-D lock lever 205A can be changed by changing the circumferential length K. If it is desired to increase the maximum angle of rotation of the U-D lock lever 205A, the circumferential length K only has to be increased.

As can be seen in FIG. 30, the stationary hollow cylindrical base 261, the substrate 262 and a cover plate 263 are positioned in the housing 206. The cylindrical base 261 supports each of the cylindrical shaft portion 221A of the first rotatable member 221 and the cylindrical shaft portion 241A of the second rotatable member 241 so that each of them can rotate freely about the rotational shaft 203. The cover plate 263 closes an annular gap between the housing 206 and the cylindrical base 261 via two O-rings S204 and S205.

The U-D locking mechanism 207 functions to lock the U-D angle knob 204A so that the angle knob 204A does not rotate when unnecessary, to thereby lock the distal end of the insertion portion of the endoscope temporarily in an upward or downward direction.

The pair of cam followers 252, the axially-movable lock member 253, the friction pad 254 and the disk pad 242 are fundamental elements of the U-D locking mechanism 207. The axially-movable lock member 253 moves in the direction of the axis of the rotational shaft 203 (i.e., in the vertical direction as viewed in FIG. 30) by rotation of the cylindrical member 251 and the pair of cam followers 252 via the pair of cam grooves 255. This vertical movement (specifically, the downward movement as viewed in FIG. 30) of the axially-movable lock member 253 causes the friction pad 254 to come into pressing contact with the disk pad 242 to thereby prohibit the disk pad 242 from rotating (i.e., prohibit the U-D angle knob 204A from rotating) with friction between the friction pad 254 and the disk pad 242.

The operation of the pair of cam followers 252, which are fixed to the cylindrical member 251, and the operation of the pair of cam grooves 255, which are formed on the axially-movable lock member 253, will be hereinafter discussed. For instance, turning the U-D lock lever 205A in a direction to lock the steerable bendable portion, after the steerable bendable portion has been bent to a desired curved shape, causes the cylindrical member 251 to rotate together with the U-D lock lever 205A in the same rotational direction by the same angle of rotation. This rotation of the cylindrical member 251 causes the pair of cam followers 252 to move upward as viewed in FIG. 30 along the pair of cam grooves 255, respectively, since the axially-movable lock member 253 is prohibited from rotating about the rotational shaft 203 due to the engagement of the square shaft end 261B in the square hole 253H of the hollow cylindrical slide portion 253A. Therefore, the friction pad 254, which is fixed to the axially-movable lock member 253, also moves downwards together the axially-movable lock member 253.

The downward movement of the friction pad 254 brings the friction pad 254 into pressing contact with the disk pad 242 that is fixed to the second rotatable member 241. Further turning the U-D lock lever 205A in a direction to lock the steerable bendable portion eventually causes the large diameter portion 252A of each cam follower 252 to be engaged with the corresponding upper engaging hole 255C with a click. This causes the friction pad 254 to be further pressed against the disk pad 242, to thereby prohibit the U-D angle knob 205A from rotating via the friction between the friction pad 254 and the disk pad 242.

Accordingly, when the operator is looking at a target portion with the steerable bendable portion of the insertion portion of the endoscope being inserted into a hollow organ or part such as an body cavity or an inner part of a jet engine, the distal end can be securely held in a desired curved shape in an upward or downward direction even if the operator's finger etc. accidentally touches the U-D angle knob 204A of the U-D steering portion 204. This makes it possible to prevent the distal end of the insertion portion of the endoscope from moving accidentally by an accidental rotation of the U-D angle knob 204A to thereby prevent the image of a target part from deviating from the field of view of the endoscope during operation of the endoscope.

Although it is possible to apply the present embodiment to both a U-D lock mechanism and an L-R lock mechanism, only a U-D lock mechanism is disclosed since a lock lever such as the U-D lock lever 205a is more prone to being accidentally moved than a knob of an L-R lock mechanism.

With the axially-movable lock member 253 having a structure unique to the illustrated third embodiment, since each of the two low sector portions 253C functions as an arc-shaped leaf spring which can elastically bend vertically as viewed in FIG. 31 and since the width of each inclined groove portion 255A is substantially equal to or slightly greater than the diameter of the large diameter portion 252A of each cam follower 252, the U-D lock lever 205A can be manually turned with a moderate resistance, giving a distinct feel of operation.

Since the maximum angle of rotation of the U-D lock lever 205A can be changed by changing the circumferential length K, it is possible to increase the maximum amount of movement of the axially-movable lock member 253 relative to the disk pad 254 in the direction of the axis of the rotational shaft 203. This in turn makes it possible to secure sufficient play between the lock position and the unlocked position of the U-D locking mechanism 207. Consequently, the distal end of the endoscope can be half-locked easily with the locking device in an easy and quick manner. This improves the operability of the control device of the endoscope.

Further, according to the third embodiment of the control device of the endoscope, since it is possible to increase the maximum amount of movement of the axially-movable lock member 253 relative to the disk pad 254 in the direction of the axis of the rotational shaft 203, a variation of the locking force applied to the U-D lock lever 205A per unit of movement can be easily adjusted. As a consequence, the locking force can be easily adjusted, while a fine adjustment of the locking force does not have to be carried out.

As can be understood from the foregoing, according to the third embodiment of the control device of the endoscope, since the maximum amount of movement of the axially-movable lock member 253 relative to the disk pad 254 can be increased in the direction of the axis of the rotational shaft 203 by increasing the length of each cam groove 255, the locking force can be easily adjusted while a fine adjustment of the locking force does not have to be carried out.

Furthermore, according to the third embodiment of the control device of the endoscope, since the amount of movement of the axially-movable lock member 253 between the lock position and the unlock position thereof can be increased, a position between the lock position and the unlock position where the distal end of the endoscope can be half-locked can be freely set within a wide range, so that such a position can be easily set.

Furthermore, according to the third embodiment of the control device of the endoscope, since with a simple arrangement wherein each cam groove 255 is provided so that the operator can feel a click at each of the opposite ends thereof with the engaging hole 255A or 255B having a diameter greater than the width of the cam groove 255, a complicated mechanism for making the U-D lock lever 205A stop with a click at each of the lock and unlock positions thereof does not have to be provided. This requires a minimum number of elements for such an arrangement and at the same time reduces the cost of production and also the weight of the endoscope.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope having an elongated insertion portion provided at a distal end thereof with a steerable bendable portion, said endoscope comprising:
   at least one steering member which is rotated to bend said steerable bendable portion;
   at least one locking member which is rotated to lock said steering member, said steering member and said locking member being rotated about a common axis; and
   at least one axially-movable lock member which moves relative to said steering member along said common axis without rotating about said common axis to lock and unlock said steering member when said locking member is turned in a first rotational direction and a second rotational direction, respectively.

2. The endoscope according to claim 1, further comprising a rotational shaft which supports said locking member in a rotatable manner about an axis of said rotational shaft; and
   a non-cylindrical portion having a non-circular cross section which formed on said rotational shaft,
   wherein said axially-movable lock member is positioned around said non-cylindrical portion in a manner so that said axially-movable lock member can move along said axis of said rotational shaft relative to said non-cylindrical portion without rotating about said axis of said rotational shaft.

3. The endoscope according to claim 2, further comprising a drive force transmitting mechanism via which said axially-movable lock member moves along said axis of said rotational shaft in accordance with rotational of said locking member.

4. The endoscope according to claim 2, further comprising:
   a removable retaining member which is fitted on said non-cylindrical portion in a direction perpendicular to said axis of said rotational shaft,
   wherein said removable retaining member is prohibited from moving along and rotating about said axis of said rotational shaft relative to said non-cylindrical portion in a state where said removable retaining member is fitted on said non-cylindrical portion, and
   wherein said removable retaining member is engaged with said axially-movable lock member to prohibit said axially-movable lock member from rotating about said axis of said rotational shaft relative to said non-cylindrical portion.

5. The endoscope according to claim 4, further comprising a guide portion, formed on said axially-movable lock member, for preventing said removable retaining member from coming out of said non-cylindrical portion in a state where said guide portion is fitted on said removable retaining member, wherein said guide portion is fitted on said removable retaining member so that said guide portion is movable in a direction of said axis of said rotational shaft without rotating about said axis of said rotational shaft relative to said removable retaining member.

6. The endoscope according to claim 2, wherein said steering member comprises a steering knob which is mounted around said rotational shaft, and
   wherein said non-cylindrical portion is formed on said rotational shaft in an inner space of said steering knob.

7. The endoscope according to claim 1, wherein said steering member comprises:
   a first steering member which is rotated to bend said steerable bendable portion in a first bending direction; and
   a second steering member which is rotated to bend said steerable bendable portion in a second bending direction, said first steering member and said second steering member being rotated about said common axis;
   wherein said locking member comprises:
   a first locking member which is rotated to lock said first steering member; and
   a second locking member which is rotated to lock said second steering member, said first locking member and said second locking member being rotated about said common axis; and
   wherein said axially-movable lock member comprises:
   a first axially-movable lock member which moves relative to said first steering member along said common axis without rotating about said common axis to lock and unlock said first steering member when said first locking member is turned in said first rotational direction and said second rotational direction, respectively; and
   a second axially-movable lock member which moves relative to said second steering member along said common axis without rotating about said common axis to lock and unlock said second steering member when said second locking member is turned in said first rotational direction and said second rotational direction, respectively.

8. The endoscope according to claim 7, further comprising:
   an inner body shaft which is fixed to a body of the endoscope; and
   an outer cylindrical body which is coaxially provided around said inner body shaft;
   wherein said first axially-movable lock member is mounted to said to inner body shaft to be movable along an axis of said inner body shaft without rotating about said inner body shaft, and
   wherein said second axially-movable lock member is mounted to said outer cylindrical body to be movable along an axis of said outer cylindrical body without rotating about said outer cylindrical body.

9. The endoscope according to claim 8,
   wherein said first steering member comprises a first cylindrical shaft,
   wherein said second steering member comprises a second cylindrical member which is coaxially fitted on said first cylindrical shaft, and
   wherein said first cylindrical shaft and said second cylindrical member are fitted in a cylindrical space which is provided between said inner body shaft and said outer cylindrical body in a radial direction thereof, said first cylindrical shaft and said second cylindrical member being rotatable relative to each other about said axis of said inner body shaft.

10. The endoscope according to claim 8, wherein said first locking member is mounted to said inner body shaft to be rotatable about said axis of said inner body shaft, and
   wherein said second locking member is mounted to said outer cylindrical body to be rotatable about said axis of said outer cylindrical body.

11. The endoscope according to claim 3, wherein said drive force transmitting mechanism comprises male and female threads which mesh with each other, said male and female threads being formed on said locking member and said axially-movable lock member, respectively.

12. The endoscope according to claim 1, further comprising at least one axially-immovable lock member which is fixed to said steering member, wherein said axially-movable lock member moves toward said axially-immovable lock member to lock said steering member when said locking member is turned in said first rotational direction.

13. The endoscope according to claim 12, further comprising:

a first friction pad fixed to said axially-movable lock member; and a second friction pad fixed to said axially-immovable lock member, wherein said axially-movable lock member moves toward said axially-immovable lock member to bring said first friction pad into pressing contact with said second friction pad to thereby lock said steering member when said locking member is turned in said first rotational direction.

14. The endoscope according to claim 13, further comprising an adjusting device for adjusting a position of said axially-immovable lock member relative to said steering member in a direction of said common axis.

15. An endoscope having an elongated insertion portion provided at a distal end thereof with a steerable bendable portion, said endoscope comprising:

at least one control knob which is manually turned about an axis to bend said steerable bendable portion so as to direct the tip of said steerable bendable portion toward a target part;

at least one lock knob which is manually turned about said axis to lock said control knob; and at least one axially-movable lock member which moves relative to said control knob along said axis without rotating about said axis to lock and unlock said control knob when said lock knob is turned in a first rotational direction and a second rotational direction, respectively.

16. An endoscope having an elongated insertion portion provided at a distal end thereof with a steerable bendable portion, said endoscope comprising:

a first steering portion which is rotated to bend said bendable portion in a first bending direction;

a second steering portion which is rotated to bend said bendable portion in a second bending direction, said first steering portion and said second steering portion being rotated about a common axis;

a first axially-movable lock member which moves along said common axis to bias said first steering portion in a first direction away from said second steering portion to lock said first steering portion; and a second axially-movable lock member which moves along said common axis to bias said second steering portion in a second direction away from said first steering portion to lock said second steering portion.

17. The endoscope according to claim 16, wherein said first axially-movable lock member and said second axially-movable lock member move away from each other to bias said first steering portion and said second steering portion, respectively, to lock said first steering portion and said second steering portion, respectively.

18. The endoscope according to claim 16, further comprising:

a first locking portion which is rotated about said common axis to move said first axially-movable lock member along said common axis toward and away from said first steering portion when said first locking portion is turned in forward and reverse rotational directions thereof; and a second locking portion which is rotated about said common axis to move said second axially-movable lock member along said common axis toward and away from said second steering portion when said second locking portion is turned in forward and reverse rotational directions thereof.

19. The endoscope according to claim 18, wherein said first locking portion is engaged with said first axially-movable lock member via first screw threads so that said first axially-movable lock member moves along said common axis, due to an engagement of said first screw threads, when said first locking portion is turned, and wherein said second locking portion is engaged with said second axially-movable lock member via second screw threads so that said second axially-movable lock member moves along said common axis, due to an engagement of said second screw threads, when said second locking portion is turned.

20. The endoscope according to claim 16, wherein each of said first axially-movable lock member and said second axially-movable lock member moves along said common axis without rotating about said common axis.

21. An endoscope having an elongated insertion portion provided at a distal end thereof with a steerable bendable portion, said endoscope comprising:

a first steering portion which can be rotated independently to bend said steerable bendable portion in a first bending direction; and a second steering portion which can be rotated independently to bend said steerable bendable portion in a second bending direction, said first steering portion and second steering portion being rotated about a common shaft;

at least one axially-movable lock member which moves along an axis of said common shaft toward and away from one of said first steering portion and said second steering portion to one of lock and unlock said one of said first steering portion and said second steering portion, wherein said at least one axially-movable lock member moves along said axis to bias said one of said first steering portion and said second steering portion in a direction away from said other of said first steering portion and said second steering portion when locking said one of said first steering portion and said second steering portion.

22. The endoscope according to claim 21, wherein said axially-movable lock member comprises:

a first axially-movable lock member which moves along said axis to bias said first steering portion in a first direction away from said second steering portion to lock said first steering portion; and a second axially-movable lock member which moves along said axis to bias said second steering portion in a second direction away from said first steering portion to lock said second steering portion.

23. An endoscope having an elongated insertion portion provided at a distal end thereof with a steerable bendable portion, said endoscope comprising:

a steering member which is rotated about a shaft to bend said bendable portion;

a locking member which is rotated about said shaft to lock said steering member; and a retaining member which is fixed to an end of said shaft to prevent said locking member from coming out of said shaft from said end thereof; and a spring which rotates together with said locking member when said locking member is turned, wherein said locking member comprises an engaging portion, wherein said retaining member comprises at least one stop portion and at least one stop recess, and wherein said spring is engaged with said stop recess with a click when said engaging portion abuts against said stop portion.

24. The endoscope according to claim 23, wherein said stop portion and said stop recess are positioned substantially on opposite sides of said shaft in a radial direction thereof.

25. The endoscope according to claim 23, wherein said stop portion and said stop recess comprise two stop portions and two stop recesses, respectively.

26. The endoscope according to claim 25, wherein said two stop portions and said two stop recesses are formed on said retaining member at different circumferential positions thereof, wherein one of said two stop portions and one of said two stop recesses are positioned substantially on opposite sides of said shaft in a first radial direction thereof, and wherein the other of said two stop portions and the other of said two stop recesses are positioned substantially on opposite sides of said shaft in a second radial direction thereof.

27. The endoscope according to claim 23, wherein said spring elastically presses said retaining member in a direction toward an axis of said shaft.

28. The endoscope according to claim 23, wherein a non-circular hole is formed on said retaining member, and wherein said end of said shaft is formed to have a cross sectional shape corresponding to the shape of said non-circular hole so that said retaining member can be fitted on said end of said shaft.

29. The endoscope according to claim 23, wherein said retaining member is fixed to said end of said shaft via a set screw which is screwed into said end of said shaft to prevent said retaining member from coming out of said end of said shaft.

30. An endoscope having an elongated insertion portion provided at a distal end thereof with a steerable bendable portion, said endoscope comprising:

a steering member which is rotated about a shaft to bend said bendable portion;

a locking member which is rotated about said shaft to lock said steering member;

a retaining member fixed to an end of said shaft to prevent said locking member from coming out of said shaft from said end thereof;

a projection which projects from said locking member;

a spring which is fixed to said locking member so that part of said spring elastically presses said retaining member in a direction toward said projection, wherein said part of said spring and said projection are positioned substantially on opposite sides of said shaft in a radial direction thereof, wherein said retaining member comprises at least one stop face and at least one stop recess, and wherein said part of said spring is engaged with said stop recess with a click when said projection abuts against said stop face.

31. The endoscope according to claim 30, wherein said stop face and said stop recess comprise two stop faces and two stop recesses, respectively.

32. The endoscope according to claim 31, wherein said two stop faces and said two stop recesses are formed on said retaining member at different circumferential positions thereof, wherein one of said two stop faces and one of said two stop recesses are positioned substantially on opposite sides of said shaft in a first radial direction thereof, and wherein the other of said two stop faces and the other of said two stop recesses are positioned substantially on opposite sides of said shaft in a second radial direction thereof.

33. A manually rotating device comprising:

a shaft;

a manual operation member which is mounted to said shaft to be turned manually about said shaft;

a retaining member fixed to an end of said shaft to prevent said manual operation member from coming out of said shaft from said end thereof; and a spring which is associated with said retaining member, wherein said spring rotates together with said manual operation member when said manual operation member is turned, wherein said manual operation member comprises an engaging portion, wherein said retaining member comprises at least one stop portion and at least one stop recess, and wherein said spring is engaged with said stop recess with a click when said engaging portion abuts against said stop portion.

34. The manually rotating device according to claim 33, wherein said stop portion and said stop recess are positioned substantially on opposite sides of said shaft in a radial direction thereof.

35. An endoscope having an elongated insertion portion provided at a distal end thereof with a steerable bendable portion, said endoscope comprising:

a hollow steering knob which is manually turned about a shaft to bend said steerable bendable portion, an opening being formed on said steering knob;

a first friction brake member which rotates together with said steering knob when said steering knob is turned;

a lock operation member which can be manually turned relative to said steering knob;

a second friction brake member which is driven to move toward and away from said first friction brake member to lock and unlock said steering knob in accordance with rotation of said lock operation member relative to said steering knob; and a locking force adjusting device for adjusting an initial space between said first friction brake member and said second friction brake member, said locking force adjusting device being accessible from the outside of said endoscope via said opening of said steering knob.

36. The endoscope according to claim 35, wherein said locking force adjusting device moves said first friction brake member relative to said steering knob to adjust said initial space in a direction of an axis of said shaft when said locking force adjusting device is operated via said opening.

37. The endoscope according to claim 36, wherein said locking force adjusting device comprises:
   first and second thread portions which mesh with each other, said first thread portion being positioned in said steering knob, said second thread portion being formed on said first friction brake member; and
   at least one engaging portion formed on said first friction brake member to be exposed to said opening,
   wherein said first friction brake member moves in said direction of said axis of said shaft relative to said steering knob in accordance with said first and second thread portions when said first friction brake member is rotated relative to said steering knob with said at least one engaging portion.

38. The endoscope according to claim 37, wherein said steering knob is formed as a substantially hollow cylindrical shape, and is provided with an end face extending substantially perpendicular to said axis of said shaft,
   wherein said opening is formed at said end face of said steering knob, and
   wherein said second friction brake member and said first friction brake member are positioned in said steering knob in said opening thereof so that an outer surface of each of said second friction brake member and said first friction brake member is substantially flush with said end face of said steering knob.

39. The endoscope according to claim 36, wherein said first friction brake member is mounted to said steering knob to be movable in said direction of said axis of said shaft and to be rotatable about said axis of said shaft together with said steering knob,
   wherein said locking force adjusting device comprises:
      a first thread positioned in said steering knob;
      an adjusting ring having a second thread which meshes with said first thread; and
      at least one engaging portion formed on said adjusting ring to be exposed to said opening,
      wherein said first friction brake member moves in said direction of said axis of said shaft relative to said steering knob if said adjusting ring is rotated relative to said steering knob with said engaging portion.

40. The endoscope according to claim 39, wherein said steering knob is formed as a substantially hollow cylindrical shape, and is provided with an end face extending substantially perpendicular to said axis of said shaft,
   wherein said opening is formed on said end face of said steering knob, and
   wherein said second friction brake member and said first friction brake member are positioned in said steering knob in said opening thereof so that an outer surface of each of said second friction brake member, said first friction brake member and said adjusting ring is substantially flush with said end face of said steering knob.

41. The endoscope according to claim 39, wherein said adjusting ring prevents said first friction brake member from moving out of said opening.

42. The endoscope according to claim 37, wherein said engaging portion comprises at least one hole which is formed on the surface of said first friction brake member which is exposed to said opening.

43. The endoscope according to claim 42, wherein said engaging portion comprises two holes which are formed on said surface of said first friction brake member, and
   wherein two pins of a pin face wrench can be engaged in said two holes, respectively.

44. The endoscope according to claim 39, wherein said engaging portion comprises at least one hole which is formed on that surface of said adjusting ring which is exposed to said opening.

45. The endoscope according to claim 44, wherein said engaging portion comprises two holes which are formed on said surface of said adjusting ring, and
   wherein two pins of a pin face wrench can be engaged in said at least two holes, respectively.

46. The endoscope according to claim 35, wherein said first friction brake member and said second friction brake member can be mounted to and dismounted from said steering knob via said opening.

47. The endoscope according to claim 35, wherein said lock operation member is positioned to face said opening of said steering knob, and
   wherein said locking force adjusting device is accessible from the outside of said endoscope via a portion of said opening to which said lock operation member does not face.

48. An endoscope having an elongated insertion portion provided at a distal end thereof with a steerable bendable portion, said endoscope comprising:
   first and second hollow steering knobs which are manually turned independently of each other about a shaft to bend said bendable portion, wherein said first and second hollow steering knobs are positioned adjacent to each other in a direction of an axis of said shaft;
   a first opening formed on said first hollow steering knobs;
   a second opening formed on said second said two hollow steering knobs;
   a first friction brake member, provided for each of said first and second hollow steering knobs, which rotates together with associated one of said first and second hollow steering knobs when associated one of said first and second hollow steering knobs is turned;
   a lock operation member, provided for each of said first and second hollow steering knobs, which can be manually turned relative to associated one of said first and second hollow steering knobs;
   a second friction brake member, provided for each of said first and second hollow steering knobs, which is driven to move toward and away from associated said first friction brake member to lock and unlock associated one of said first and second hollow steering knobs in accordance with rotation of associated said lock operation member relative to said associated hollow steering knob; and
   a locking force adjusting device for adjusting an initial space between said first friction brake member and said second friction brake member for each of said first and second hollow steering knobs, said locking force adjusting device being accessible from the outside of said endoscope via associated one of said first and second openings,
   wherein said first and said second openings are formed on said first and second hollow steering knobs to be open in opposite directions so as not to face each other.

49. An endoscope having an elongated insertion portion provided at a distal end thereof with a steerable bendable portion, said endoscope comprising:
   a steering device having a first operation member which is manually turned to bend said bendable portion so as to direct the tip of said bendable portion toward a target part; and a locking device having a second operation member which is manually turned to lock said steering device;

wherein a first friction member provided on said locking device comes into pressing contact with a second friction member provided on said steering device by an operation of said second operation member, and wherein said first friction member is shaped so as to facilitate compression thereof in a direction of the thickness of said first friction member.

50. The endoscope according to claim 49, wherein said first friction member comprises a plurality of gaps for facilitating compression of said first friction member in said direction.

51. The endoscope according to claim 50, wherein said plurality of gaps are formed by a plurality of projections and depressions.

52. The endoscope according to claim 51, wherein said first friction member has a general cylindrical shape, and wherein said plurality of projections and depressions extend across said first friction member in radial directions.

53. The endoscope according to claim 50, wherein said plurality of gaps comprises a plurality of holes.

54. The endoscope according to claim 53, wherein said first friction member has a general cylindrical shape, and wherein said plurality of holes extend across said first friction member in radial directions.

55. The endoscope according to claim 52, wherein said plurality of projections and depressions are arranged at equi-angular intervals about a center of said first friction member.

56. The endoscope according to claim 54, wherein said plurality of holes are arranged at equi-angular intervals about a center of said first friction member.

57. The endoscope according to claim 49, wherein said first friction member is formed in a disk shape so as to be compressed in a direction of the thickness of said first friction member easier than in a radial direction of said first friction member.

58. An endoscope having an elongated insertion portion provided at a distal end thereof with a steerable bendable portion, said endoscope comprising:

a steering device having a first operation member which is manually turned about a shaft to bend said bendable portion so as to direct a tip of said bendable portion toward a target part;

a locking device having a second operation member which is manually turned about said shaft to lock said steering device;

a first friction member which is provided as an element of said locking device which is movable in a direction of an axis of said shaft and does not rotate about said axis;

a second friction member which rotates together with said first operation member; and a cam mechanism, elements of which are provided on said second operation member and said first friction member;

wherein said first friction member is moved in said direction of said axis of said shaft to come into contact with said second friction member to restrict rotation of said first operation member via said cam mechanism.

59. The endoscope according to claim 58, wherein said locking device comprises:

a rotational member which is provided integral with said second operation member; and an axially-movable lock member which is positioned to face said second friction member and is movable in said direction of said axis of said shaft without being rotatable about said axis, said first friction member being fixed to said axially-movable lock member;

wherein said cam mechanism comprises:

at least one cam follower fixed to said rotational member; and at least one cam groove which is formed on said axially-movable lock member and in which said cam follower is engaged, wherein turning said second operation member causes said axially-movable lock member to move in said direction of said axis of said shaft via an engagement of said cam follower and said cam groove so that said first friction member comes into contact with said second friction member to restrict rotation of said first operation member.

60. The endoscope according to claim 59, wherein said cam groove comprises an inclined groove portion which is inclined with respect to a plane which is perpendicular to said axis of said shaft.

61. The endoscope according to claim 59, wherein said axially-movable lock member comprises at least one leaf spring portion which can elastically bend with respect to said axially-movable lock member, and wherein an under surface of said leaf spring portion constitutes a part of a cam surface of said cam groove.

62. The endoscope according to claim 61, wherein said leaf spring portion of axially-movable lock member comprises a slit, wherein said cam groove connects with an external portion of said axially-movable lock member via said slit.

63. The endoscope according to claim 59, wherein at least one end of said cam groove is formed to be wider than a middle portion of said cam groove.

64. The endoscope according to claim 59, wherein each of opposite ends of said cam groove is formed to have a substantially circulr cross section, and wherein a diameter of each of said opposite ends of said cam groove is slightly greater than a diameter of said cam follower.

* * * * *